(12) United States Patent
Wang et al.

(10) Patent No.: US 10,875,903 B2
(45) Date of Patent: Dec. 29, 2020

(54) BIFUNCTIONAL FUSION PROTEINS TO INHIBIT ANGIOGENESIS IN TUMOR MICROENVIRONMENT AND TO ACTIVATE ADAPTIVE IMMUNE RESPONSES AND THE GENES AND USES THEREOF

(71) Applicant: CHINA PHARMACEUTICAL UNIVERSITY, Nanjing (CN)

(72) Inventors: Shuzhen Wang, Nanjing (CN); Yijun Chen, Nanjing (CN); Dongyang He, Nanjing (CN); Nan Liu, Nanjing (CN); Chao Ma, Nanjing (CN); Zhenyue Gao, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 313 days.

(21) Appl. No.: 14/895,959

(22) PCT Filed: May 5, 2014

(86) PCT No.: PCT/CN2014/076768
§ 371 (c)(1),
(2) Date: Dec. 4, 2015

(87) PCT Pub. No.: WO2014/180288
PCT Pub. Date: Nov. 13, 2014

(65) Prior Publication Data
US 2020/0062818 A1 Feb. 27, 2020

(30) Foreign Application Priority Data

May 6, 2013 (CN) .......................... 2013 1 0162738
May 6, 2013 (CN) .......................... 2013 1 0163407

(51) Int. Cl.
| | |
|---|---|
| *C07K 19/00* | (2006.01) |
| *A61K 38/17* | (2006.01) |
| *A61P 35/00* | (2006.01) |
| *A61P 37/02* | (2006.01) |
| *C07K 14/705* | (2006.01) |
| *C07K 14/78* | (2006.01) |
| *C12N 15/62* | (2006.01) |
| *A61K 38/00* | (2006.01) |
| *C07K 14/435* | (2006.01) |

(52) U.S. Cl.
CPC ............ *C07K 14/705* (2013.01); *C07K 14/78* (2013.01); *C12N 15/62* (2013.01); *A61K 38/00* (2013.01); *C07K 14/435* (2013.01); *C07K 14/70596* (2013.01); *C07K 2317/00* (2013.01); *C07K 2317/74* (2013.01); *C07K 2319/30* (2013.01)

(58) Field of Classification Search
CPC ............ C07K 2317/00; C07K 2314/74; C07K 14/435; C07K 14/70596; C07K 14/705; C07K 14/78; C07K 2319/30; A61K 38/17; A61K 38/00; C12N 15/62; A61P 9/00; A61P 43/00; A61P 37/02; A61P 35/00
See application file for complete search history.

(56) References Cited

U.S. PATENT DOCUMENTS

| | | | |
|---|---|---|---|
| 2013/0288963 | A1 | 10/2013 | Pieczykolan et al. |
| 2015/0274827 | A1 | 10/2015 | Pfizenmaier et al. |

FOREIGN PATENT DOCUMENTS

| | | |
|---|---|---|
| CN | 101265482 A | 9/2009 |
| CN | 103214584 A | 7/2013 |
| CN | 103232543 A | 8/2013 |

OTHER PUBLICATIONS

Dermer et al., Bio/Technology 12:320 (Year: 1994).*
International Search Report; PCT/CN2014/076768; International Filing Date: May 5, 2014; 3 pgs.
Written Opinion; PCT/CN2014/076768; International Filing Date: May 5, 2014; 7 pgs.
International Preliminary Report on Patentability; PCT/CN2014/076768; International Filing Date: May 5, 2014; 8 pgs.
Wang, Shuzhen: Soluble expression of recombinant human CD137 ligand in *Escherichia coli* by co-expression of chaperones; J Ind Microbiol Biotechnol (2012) 39:471-476.

* cited by examiner

*Primary Examiner* — Phuong Huynh
(74) *Attorney, Agent, or Firm* — Schmeiser, Olsen & Watts, LLP

(57) ABSTRACT

Bifunctional fusion proteins having Tumstatin active fragments and CD137L extracellular regions are provided. The proteins exhibit activities to inhibit the proliferation of human umbilical vein endothelial cells and to costimulate the proliferation of T cells. They can be used for the treatment of various tumor-related diseases and the regulation of angiogenesis and immunological effects in humans.

6 Claims, 6 Drawing Sheets

Specification includes a Sequence Listing.

SEQUENCE LISTING

```
<160> NUMBER OF SEQ ID NOS: 113

<210> SEQ ID NO 1
<211> LENGTH: 729
<212> TYPE: DNA
<213> ORGANISM: Artificial Sequence
<220> FEATURE:
<223> OTHER INFORMATION: A gene coding for a bifunctional recombinant
      protein possessing the activities of Tumstatin and CD137L
      (Tumstatin1-Peptide linker 1-CD137L5)

<400> SEQUENCE: 1 ggttttctt   tcttatttgt   tcaaggcaat   cagcgtgctc   atggacaaga   tttggggact      60
cttggttcct  gtctccagcg   cttcaccaca   atgcctttc    tattctgcaa   cgtcaatgac     120
gtatgtaact  ttgcctcacg   aaatgattat   tcgtactggc   tgggaggtgg   tggatcaggt    180
ggaggtggat  ctggtggagg   tggaagtgga   tccggcctct   tggacctgcg   gcagggcatg    240
tttgcgcagc  tggtggccca   aaatgttctg   ctgatcgatg   ggccctgag    ctggtacagt    300 gacccaggcc  tggcaggcgt   gtccctgacg   gggggcctga   gctacaaaga   ggacacgaag    360
gagctggtgg  tggccaaggc   tggagtctac   tatgtcttct   ttcaactaga   gctgcggcgc    420
gtggtggccg  gcgagggctc   aggctccgtt   tcacttgcgc   tgcacctgca   gccactgcgc    480
tctgctgctg  gggccgccgc   cctggctttg   accgtggacc   tgccacccgc   ctcctccgag    540
gctcggaact  cggccttcgg   tttccagggc   cgcttgctgc   acctgagtgc   cggccagcgc    600
ctgggcgtcc  atcttcacac   tgaggccagg   gcacgccatg   cctggcagct   tacccagggc    660
gccacagtct  tgggactctt   ccgggtgacc   cccgaaatcc   cagccggact   cccttcaccg    720
aggtcggaa                                                                    729

<210> SEQ ID NO 2
<211> LENGTH: 597
<212> TYPE: DNA
<213> ORGANISM: Artificial Sequence
<220> FEATURE:
<223> OTHER INFORMATION: A gene coding for a bifunctional recombinant
      protein possessing the activities of Tumstatin and CD137L
      (Tumstatin1-Peptide linker 1-CD137L6)

<400> SEQUENCE: 2 ggttttctt   tcttatttgt   tcaaggcaat   cagcgtgctc   atggacaaga   tttggggact      60
cttggttcct  gtctccagcg   cttcaccaca   atgcctttc    tattctgcaa   cgtcaatgac     120
gtatgtaact  ttgcctcacg   aaatgattat   tcgtactggc   tgggaggtgg   tggatcaggt    180
ggaggtggat  ctggtggagg   tggaagtgga   tccgccgtct   tcctcgcctg   ccctgggcc    240
```

```
gtgtccgggg ctcgcgcctc gcccggctcc gcggccagcc cgagactccg cgagggtccc    300
gagctttcgc ccgacgatcc cgccggcctc ttgctgcagc cactgcgctc tgctgctggg    360
gccgccgccc tggctttgac cgtggacctg ccacccgcct cctccgaggc tcggaactcg    420
gccttcggtt tccagggccg cttgctgcac ctgagtgccg ccagcgcct gggcgtccat     480 cttcacactg aggccagggc acgccatgcc tggcagctta cccagggcgc acagtcttg     540 ggactcttcc gggtgacccc cgaaatccca gccggactcc cttcaccgag gtcggaa      597
```

```
<210> SEQ ID NO 3
<211> LENGTH: 750
<212> TYPE: DNA
<213> ORGANISM: Artificial Sequence
<220> FEATURE:
<223> OTHER INFORMATION: A gene coding for a bifunctional recombinant
      protein possessing the activities of Tumstatin and CD137L
      (Tumstatin1-Peptide linker 5-CD137L5)

<400> SEQUENCE: 3 ggttttttctt tcttatttgt tcaaggcaat cagcgtgctc atggacaaga tttggggact    60
cttggttcct gtctccagcg cttcaccaca atgcctttc tattctgcaa cgtcaatgac    120
gtatgtaact ttgcctcacg aaatgattat tcgtactggc tggctgaagc tgctgccaaa    180
gaagccgctg ctaaggaagc agctgccaag gaagccgctg ccaaggccgg atccggcctc    240
ttggacctgc ggcagggcat gtttgcgcag ctggtggccc aaaatgttct gctgatcgat    300
gggcccctga ctggtacag tgacccaggc ctggcaggcg tgtccctgac gggggggcctg    360 agctacaaag aggacacgaa ggagctggtg gtggccaagg ctggagtcta ctatgtcttc    420
tttcaactag agctgcggcg cgtggtggcc ggcgagggct caggctccgt ttcacttgcg    480
ctgcacctgc agccactgcg ctctgctgct ggggccgccg ccctggcttt gaccgtggac    540
ctgccacccg cctcctccga ggctcggaac tcggccttcg gtttccaggg ccgcttgctg    600
cacctgagtg ccgccagcg cctgggcgtc catcttcaca ctgaggccag ggcacgccat    660
gcctggcagc ttacccaggg cgccacagt ttgggactct ccgggtgac ccccgaaatc     720 ccagccggac tcccttcacc gaggtcggaa                                    750
```

```
<210> SEQ ID NO 4
<211> LENGTH: 618
<212> TYPE: DNA
<213> ORGANISM: Artificial Sequence
<220> FEATURE:
<223> OTHER INFORMATION: A gene coding for a bifunctional recombinant
      protein possessing the activities of Tumstatin and CD137L
      (Tumstatin1-Peptide linker 5-CD137L6)

<400> SEQUENCE: 4 ggttttttctt tcttatttgt tcaaggcaat cagcgtgctc atggacaaga tttggggact    60
cttggttcct gtctccagcg cttcaccaca atgcctttc tattctgcaa cgtcaatgac    120
gtatgtaact ttgcctcacg aaatgattat tcgtactggc tggctgaagc tgctgccaaa    180
gaagccgctg ctaaggaagc agctgccaag gaagccgctg ccaaggccgg atccgccgtc    240
ttcctcgcct gccctgggc cgtgtccggg gctcgcgcct cgcccggctc gcggccagc     300 ccgagactcc gcgagggtcc cgagctttcg cccgacgatc cgccggcct cttgctgcag    360 ccactgcgct ctgctgctgg ggccgccgcc ctggctttga ccgtggacct gccacccgcc    420
tcctccgagg ctcggaactc ggccttcggt tccagggcc gcttgctgca cctgagtgcc    480
```

| | | |
|---|---|---|
| ggccagcgcc tgggcgtcca tcttcacact gaggccaggg cacgccatgc ctggcagctt | 540 | |
| acccagggcg ccacagtctt gggactcttc cgggtgaccc ccgaaatccc agccggactc | 600 | |
| ccttcaccga ggtcggaa | 618 | |

<210> SEQ ID NO 5
<211> LENGTH: 747
<212> TYPE: DNA
<213> ORGANISM: Artificial Sequence
<220> FEATURE:
<223> OTHER INFORMATION: A gene coding for a bifunctional recombinant protein possessing the activities of Tumstatin and CD137L (Tumstatin7-Peptide linker 1-CD137L1)

<400> SEQUENCE: 5

| | |
|---|---|
| acaatgccat tcttattctg caatgtcaat gatgtatgta attttgcatc tcgtaatgat | 60 |
| tattcatact ggctgggagg tggtggatca ggtggaggtg gatctggtgg aggtggaagt | 120 |
| gccgtcttcc tcgcctgccc ctgggccgtg tccggggctc gcgcctcgcc cggctccgcg | 180 |
| gccagcccga gactccgcga gggtcccgag ctttcgcccg acgatcccgc cggcctcttg | 240 |
| gacctgcggc agggcatgtt tgcgcagctg gtggcccaaa atgttctgct gatcgatggg | 300 |
| cccctgagct ggtacagtga cccaggcctg gcaggcgtgt ccctgacggg gggcctgagc | 360 |
| tacaaagagg acacgaagga gctggtggtg gccaaggctg agtctactat tgtcttcttt | 420 |
| caactagagc tgcggcgcgt ggtggccggc gagggctcag gctccgtttc acttgcgctg | 480 |
| cacctgcagc cactgcgctc tgctgctggg gccgccgccc tggctttgac cgtggacctg | 540 |
| ccacccgcct cctccgaggc tcggaactcg gccttcggtt ccagggccg cttgctgcac | 600 |
| ctgagtgccg ccagcgcct gggcgtccat cttcacactg aggccagggc acgccatgcc | 660 |
| tggcagctta cccagggcgc cacagtcttg ggactcttcc gggtgacccc cgaaatccca | 720 |
| gccggactcc cttcaccgag gtcggaa | 747 |

<210> SEQ ID NO 6
<211> LENGTH: 759
<212> TYPE: DNA
<213> ORGANISM: Artificial Sequence
<220> FEATURE:
<223> OTHER INFORMATION: A gene coding for a bifunctional recombinant protein possessing the activities of Tumstatin and CD137L (Tumstatin7-Peptide linker 2-CD137L1)

<400> SEQUENCE: 6

| | |
|---|---|
| acaatgccat tcttattctg caatgtcaat gatgtatgta attttgcatc tcgtaatgat | 60 |
| tattcatact ggctgggagg tggtggatca ggtggaggtg gatctggtgg aggtggatct | 120 |
| ggtggaggat ccgccgtctt cctcgcctgc cctgggccg tgtccggggc tcgcgcctcg | 180 |
| cccggctccg cggccagccc gagactccgc gagggtcccg agctttcgcc cgacgatccc | 240 |
| gccggcctct tggacctgcg gcagggcatg tttgcgcagc tggtggccca aaatgttctg | 300 |
| ctgatcgatg ggcccctgag ctggtacagt gacccaggcc tggcaggcgt gtccctgacg | 360 |
| gggggcctga gctacaaaga ggacacgaag gagctggtgg tggccaaggc tgagtctac | 420 |
| tatgtcttct ttcaactaga gctgcggcgc gtggtggccg gcgagggctc aggctccgtt | 480 |
| tcacttgcgc tgcacctgca gccactgcgc tctgctgctg ggccgccgc cctggctttg | 540 |
| accgtggacc tgccacccgc ctcctccgag gctcggaact cggccttcgg tttccagggc | 600 |
| cgcttgctgc acctgagtgc cgccagcgcc ctgggcgtcc atcttcacac tgaggccagg | 660 |
| gcacgccatg cctggcagct tacccagggc gccacagtct tgggactctt ccgggtgacc | 720 |

```
cccgaaatcc cagccggact cccttcaccg aggtcggaa                759
```

<210> SEQ ID NO 7
<211> LENGTH: 735
<212> TYPE: DNA
<213> ORGANISM: Artificial Sequence
<220> FEATURE:
<223> OTHER INFORMATION: A gene coding for a bifunctional recombinant
      protein possessing the activities of Tumstatin and CD137L
      (Tumstatin7-Peptide linker 3-CD137L1)

<400> SEQUENCE: 7

```
acaatgccat tcttattctg caatgtcaat gatgtatgta attttgcatc tcgtaatgat   60
tattcatact ggctgggagg tggtggatca ggtggaggtc ctggatccgc cgtcttcctc  120
gcctgcccct gggccgtgtc cggggctcgc gcctcgcccg ctccgcggcc cagcccgaga  180
ctccgcgagg gtcccgagct ttcgcccgac gatcccgccg gcctcttgga cctgcggcag  240
ggcatgtttg cgcagctggt ggcccaaaat gttctgctga tcgatgggcc cctgagctgg  300
tacagtgacc caggcctggc aggcgtgtcc ctgacggggg gcctgagcta caaagaggac  360
acgaaggagc tggtggtggc caaggctgga gtctactatg tcttctttca actagagctg  420
cggcgcgtgg tggccggcga gggctcaggc tccgtttcac ttgcgctgca cctgcagcca  480
ctgcgctctg ctgctgggc cgccgccctg gctttgaccg tggacctgcc acccgcctcc  540
tccgaggctc ggaactcggc cttcggtttc agggccgct tgctgcacct gagtgccggc  600
cagcgcctgg gcgtccatct tcacactgag gccaggcac gccatgcctg gcagcttacc  660
cagggcgcca cagtcttggg actcttccgg gtgaccccg aaatcccagc cggactccct  720
tcaccgaggt cggaa                                                   735
```

<210> SEQ ID NO 8
<211> LENGTH: 750
<212> TYPE: DNA
<213> ORGANISM: Artificial Sequence
<220> FEATURE:
<223> OTHER INFORMATION: A gene coding for a bifunctional recombinant
      protein possessing the activities of Tumstatin and CD137L
      (Tumstatin7-Peptide linker 4-CD137L1)

<400> SEQUENCE: 8

```
acaatgccat tcttattctg caatgtcaat gatgtatgta attttgcatc tcgtaatgat   60
tattcatact ggctgggagg tggtggatca ggtggaggtc ctggatcagg tggaggtgga  120
tccgccgtct tcctcgcctg ccctgggcc gtgtccgggg ctcgcgcctc gcccggctcc  180
gcggccagcc cgagactccg cgagggtccc gagctttcgc ccgacgatcc cgccggcctc  240
ttggacctgc ggcagggcat gtttgcgcag ctggtggccc aaaatgttct gctgatcgat  300
gggcccctga gctggtacag tgacccaggc ctggcaggcg tgtccctgac ggggggcctg  360
agctacaaag aggacacgaa ggagctggtg gtggccaagg ctggagtcta ctatgtcttc  420
tttcaactag agctgcggcg cgtggtggcc ggcgagggct caggctccgt ttcacttgcg  480
ctgcacctgc agccactgcg ctctgctgct ggggccgccg ccctggcttt gaccgtggac  540
ctgccacccg cctcctccga ggctcggaac tcggccttcg gtttcagggc cgcttgctg  600
cacctgagtg ccggccagcg cctgggcgtc catcttcaca ctgaggccag gcacgccat  660
gcctggcagc ttacccaggg cgccacagtc ttgggactct ccgggtgac ccccgaaatc  720
ccagccggac tcccttcacc gaggtcggaa                                   750
```

<210> SEQ ID NO 9
<211> LENGTH: 774
<212> TYPE: DNA
<213> ORGANISM: Artificial Sequence
<220> FEATURE:
<223> OTHER INFORMATION: A gene coding for a bifunctional recombinant
    protein possessing the activities of Tumstatin and CD137L
    (Tumstatin7-Peptide linker 5-CD137L1)

<400> SEQUENCE: 9

```
acaatgccat tcttattctg caatgtcaat gatgtatgta attttgcatc tcgtaatgat      60
tattcatact ggctggctga agctgctgcc aaagaagccg ctgctaagga agcagctgcc     120
aaggaagccg ctgccaaggc cggatccgcc gtcttcctcg cctgcccctg ggccgtgtcc     180
ggggctcgcg cctcgcccgg ctccgcggcc agcccgagac tccgcgaggg tcccgagctt     240
tcgcccgacg atcccgccgg cctcttggac ctgcggcagg gcatgtttgc gcagctggtg     300
gcccaaaatg ttctgctgat cgatgggccc ctgagctggt acagtgaccc aggcctggca     360
ggcgtgtccc tgacgggggg cctgagctac aagaggaca cgaaggagct ggtggtggcc     420
aaggctggag tctactatgt cttctttcaa ctagagctgc ggcgcgtggt ggccggcgag     480
ggctcaggct ccgtttcact gcgctgcac ctgcagccac tgcgctctgc tgctggggcc     540
gccgccctgg ctttgaccgt ggacctgcca cccgcctcct ccgaggctcg gaactcggcc     600
ttcggtttcc agggccgctt gctgcacctg agtgccggcc agcgcctggg cgtccatctt     660
cacactgagg ccagggcacg ccatgcctgg cagcttaccc agggcgccac agtcttggga     720
ctcttccggg tgaccccgga atcccagccg gactcccctt caccgaggtc ggaa           774
```

<210> SEQ ID NO 10
<211> LENGTH: 789
<212> TYPE: DNA
<213> ORGANISM: Artificial Sequence
<220> FEATURE:
<223> OTHER INFORMATION: A gene coding for a bifunctional recombinant
    protein possessing the activities of Tumstatin and CD137L
    (Tumstatin7-Peptide linker 6-CD137L1)

<400> SEQUENCE: 10

```
acaatgccat tcttattctg caatgtcaat gatgtatgta attttgcatc tcgtaatgat      60
tattcatact ggctggctga agctgctgcc aaagaagccg ctgctaagga agcagctgcc     120
aaggaagccg ctgccaaggc cgctgcagcc aaggctggat ccgccgtctt cctcgcctgc     180
ccctgggccc tgtccggggc tcgcgcctcg cccggctccg cggccagccc gagactccgc     240
gagggtcccg agctttcgcc cgacgatccc gccggcctct ggacctgcg gcagggcatg     300 tttgcgcagc tggtggccca aaatgttctg ctgatcgatg ggcccctgag ctggtacagt     360
gacccaggcc tggcaggcgt gtccctgacg ggggcctga gctacaaaga ggacacgaag     420
gagctggtgg tggccaaggc tggagtctac tatgtcttct ttcaactaga gctgcggcgc     480
gtggtggccg gcgagggctc aggctccgtt tcacttgcgc tgcacctgca gccactgcgc     540
tctgctgctg ggccgccgc cctggctttg accgtggacc tgccacccgc ctcctccgag     600
gctcggaact cggccttcgg tttccagggc cgcttgctgc acctgagtgc cggccagcgc     660
ctgggcgtcc atcttcacac tgaggccagg gcacgccatg cctggcagct tacccagggc     720
gccacagtct tgggactctt ccgggtgacc ccgaaatcc cagccggact cccttcaccg     780
aggtcggaa                                                             789
```

<210> SEQ ID NO 11
<211> LENGTH: 759
<212> TYPE: DNA
<213> ORGANISM: Artificial Sequence
<220> FEATURE:
<223> OTHER INFORMATION: A gene coding for a bifunctional recombinant
protein possessing the activities of Tumstatin and CD137L
(Tumstatin7-Peptide linker 7-CD137L1)

<400> SEQUENCE: 11

| acaatgccat | tcttattctg | caatgtcaat | gatgtatgta | attttgcatc | tcgtaatgat | 60 |
| tattcatact | ggctggctga | agctgctgcc | aaagaagccg | ctgctaagga | agcagctgcc | 120 |
| aaggctggat | ccgccgtctt | cctcgcctgc | cctgggccg | tgtccggggc | tcgcgcctcg | 180 |
| cccggctccg | cggccagccc | gagactccgc | gagggtcccg | agctttcgcc | cgacgatccc | 240 |
| gccggcctct | tggacctgcg | cagggcatg | tttgcgcagc | tggtggccca | aaatgttctg | 300 |
| ctgatcgatg | ggcccctgag | ctggtacagt | gacccaggcc | tggcaggcgt | gtccctgacg | 360 |
| ggggccctga | gctacaaaga | ggacacgaag | gagctggtgg | tggccaaggc | tggagtctac | 420 |
| tatgtcttct | ttcaactaga | gctgcggcgc | gtggtggccg | gcgagggctc | aggctccgtt | 480 |
| tcacttgcgc | tgcacctgca | gccactgcgc | tctgctgctg | gggccgccgc | cctggctttg | 540 |
| accgtggacc | tgccacccgc | ctcctccgag | gctcggaact | cggccttcgg | tttccagggc | 600 |
| cgcttgctgc | acctgagtgc | cggccagcgc | ctgggcgtcc | atcttcacac | tgaggccagg | 660 |
| gcacgccatg | cctggcagct | acccagggc | gccacagtct | tgggactctt | ccgggtgacc | 720 |
| cccgaaatcc | cagccggact | cccttcaccg | aggtcggaa | | | 759 |

<210> SEQ ID NO 12
<211> LENGTH: 777
<212> TYPE: DNA
<213> ORGANISM: Artificial Sequence
<220> FEATURE:
<223> OTHER INFORMATION: A gene coding for a bifunctional recombinant
protein possessing the activities of Tumstatin and CD137L
(Tumstatin7-Peptide linker 8-CD137L1)

<400> SEQUENCE: 12

| acaatgccat | tcttattctg | caatgtcaat | gatgtatgta | attttgcatc | tcgtaatgat | 60 |
| tattcatact | ggctggctga | agctgctgcc | aaagaagccg | ctgctaagga | agcagctgcc | 120 |
| aaggaagccg | ctgccaaggc | ccctggatcc | gccgtcttcc | tcgcctgccc | ctgggccgtg | 180 |
| tccggggctc | gcgcctcgcc | cggctccgcg | gccagcccga | gactccgcga | gggtcccgag | 240 |
| ctttcgcccg | acgatcccgc | cggctcttg | gacctgcggc | agggcatgtt | tgcgcagctg | 300 |
| gtggcccaaa | atgttctgct | gatcgatggg | cccctgagct | ggtacagtga | cccaggcctg | 360 |
| gcaggcgtgt | ccctgacggg | gggcctgagc | tacaaagagg | acacgaagga | gctggtggtg | 420 |
| gccaaggctg | gagtctacta | tgtcttcttt | caactagagc | tgcggcgcgt | ggtggccggc | 480 |
| gagggctcag | gctccgtttc | acttgcgctg | cacctgcagc | cactgcgctc | tgctgctggg | 540 |
| gccgccgccc | tggctttgac | cgtggacctg | ccacccgcct | cctccgaggc | tcggaactcg | 600 |
| gccttcggtt | tccagggccg | cttgctgcac | ctgagtgccg | gccagcgcct | gggcgtccat | 660 |
| cttcacactg | aggccaggc | acgccatgcc | tggcagctta | cccagggcgc | cacagtcttg | 720 |
| ggactcttcc | gggtgacccc | cgaaatccca | gccggactcc | cttcaccgag | gtcggaa | 777 |

<210> SEQ ID NO 13
<211> LENGTH: 786
<212> TYPE: DNA

<213> ORGANISM: Artificial Sequence
<220> FEATURE:
<223> OTHER INFORMATION: A gene coding for a bifunctional recombinant
protein possessing the activities of Tumstatin and CD137L
(Tumstatin2-Peptide linker 1-CD137L5)

<400> SEQUENCE: 13

| | | | | | |
|---|---|---|---|---|---|
| caagatttag | gtactttggg | ctcttgtctt | cagcgtttta | ccacaatgcc | tttcctcttt | 60 |
| tgcaatgtta | acgacgtctg | taatttcgct | tcccgcaacg | attattcata | ctggctatcg | 120 |
| acgcccgccc | tgatgccaat | gaatatggca | ccgattactg | gacgagcgtt | agaaccttat | 180 |
| atcagtcggt | gcaccgtatg | tgaggggccc | gctatagccg | gaggtggtgg | atcaggtgga | 240 |
| ggtggatctg | gtggaggtgg | aagtggatcc | ggcctcttgg | acctgcggca | gggcatgttt | 300 |
| gcgcagctgg | tggcccaaaa | tgttctgctg | atcgatgggc | ccctgagctg | gtacagtgac | 360 |
| ccaggcctgg | caggcgtgtc | cctgacgggg | ggcctgagct | acaaagagga | cacgaaggag | 420 |
| ctggtggtgg | ccaaggctgg | agtctactat | gtcttctttc | aactagagct | gcggcgcgtg | 480 |
| gtggccggcg | agggctcagg | ctccgtttca | cttgcgctgc | acctgcagcc | actgcgctct | 540 |
| gctgctgggg | ccgccgccct | ggctttgacc | gtggacctgc | cacccgcctc | ctccgaggct | 600 |
| cggaactcgg | ccttcggttt | ccagggccgc | ttgctgcacc | tgagtgccgg | ccagcgcctg | 660 |
| ggcgtccatc | ttcacactga | ggccagggca | cgccatgcct | ggcagcttac | ccagggcgcc | 720 |
| acagtcttgg | gactcttccg | ggtgacccc | gaaatcccag | ccggactccc | ttcaccgagg | 780 |
| tcggaa | | | | | | 786 |

<210> SEQ ID NO 14
<211> LENGTH: 807
<212> TYPE: DNA
<213> ORGANISM: Artificial Sequence
<220> FEATURE:
<223> OTHER INFORMATION: A gene coding for a bifunctional recombinant
protein possessing the activities of Tumstatin and CD137L
(Tumstatin2-Peptide linker 5-CD137L5)

<400> SEQUENCE: 14

| | | | | | |
|---|---|---|---|---|---|
| caagatttag | gtactttggg | ctcttgtctt | cagcgtttta | ccacaatgcc | tttcctcttt | 60 |
| tgcaatgtta | acgacgtctg | taatttcgct | tcccgcaacg | attattcata | ctggctatcg | 120 |
| acgcccgccc | tgatgccaat | gaatatggca | ccgattactg | gacgagcgtt | agaaccttat | 180 |
| atcagtcggt | gcaccgtatg | tgaggggccc | gctatagccg | ctgaagctgc | tgccaaagaa | 240 |
| gccgctgcta | aggaagcagc | tgccaaggaa | gccgctgcca | aggccggatc | cggcctcttg | 300 |
| gacctgcggc | agggcatgtt | tgcgcagctg | gtggcccaaa | atgttctgct | gatcgatggg | 360 |
| cccctgagct | ggtacagtga | cccaggcctg | gcaggcgtgt | ccctgacggg | gggcctgagc | 420 |
| tacaaagagg | acacgaagga | gctggtggtg | gccaaggctg | gagtctacta | tgtcttcttt | 480 |
| caactagagc | tgcggcgcgt | ggtggccggc | gagggctcag | gctccgtttc | acttgcgctg | 540 |
| cacctgcagc | cactgcgctc | tgctgctggg | gccgccgccc | tggctttgac | cgtggacctg | 600 |
| ccacccgcct | cctccgaggc | tcggaactcg | gccttcggtt | tccagggccg | cttgctgcac | 660 |
| ctgagtgccg | gccagcgcct | gggcgtccat | cttcacactg | aggccagggc | acgccatgcc | 720 |
| tggcagctta | cccagggcgc | cacagtcttg | ggactcttcc | gggtgacccc | cgaaatccca | 780 |
| gccggactcc | cttcaccgag | gtcggaa | | | | 807 |

<210> SEQ ID NO 15
<211> LENGTH: 684

<212> TYPE: DNA
<213> ORGANISM: Artificial Sequence
<220> FEATURE:
<223> OTHER INFORMATION: A gene coding for a bifunctional recombinant
      protein possessing the activities of Tumstatin and CD137L
      (Tumstatin3-Peptide linker 1-CD137L5)

<400> SEQUENCE: 15

| | | | |
|---|---|---|---|
| caagatttag gtactttggg ctcttgtctt cagcgtttta ccacaatgcc tttcctcttt | 60 |
| tgcaatgtta acgacgtctg taatttcgct tcccgcaacg attattcata ctggctagga | 120 |
| ggtggtggat caggtggagg tggatctggt ggaggtggaa gtggatccgg cctcttggac | 180 |
| ctgcggcagg gcatgtttgc gcagctggtg gcccaaaatg ttctgctgat cgatgggccc | 240 |
| ctgagctggt acagtgaccc aggcctggca ggcgtgtccc tgacgggggg cctgagctac | 300 |
| aaagaggaca cgaaggagct ggtggtggcc aaggctggag tctactatgt cttctttcaa | 360 |
| ctagagctgc ggcgcgtggt ggccggcgag ggctcaggct ccgtttcact tgcgctgcac | 420 |
| ctgcagccac tgcgctctgc tgctggggcc gccgcctgg ctttgaccgt ggacctgcca | 480 |
| cccgcctcct ccgaggctcg gaactcggcc ttcggtttcc agggccgctt gctgcacctg | 540 |
| agtgccggcc agcgcctggg cgtccatctt cacactgagg ccagggcacg ccatgcctgg | 600 |
| cagcttaccc agggcgccac agtcttggga ctcttccggg tgaccccga aatcccagcc | 660 |
| ggactccctt caccgaggtc ggaa | 684 |

<210> SEQ ID NO 16
<211> LENGTH: 705
<212> TYPE: DNA
<213> ORGANISM: Artificial Sequence
<220> FEATURE:
<223> OTHER INFORMATION: A gene coding for a bifunctional recombinant
      protein possessing the activities of Tumstatin and CD137L
      (Tumstatin3-Peptide linker 5-CD137L5)

<400> SEQUENCE: 16

| | | | |
|---|---|---|---|
| caagatttag gtactttggg ctcttgtctt cagcgtttta ccacaatgcc tttcctcttt | 60 |
| tgcaatgtta acgacgtctg taatttcgct tcccgcaacg attattcata ctggctagct | 120 |
| gaagctgctg ccaaagaagc cgctgctaag aagcagctg ccaaggaagc cgctgccaag | 180 |
| gccggatccg gcctcttgga cctgcggcag ggcatgtttg cgcagctggt ggcccaaaat | 240 |
| gttctgctga tcgatgggcc cctgagctgg tacagtgacc caggcctggc aggcgtgtcc | 300 |
| ctgacggggg gcctgagcta caaagaggac acgaaggagc tggtggtggc caaggctgga | 360 |
| gtctactatg tcttctttca actagagctg cggcgcgtgg tggccggcga gggctcaggc | 420 |
| tccgtttcac ttgcgctgca cctgcagcca ctgcgctctg ctgctggggc cgccgccctg | 480 |
| gctttgaccg tggacctgcc acccgcctcc tccgaggctc ggaactcggc cttcggtttc | 540 |
| cagggccgct tgctgcacct gagtgccggc cagcgcctgg gcgtccatct tcacactgag | 600 |
| gccagggcac gccatgcctg gcagcttacc cagggcgcca cagtcttggg actcttccgg | 660 |
| gtgaccccg aaatcccagc cggactccct tcaccgaggt cggaa | 705 |

<210> SEQ ID NO 17
<211> LENGTH: 675
<212> TYPE: DNA
<213> ORGANISM: Artificial Sequence
<220> FEATURE:
<223> OTHER INFORMATION: A gene coding for a bifunctional recombinant
      protein possessing the activities of Tumstatin and CD137L
      (Tumstatin2-Peptide linker 5-CD137L6)

<400> SEQUENCE: 17

```
caagatttag gtactttggg ctcttgtctt cagcgtttta ccacaatgcc tttcctcttt    60
tgcaatgtta acgacgtctg taatttcgct tcccgcaacg attattcata ctggctatcg   120
acgcccgccc tgatgccaat gaatatggca ccgattactg gacgagcgtt agaaccttat   180
atcagtcggt gcaccgtatg tgaggggccc gctatagccg ctgaagctgc tgccaaagaa   240
gccgctgcta aggaagcagc tgccaaggaa gccgctgcca aggccggatc cgccgtcttc   300
ctcgcctgcc cctgggccgt gtccggggct cgcgcctcgc ccggctccgc ggccagcccg   360
agactccgcg agggtcccga gctttcgccc gacgatcccg ccggcctctt gctgcagcca   420
ctgcgctctg ctgctggggc cgccgccctg gctttgaccg tggacctgcc acccgcctcc   480
tccgaggctc ggaactcggc cttcggtttc cagggccgct tgctgcacct gagtgccggc   540
cagcgcctgg gcgtccatct tcacactgag gccagggcac gccatgcctg cagcttacc   600
cagggcgcca cagtcttggg actcttccgg gtgaccccg aaatcccagc cggactccct   660
tcaccgaggt cggaa                                                    675
```

<210> SEQ ID NO 18
<211> LENGTH: 573
<212> TYPE: DNA
<213> ORGANISM: Artificial Sequence
<220> FEATURE:
<223> OTHER INFORMATION: A gene coding for a bifunctional recombinant protein possessing the activities of Tumstatin and CD137L (Tumstatin3-Peptide linker 5-CD137L6)

<400> SEQUENCE: 18

```
caagatttag gtactttggg ctcttgtctt cagcgtttta ccacaatgcc tttcctcttt    60
tgcaatgtta acgacgtctg taatttcgct tcccgcaacg attattcata ctggctagct   120
gaagctgctg ccaaagaagc cgctgctaag gaagcagctg caaggaagc gctgccaag    180
gccggatccg ccgtcttcct cgcctgcccc tgggccgtgt ccggggctcg cgcctcgccc   240
ggctccgcgg ccagcccgag actccgcgag ggtcccgagc tttcgcccga cgatcccgcc   300
ggcctcttgc tgcagccact gcgctctgct gctggggccg ccgccctggc tttgaccgtg   360
gacctgccac ccgcctcctc cgaggctcgg aactcggcct tcggtttcca gggccgcttg   420
ctgcacctga gtgccggcca gcgcctgggc gtccatcttc acactgaggc cagggcacgc   480
catgcctggc agcttaccca gggcgccaca gtcttgggac tcttccgggt gaccccgaa   540
atcccagccg gactcccttc accgaggtcg gaa                                573
```

<210> SEQ ID NO 19
<211> LENGTH: 786
<212> TYPE: DNA
<213> ORGANISM: Artificial Sequence
<220> FEATURE:
<223> OTHER INFORMATION: A gene coding for a bifunctional recombinant protein possessing the activities of Tumstatin and CD137L (Tumstatin1-Peptide linker 1-CD137L4)

<400> SEQUENCE: 19

```
ggttttcctt tcttatttgt tcaaggcaat cagcgtgctc atggacaaga tttggggact    60
cttggttcct gtctccagcg cttcaccaca atgcctttc tattctgcaa cgtcaatgac   120
gtatgtaact ttgcctcacg aaatgattat tcgtactggc tgggaggtgg tggatcaggt   180
ggaggtggat ctggtggagg tggaagtgga tccgcctgcc cctgggccgt gtccggggct   240
cgcgcctcgc ccggctccgc ggccagcccg agactccgcg agggtcccga gctttcgccc   300
```

```
gacgatcccg ccggcctctt ggacctgcgg cagggcatgt ttgcgcagct ggtggcccaa      360
aatgttctgc tgatcgatgg gcccctgagc tggtacagtg acccaggcct ggcaggcgtg      420
tccctgacgg ggggcctgag ctacaaagag acacgaagg agctggtggt ggccaaggct       480
ggagtctact atgtcttctt tcaactagag ctgcggcgcg tggtggccgg cgagggctca      540
ggctccgttt cacttgcgct gcacctgcag ccactgcgct ctgctgctgg ggccgccgcc      600
ctggctttga ccgtggacct gccacccgcc tcctccgagg ctcggaactc ggccttcggt      660
ttccagggcc gcttgctgca cctgagtgcc ggccagcgcc tgggcgtcca tcttcacact      720
gaggccaggg cacgccatgc ctggcagctt acccagggcg ccacagtctt gggactcttc      780
cgggtg                                                                786
```

<210> SEQ ID NO 20
<211> LENGTH: 843
<212> TYPE: DNA
<213> ORGANISM: Artificial Sequence
<220> FEATURE:
<223> OTHER INFORMATION: A gene coding for a bifunctional recombinant
    protein possessing the activities of Tumstatin and CD137L
    (Tumstatin2-Peptide linker 1-CD137L4)

<400> SEQUENCE: 20

```
caagatttag gtactttggg ctcttgtctt cagcgtttta ccacaatgcc tttcctcttt      60
tgcaatgtta acgacgtctg taatttcgct tcccgcaacg attattcata ctggctatcg     120
acgcccgccc tgatgccaat gaatatggca ccgattactg gacgagcgtt agaaccttat     180
atcagtcggt gcaccgtatg tgaggggccc gctatagccg gaggtggtgg atcaggtgga     240
ggtggatctg gtggaggtgg aagtggatcc gcctgcccct gggccgtgtc cggggctcgc     300
gcctcgcccg gctccgcggc cagcccgaga ctccgcgagg tcccgagct tcgcccgac      360 gatcccgccg gcctcttgga cctgcggcag ggcatgtttg cgcagctggt ggcccaaaat     420
gttctgctga tcgatgggcc cctgagctgg tacagtgacc caggcctggc aggcgtgtcc     480
ctgacggggg gcctgagcta caaagaggac acgaaggagc tggtggtggc caaggctgga     540
gtctactatg tcttctttca actagagctg cggcgcgtgg tggccggcga gggctcaggc     600
tccgtttcac ttgcgctgca cctgcagcca ctgcgctctg ctgctggggc cgccgcctg      660 gctttgaccg tggacctgcc acccgcctcc tccgaggctc ggaactcggc cttcggtttc     720
cagggccgct tgctgcacct gagtgccggc cagcgcctgg gcgtccatct tcacactgag     780
gccagggcac gccatgcctg gcagcttacc cagggcgcca cagtctttggg actcttccgg    840 gtg                                                                   843
```

<210> SEQ ID NO 21
<211> LENGTH: 741
<212> TYPE: DNA
<213> ORGANISM: Artificial Sequence
<220> FEATURE:
<223> OTHER INFORMATION: A gene coding for a bifunctional recombinant
    protein possessing the activities of Tumstatin and CD137L
    (Tumstatin3-Peptide linker 1-CD137L4)

<400> SEQUENCE: 21

```
caagatttag gtactttggg ctcttgtctt cagcgtttta ccacaatgcc tttcctcttt      60
tgcaatgtta acgacgtctg taatttcgct tcccgcaacg attattcata ctggctagga    120
ggtggtggat caggtggagg tggatctggt ggaggtggaa gtggatccgc ctgcccctgg    180
```

| | | |
|---|---|---|
| gccgtgtccg gggctcgcgc ctcgcccggc tccgcggcca gcccgagact ccgcgagggt | 240 |
| cccgagcttt cgcccgacga tcccgccggc ctcttggacc tgcggcaggg catgtttgcg | 300 |
| cagctggtgg cccaaaatgt tctgctgatc gatgggcccc tgagctggta cagtgaccca | 360 |
| ggcctggcag gcgtgtccct gacggggggc ctgagctaca agaggacac gaaggagctg | 420 |
| gtggtggcca aggctggagt ctactatgtc ttctttcaac tagagctgcg gcgcgtggtg | 480 |
| gccggcgagg gctcaggctc cgtttcactt gcgctgcacc tgcagccact gcgctctgct | 540 |
| gctggggccg ccgccctggc tttgaccgtg gacctgccac ccgcctcctc cgaggctcgg | 600 |
| aactcggcct tcggtttcca gggccgcttg ctgcacctga gtgccggcca gcgcctgggc | 660 |
| gtccatcttc acactgaggc cagggcacgc catgcctggc agcttaccca gggcgccaca | 720 |
| gtcttgggac tcttccgggt g | 741 |

<210> SEQ ID NO 22
<211> LENGTH: 807
<212> TYPE: DNA
<213> ORGANISM: Artificial Sequence
<220> FEATURE:
<223> OTHER INFORMATION: A gene coding for a bifunctional recombinant
      protein possessing the activities of Tumstatin and CD137L
      (Tumstatin1-Peptide linker 5-CD137L4)

<400> SEQUENCE: 22

| | | |
|---|---|---|
| ggttttctct tcttatttgt tcaaggcaat cagcgtgctc atggacaaga tttggggact | 60 |
| cttggttcct gtctccagcg cttcaccaca atgccttttc tattctgcaa cgtcaatgac | 120 |
| gtatgtaact ttgcctcacg aaatgattat tcgtactggc tggctgaagc tgctgccaaa | 180 |
| gaagccgctg ctaaggaagc agctgccaag gaagccgctg ccaaggccgg atccgcctgc | 240 |
| ccctgggccg tgtccggggc tcgcgcctcg cccggctccg cggccagccc gagactccgc | 300 |
| gagggtcccg agctttcgcc cgacgatccc gccggcctct ggacctgcg gcagggcatg | 360 |
| tttgcgcagc tggtggccca aaatgttctg ctgatcgatg ggcccctgag ctggtacagt | 420 |
| gacccaggcc tggcaggcgt gtccctgacg gggggcctga gctacaaaga ggacacgaag | 480 |
| gagctggtgg tggccaaggc tggagtctac tatgtcttct tcaactaga gctgcggcgc | 540 |
| gtggtggccg gcgagggctc aggctccgtt tcacttgcgc tgcacctgca gccactgcgc | 600 |
| tctgctgctg gggccgccgc cctggctttg accgtggacc tgccacccgc tcctccgag | 660 |
| gctcggaact cggccttcgg tttccagggc cgcttgctgc acctgagtgc cggccagcgc | 720 |
| ctgggcgtcc atcttcacac tgaggccagg gcacgccatg cctggcagct tacccagggc | 780 |
| gccacagtct tgggactctt ccgggtg | 807 |

<210> SEQ ID NO 23
<211> LENGTH: 864
<212> TYPE: DNA
<213> ORGANISM: Artificial Sequence
<220> FEATURE:
<223> OTHER INFORMATION: A gene coding for a bifunctional recombinant
      protein possessing the activities of Tumstatin and CD137L
      (Tumstatin2-Peptide linker 5-CD137L4)

<400> SEQUENCE: 23

| | | |
|---|---|---|
| caagatttag gtactttggg ctcttgtctt cagcgttta ccacaatgcc tttcctcttt | 60 |
| tgcaatgtta acgacgtctg taatttcgct tcccgcaacg attattcata ctggctatcg | 120 |
| acgcccgccc tgatgccaat gaatatggca ccgattactg gacgagcgtt agaacccttat | 180 |
| atcagtcggt gcaccgtatg tgaggggccc gctatagccg ctgaagctgc tgccaaagaa | 240 |

-continued

```
gccgctgcta aggaagcagc tgccaaggaa gccgctgcca aggccggatc cgcctgcccc    300
tgggccgtgt ccggggctcg cgcctcgccc ggctccgcgg ccagcccgag actccgcgag    360
ggtcccgagc tttcgcccga cgatcccgcc ggcctcttgg acctgcggca gggcatgttt    420
gcgcagctgg tggcccaaaa tgttctgctg atcgatgggc ccctgagctg gtacagtgac    480
ccaggcctgg caggcgtgtc cctgacgggg ggcctgagct acaaagagga cacgaaggag    540
ctggtggtgg ccaaggctgg agtctactat gtcttctttc aactagagct gcggcgcgtg    600
gtggccggcg agggctcagg ctccgtttca cttgcgctgc acctgcagcc actgcgctct    660
gctgctgggg ccgccgccct ggctttgacc gtggacctgc acccgcctc ctccgaggct    720 cggaactcgg ccttcggttt ccagggccgc ttgctgcacc tgagtgccgg ccagcgcctg    780
ggcgtccatc ttcacactga ggccagggca cgccatgcct ggcagcttac ccagggcgcc    840
acagtcttgg gactcttccg ggtg                                           864
```

<210> SEQ ID NO 24
<211> LENGTH: 762
<212> TYPE: DNA
<213> ORGANISM: Artificial Sequence
<220> FEATURE:
<223> OTHER INFORMATION: A gene coding for a bifunctional recombinant
    protein possessing the activities of Tumstatin and CD137L
    (Tumstatin3-Peptide linker 5-CD137L4)

<400> SEQUENCE: 24

```
caagatttag gtactttggg ctcttgtctt cagcgtttta ccacaatgcc tttcctcttt     60
tgcaatgtta acgacgtctg taatttcgct tcccgcaacg attattcata ctggctagct    120
gaagctgctg ccaaagaagc cgctgctaag gaagcagctg ccaaggaagc cgctgccaag    180
gccggatccg cctgcccctg gccgtgtcc ggggctcgcg cctcgccggg ctccgcggcc    240
agcccgagac tccgcgaggg tcccgagctt tcgcccgacg atcccgcggg cctcttggac    300
ctgcggcagg gcatgtttgc gcagctggtg gcccaaaatg ttctgctgat cgatgggccc    360
ctgagctggt acagtgaccc aggcctggca ggcgtgtccc tgacgggggg cctgagctac    420
aaagaggaca cgaaggagct ggtggtggcc aaggctggag tctactatgt cttctttcaa    480
ctagagctgc ggcgcgtggt ggccggcgag ggctcaggct ccgtttcact tgcgctgcac    540
ctgcagccac tgcgctctgc tgctggggcc gccgcctgg ctttgaccgt ggacctgcca    600
cccgcctcct ccgaggctcg gaactcggcc ttcggtttcc agggccgctt gctgcacctg    660
agtgccggcc agcgcctggg cgtccatctt cacactgagg ccagggcacg ccatgcctgg    720
cagcttaccc agggcgccac agtcttggga ctcttccggg tg                      762
```

<210> SEQ ID NO 25
<211> LENGTH: 243
<212> TYPE: PRT
<213> ORGANISM: Artificial Sequence
<220> FEATURE:
<223> OTHER INFORMATION: A bifunctional recombinant protein possessing
    the activities of Tumstatin and CD137L (Tumstatin1-Peptide linker
    1-CD137L5)

<400> SEQUENCE: 25

```
Gly Phe Ser Phe Leu Phe Val Gln Gly Asn Gln Arg Ala His Gly Gln
1               5                   10                  15

Asp Leu Gly Thr Leu Gly Ser Cys Leu Gln Arg Phe Thr Thr Met Pro
            20                  25                  30
```

Phe Leu Phe Cys Asn Val Asn Asp Val Cys Asn Phe Ala Ser Arg Asn
         35                  40                  45

Asp Tyr Ser Tyr Trp Leu Gly Gly Gly Ser Gly Gly Gly Gly Ser
 50                  55                  60

Gly Gly Gly Gly Ser Gly Ser Gly Leu Leu Asp Leu Arg Gln Gly Met
 65                  70                  75                  80

Phe Ala Gln Leu Val Ala Gln Asn Val Leu Leu Ile Asp Gly Pro Leu
                 85                  90                  95

Ser Trp Tyr Ser Asp Pro Gly Leu Ala Gly Val Ser Leu Thr Gly Gly
             100                 105                 110

Leu Ser Tyr Lys Glu Asp Thr Lys Glu Leu Val Val Ala Lys Ala Gly
             115                 120                 125

Val Tyr Tyr Val Phe Phe Gln Leu Glu Leu Arg Arg Val Val Ala Gly
 130                 135                 140

Glu Gly Ser Gly Ser Val Ser Leu Ala Leu His Leu Gln Pro Leu Arg
145                 150                 155                 160

Ser Ala Ala Gly Ala Ala Ala Leu Ala Leu Thr Val Asp Leu Pro Pro
                165                 170                 175

Ala Ser Ser Glu Ala Arg Asn Ser Ala Phe Gly Phe Gln Gly Arg Leu
            180                 185                 190

Leu His Leu Ser Ala Gly Gln Arg Leu Gly Val His Leu His Thr Glu
            195                 200                 205

Ala Arg Ala Arg His Ala Trp Gln Leu Thr Gln Gly Ala Thr Val Leu
            210                 215                 220

Gly Leu Phe Arg Val Thr Pro Glu Ile Pro Ala Gly Leu Pro Ser Pro
225                 230                 235                 240

Arg Ser Glu

<210> SEQ ID NO 26
<211> LENGTH: 197
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin1-Peptide linker
      1-CD137L6)

<400> SEQUENCE: 26

Gly Phe Ser Phe Leu Phe Val Gln Gly Asn Gln Arg Ala His Gly Gln
 1               5                  10                  15

Asp Leu Gly Thr Leu Gly Ser Cys Leu Gln Arg Phe Thr Thr Met Pro
             20                  25                  30

Phe Leu Phe Cys Asn Val Asn Asp Val Cys Asn Phe Ala Ser Arg Asn
         35                  40                  45

Asp Tyr Ser Tyr Trp Leu Gly Gly Gly Ser Gly Gly Gly Gly Ser
 50                  55                  60

Gly Gly Gly Gly Ser Ala Val Phe Leu Ala Cys Pro Trp Ala Val Ser
 65                  70                  75                  80

Gly Ala Arg Ala Ser Pro Gly Ser Ala Ala Ser Pro Arg Leu Arg Glu
                 85                  90                  95

Gly Pro Glu Leu Ser Pro Asp Asp Pro Ala Gly Leu Leu Leu Gln Pro
            100                 105                 110

Leu Arg Ser Ala Ala Gly Ala Ala Ala Leu Ala Leu Thr Val Asp Leu
            115                 120                 125

Pro Pro Ala Ser Ser Glu Ala Arg Asn Ser Ala Phe Gly Phe Gln Gly
            130                 135                 140

```
Arg Leu Leu His Leu Ser Ala Gly Gln Arg Leu Gly Val His Leu His
145                 150                 155                 160

Thr Glu Ala Arg Ala Arg His Ala Trp Gln Leu Thr Gln Gly Ala Thr
                165                 170                 175

Val Leu Gly Leu Phe Arg Val Thr Pro Glu Ile Pro Ala Gly Leu Pro
            180                 185                 190

Ser Pro Arg Ser Glu
        195
```

<210> SEQ ID NO 27
<211> LENGTH: 250
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin1-Peptide linker
      5-CD137L5)

<400> SEQUENCE: 27

```
Gly Phe Ser Phe Leu Phe Val Gln Gly Asn Gln Arg Ala His Gly Gln
1               5                   10                  15

Asp Leu Gly Thr Leu Gly Ser Cys Leu Gln Arg Phe Thr Thr Met Pro
            20                  25                  30

Phe Leu Phe Cys Asn Val Asn Asp Val Cys Asn Phe Ala Ser Arg Asn
        35                  40                  45

Asp Tyr Ser Tyr Trp Leu Ala Glu Ala Ala Lys Glu Ala Ala Ala
    50                  55                  60

Lys Glu Ala Ala Ala Lys Glu Ala Ala Ala Lys Ala Gly Ser Gly Leu
65                  70                  75                  80

Leu Asp Leu Arg Gln Gly Met Phe Ala Gln Leu Val Ala Gln Asn Val
                85                  90                  95

Leu Leu Ile Asp Gly Pro Leu Ser Trp Tyr Ser Asp Pro Gly Leu Ala
            100                 105                 110

Gly Val Ser Leu Thr Gly Gly Leu Ser Tyr Lys Glu Asp Thr Lys Glu
        115                 120                 125

Leu Val Val Ala Lys Ala Gly Val Tyr Tyr Val Phe Phe Gln Leu Glu
    130                 135                 140

Leu Arg Arg Val Val Ala Gly Glu Gly Ser Gly Ser Val Ser Leu Ala
145                 150                 155                 160

Leu His Leu Gln Pro Leu Arg Ser Ala Ala Gly Ala Ala Ala Leu Ala
                165                 170                 175

Leu Thr Val Asp Leu Pro Pro Ala Ser Ser Glu Ala Arg Asn Ser Ala
            180                 185                 190

Phe Gly Phe Gln Gly Arg Leu Leu His Leu Ser Ala Gly Gln Arg Leu
        195                 200                 205

Gly Val His Leu His Thr Glu Ala Arg Ala Arg His Ala Trp Gln Leu
    210                 215                 220

Thr Gln Gly Ala Thr Val Leu Gly Leu Phe Arg Val Thr Pro Glu Ile
225                 230                 235                 240

Pro Ala Gly Leu Pro Ser Pro Arg Ser Glu
                245                 250
```

<210> SEQ ID NO 28
<211> LENGTH: 204
<212> TYPE: PRT
<213> ORGANISM: Artificial Sequence
<220> FEATURE:

<223> OTHER INFORMATION: A bifunctional recombinant protein possessing
      the activities of Tumstatin and CD137L (Tumstatin1-Peptide linker
      5-CD137L6)

<400> SEQUENCE: 28

```
Gly Phe Ser Phe Leu Phe Val Gln Gly Asn Gln Arg Ala His Gly Gln
1               5                   10                  15

Asp Leu Gly Thr Leu Gly Ser Cys Leu Gln Arg Phe Thr Thr Met Pro
            20                  25                  30

Phe Leu Phe Cys Asn Val Asn Asp Val Cys Asn Phe Ala Ser Arg Asn
        35                  40                  45

Asp Tyr Ser Tyr Trp Leu Ala Glu Ala Ala Lys Glu Ala Ala Ala
    50                  55                  60

Lys Glu Ala Ala Ala Lys Glu Ala Ala Ala Lys Ala Ala Val Phe Leu
65                  70                  75                  80

Ala Cys Pro Trp Ala Val Ser Gly Ala Arg Ala Ser Pro Gly Ser Ala
                85                  90                  95

Ala Ser Pro Arg Leu Arg Glu Gly Pro Glu Leu Ser Pro Asp Asp Pro
            100                 105                 110

Ala Gly Leu Leu Leu Gln Pro Leu Arg Ser Ala Ala Gly Ala Ala Ala
        115                 120                 125

Leu Ala Leu Thr Val Asp Leu Pro Pro Ala Ser Ser Glu Ala Arg Asn
130                 135                 140

Ser Ala Phe Gly Phe Gln Gly Arg Leu Leu His Leu Ser Ala Gly Gln
145                 150                 155                 160

Arg Leu Gly Val His Leu His Thr Glu Ala Arg Ala Arg His Ala Trp
                165                 170                 175

Gln Leu Thr Gln Gly Ala Thr Val Leu Gly Leu Phe Arg Val Thr Pro
            180                 185                 190

Glu Ile Pro Ala Gly Leu Pro Ser Pro Arg Ser Glu
        195                 200
```

<210> SEQ ID NO 29
<211> LENGTH: 249
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin7-Peptide linker
      1-CD137L1)

<400> SEQUENCE: 29

```
Thr Met Pro Phe Leu Phe Cys Asn Val Asn Asp Val Cys Asn Phe Ala
1               5                   10                  15

Ser Arg Asn Asp Tyr Ser Tyr Trp Leu Gly Gly Gly Ser Gly Gly
            20                  25                  30

Gly Gly Ser Gly Gly Gly Ser Ala Val Phe Leu Ala Cys Pro Trp
        35                  40                  45

Ala Val Ser Gly Ala Arg Ala Ser Pro Gly Ser Ala Ala Ser Pro Arg
    50                  55                  60

Leu Arg Glu Gly Pro Glu Leu Ser Pro Asp Asp Pro Ala Gly Leu Leu
65                  70                  75                  80

Asp Leu Arg Gln Gly Met Phe Ala Gln Leu Val Ala Gln Asn Val Leu
                85                  90                  95

Leu Ile Asp Gly Pro Leu Ser Trp Tyr Ser Asp Pro Gly Leu Ala Gly
            100                 105                 110

Val Ser Leu Thr Gly Gly Leu Ser Tyr Lys Glu Asp Thr Lys Glu Leu
```

```
            115                 120                 125
Val Val Ala Lys Ala Gly Val Tyr Tyr Val Phe Phe Gln Leu Glu Leu
        130                 135                 140

Arg Arg Val Val Ala Gly Glu Gly Ser Gly Ser Val Ser Leu Ala Leu
145                 150                 155                 160

His Leu Gln Pro Leu Arg Ser Ala Ala Gly Ala Ala Leu Ala Leu
                165                 170                 175

Thr Val Asp Leu Pro Pro Ala Ser Ser Glu Ala Arg Asn Ser Ala Phe
                180                 185                 190

Gly Phe Gln Gly Arg Leu Leu His Leu Ser Ala Gly Gln Arg Leu Gly
                195                 200                 205

Val His Leu His Thr Glu Ala Arg Ala Arg His Ala Trp Gln Leu Thr
        210                 215                 220

Gln Gly Ala Thr Val Leu Gly Leu Phe Arg Val Thr Pro Glu Ile Pro
225                 230                 235                 240

Ala Gly Leu Pro Ser Pro Arg Ser Glu
                245
```

<210> SEQ ID NO 30
<211> LENGTH: 253
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin7-Peptide linker
      2-CD137L1)

<400> SEQUENCE: 30

```
Thr Met Pro Phe Leu Phe Cys Asn Val Asn Asp Val Cys Asn Phe Ala
1               5                   10                  15

Ser Arg Asn Asp Tyr Ser Tyr Trp Leu Gly Gly Gly Ser Gly Gly
                20                  25                  30

Gly Gly Ser Gly Gly Gly Gly Ser Gly Gly Gly Ser Ala Val Phe Leu
            35                  40                  45

Ala Cys Pro Trp Ala Val Ser Gly Ala Arg Ala Ser Pro Gly Ser Ala
50                  55                  60

Ala Ser Pro Arg Leu Arg Glu Gly Pro Glu Leu Ser Pro Asp Asp Pro
65                  70                  75                  80

Ala Gly Leu Leu Asp Leu Arg Gln Gly Met Phe Ala Gln Leu Val Ala
                85                  90                  95

Gln Asn Val Leu Leu Ile Asp Gly Pro Leu Ser Trp Tyr Ser Asp Pro
                100                 105                 110

Gly Leu Ala Gly Val Ser Leu Thr Gly Gly Leu Ser Tyr Lys Glu Asp
            115                 120                 125

Thr Lys Glu Leu Val Val Ala Lys Ala Gly Val Tyr Tyr Val Phe Phe
        130                 135                 140

Gln Leu Glu Leu Arg Arg Val Val Ala Gly Glu Gly Ser Gly Ser Val
145                 150                 155                 160

Ser Leu Ala Leu His Leu Gln Pro Leu Arg Ser Ala Ala Gly Ala Ala
                165                 170                 175

Ala Leu Ala Leu Thr Val Asp Leu Pro Pro Ala Ser Ser Glu Ala Arg
                180                 185                 190

Asn Ser Ala Phe Gly Phe Gln Gly Arg Leu Leu His Leu Ser Ala Gly
            195                 200                 205

Gln Arg Leu Gly Val His Leu His Thr Glu Ala Arg Ala Arg His Ala
        210                 215                 220
```

-continued

Trp Gln Leu Thr Gln Gly Ala Thr Val Leu Gly Leu Phe Arg Val Thr
225                 230                 235                 240

Pro Glu Ile Pro Ala Gly Leu Pro Ser Pro Arg Ser Glu
            245                 250

<210> SEQ ID NO 31
<211> LENGTH: 245
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin7-Peptide linker
      3-CD137L1)

<400> SEQUENCE: 31

Thr Met Pro Phe Leu Phe Cys Asn Val Asn Asp Val Cys Asn Phe Ala
1               5                   10                  15

Ser Arg Asn Asp Tyr Ser Tyr Trp Leu Gly Gly Gly Ser Gly Gly
            20                  25                  30

Gly Pro Gly Ser Ala Val Phe Leu Ala Cys Pro Trp Ala Val Ser Gly
            35                  40                  45

Ala Arg Ala Ser Pro Gly Ser Ala Ala Ser Pro Arg Leu Arg Glu Gly
50                  55                  60

Pro Glu Leu Ser Pro Asp Asp Pro Ala Gly Leu Leu Asp Leu Arg Gln
65                  70                  75                  80

Gly Met Phe Ala Gln Leu Val Ala Gln Asn Val Leu Leu Ile Asp Gly
                85                  90                  95

Pro Leu Ser Trp Tyr Ser Asp Pro Gly Leu Ala Gly Val Ser Leu Thr
            100                 105                 110

Gly Gly Leu Ser Tyr Lys Glu Asp Thr Lys Glu Leu Val Val Ala Lys
            115                 120                 125

Ala Gly Val Tyr Tyr Val Phe Phe Gln Leu Glu Leu Arg Arg Val Val
        130                 135                 140

Ala Gly Glu Gly Ser Gly Ser Val Ser Leu Ala Leu His Leu Gln Pro
145                 150                 155                 160

Leu Arg Ser Ala Ala Gly Ala Ala Ala Leu Ala Leu Thr Val Asp Leu
                165                 170                 175

Pro Pro Ala Ser Ser Glu Ala Arg Asn Ser Ala Phe Gly Phe Gln Gly
            180                 185                 190

Arg Leu Leu His Leu Ser Ala Gly Gln Arg Leu Gly Val His Leu His
        195                 200                 205

Thr Glu Ala Arg Ala Arg His Ala Trp Gln Leu Thr Gln Gly Ala Thr
    210                 215                 220

Val Leu Gly Leu Phe Arg Val Thr Pro Glu Ile Pro Ala Gly Leu Pro
225                 230                 235                 240

Ser Pro Arg Ser Glu
            245

<210> SEQ ID NO 32
<211> LENGTH: 250
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin1-Peptide linker
      4-CD137L1)

<400> SEQUENCE: 32

Thr Met Pro Phe Leu Phe Cys Asn Val Asn Asp Val Cys Asn Phe Ala
1               5                   10                  15

Ser Arg Asn Asp Tyr Ser Tyr Trp Leu Gly Gly Gly Ser Gly Gly
            20                  25                  30

Gly Pro Gly Ser Gly Gly Gly Ser Ala Val Phe Leu Ala Cys Pro
            35                  40                  45

Trp Ala Val Ser Gly Ala Arg Ala Ser Pro Gly Ser Ala Ala Ser Pro
    50                  55                  60

Arg Leu Arg Glu Gly Pro Glu Leu Ser Pro Asp Pro Ala Gly Leu
65                  70                  75                  80

Leu Asp Leu Arg Gln Gly Met Phe Ala Gln Leu Val Ala Gln Asn Val
            85                  90                  95

Leu Leu Ile Asp Gly Pro Leu Ser Trp Tyr Ser Asp Pro Gly Leu Ala
            100                 105                 110

Gly Val Ser Leu Thr Gly Gly Leu Ser Tyr Lys Glu Asp Thr Lys Glu
            115                 120                 125

Leu Val Val Ala Lys Ala Gly Val Tyr Tyr Val Phe Phe Gln Leu Glu
        130                 135                 140

Leu Arg Arg Val Val Ala Gly Glu Gly Ser Gly Ser Val Ser Leu Ala
145                 150                 155                 160

Leu His Leu Gln Pro Leu Arg Ser Ala Ala Gly Ala Ala Ala Leu Ala
                165                 170                 175

Leu Thr Val Asp Leu Pro Pro Ala Ser Ser Glu Ala Arg Asn Ser Ala
                180                 185                 190

Phe Gly Phe Gln Gly Arg Leu Leu His Leu Ser Ala Gly Gln Arg Leu
                195                 200                 205

Gly Val His Leu His Thr Glu Ala Arg Ala Arg His Ala Trp Gln Leu
        210                 215                 220

Thr Gln Gly Ala Thr Val Leu Gly Leu Phe Arg Val Thr Pro Glu Ile
225                 230                 235                 240

Pro Ala Gly Leu Pro Ser Pro Arg Ser Glu
                245                 250

<210> SEQ ID NO 33
<211> LENGTH: 258
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin7-Peptide linker
      5-CD137L1)

<400> SEQUENCE: 33

Thr Met Pro Phe Leu Phe Cys Asn Val Asn Asp Val Cys Asn Phe Ala
1               5                   10                  15

Ser Arg Asn Asp Tyr Ser Tyr Trp Leu Ala Glu Ala Ala Ala Lys Glu
            20                  25                  30

Ala Ala Ala Lys Glu Ala Ala Ala Lys Glu Ala Ala Ala Lys Ala Gly
            35                  40                  45

Ser Ala Val Phe Leu Ala Cys Pro Trp Ala Val Ser Gly Ala Arg Ala
    50                  55                  60

Ser Pro Gly Ser Ala Ala Ser Pro Arg Leu Arg Glu Gly Pro Glu Leu
65                  70                  75                  80

Ser Pro Asp Pro Ala Gly Leu Leu Asp Leu Arg Gln Gly Met Phe
            85                  90                  95

Ala Gln Leu Val Ala Gln Asn Val Leu Leu Ile Asp Gly Pro Leu Ser

```
                100             105             110
Trp Tyr Ser Asp Pro Gly Leu Ala Gly Val Ser Leu Thr Gly Gly Leu
            115                 120             125

Ser Tyr Lys Glu Asp Thr Lys Glu Leu Val Val Ala Lys Ala Gly Val
        130                 135             140

Tyr Tyr Val Phe Phe Gln Leu Glu Leu Arg Arg Val Val Ala Gly Glu
145                 150                 155                 160

Gly Ser Gly Ser Val Ser Leu Ala Leu His Leu Gln Pro Leu Arg Ser
            165                 170             175

Ala Ala Gly Ala Ala Ala Leu Ala Leu Thr Val Asp Leu Pro Pro Ala
        180                 185             190

Ser Ser Glu Ala Arg Asn Ser Ala Phe Gly Phe Gln Gly Arg Leu Leu
            195                 200             205

His Leu Ser Ala Gly Gln Arg Leu Gly Val His Leu His Thr Glu Ala
        210                 215             220

Arg Ala Arg His Ala Trp Gln Leu Thr Gln Gly Ala Thr Val Leu Gly
225                 230                 235                 240

Leu Phe Arg Val Thr Pro Glu Ile Pro Ala Gly Leu Pro Ser Pro Arg
                245                 250             255

Ser Glu

<210> SEQ ID NO 34
<211> LENGTH: 263
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin7-Peptide linker
      6-CD137L1)

<400> SEQUENCE: 34

Thr Met Pro Phe Leu Phe Cys Asn Val Asn Asp Val Cys Asn Phe Ala
1               5                   10                  15

Ser Arg Asn Asp Tyr Ser Tyr Trp Leu Ala Glu Ala Ala Ala Lys Glu
            20                  25                  30

Ala Ala Ala Lys Glu Ala Ala Ala Lys Glu Ala Ala Ala Lys Ala Ala
        35                  40                  45

Ala Ala Lys Ala Gly Ser Ala Val Phe Leu Ala Cys Pro Trp Ala Val
    50                  55                  60

Ser Gly Ala Arg Ala Ser Pro Gly Ser Ala Ala Ser Pro Arg Leu Arg
65                  70                  75                  80

Glu Gly Pro Glu Leu Ser Pro Asp Asp Pro Ala Gly Leu Leu Asp Leu
                85                  90                  95

Arg Gln Gly Met Phe Ala Gln Leu Val Ala Gln Asn Val Leu Leu Ile
            100                 105                 110

Asp Gly Pro Leu Ser Trp Tyr Ser Asp Pro Gly Leu Ala Gly Val Ser
        115                 120                 125

Leu Thr Gly Gly Leu Ser Tyr Lys Glu Asp Thr Lys Glu Leu Val Val
    130                 135                 140

Ala Lys Ala Gly Val Tyr Tyr Val Phe Phe Gln Leu Glu Leu Arg Arg
145                 150                 155                 160

Val Val Ala Gly Glu Gly Ser Gly Ser Val Ser Leu Ala Leu His Leu
                165                 170                 175

Gln Pro Leu Arg Ser Ala Ala Gly Ala Ala Ala Leu Ala Leu Thr Val
            180                 185                 190
```

```
Asp Leu Pro Pro Ala Ser Ser Glu Ala Arg Asn Ser Ala Phe Gly Phe
            195                 200                 205

Gln Gly Arg Leu Leu His Leu Ser Ala Gly Gln Arg Leu Gly Val His
        210                 215                 220

Leu His Thr Glu Ala Arg Ala Arg His Ala Trp Gln Leu Thr Gln Gly
225                 230                 235                 240

Ala Thr Val Leu Gly Leu Phe Arg Val Thr Pro Glu Ile Pro Ala Gly
                245                 250                 255

Leu Pro Ser Pro Arg Ser Glu
            260

<210> SEQ ID NO 35
<211> LENGTH: 253
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin7-Peptide linker
      7-CD137L1)

<400> SEQUENCE: 35

Thr Met Pro Phe Leu Phe Cys Asn Val Asn Asp Val Cys Asn Phe Ala
1               5                   10                  15

Ser Arg Asn Asp Tyr Ser Tyr Trp Leu Ala Glu Ala Ala Ala Lys Glu
            20                  25                  30

Ala Ala Ala Lys Glu Ala Ala Ala Lys Ala Gly Ser Ala Val Phe Leu
        35                  40                  45

Ala Cys Pro Trp Ala Val Ser Gly Ala Arg Ala Ser Pro Gly Ser Ala
    50                  55                  60

Ala Ser Pro Arg Leu Arg Glu Gly Pro Glu Leu Ser Pro Asp Asp Pro
65                  70                  75                  80

Ala Gly Leu Leu Asp Leu Arg Gln Gly Met Phe Ala Gln Leu Val Ala
                85                  90                  95

Gln Asn Val Leu Leu Ile Asp Gly Pro Leu Ser Trp Tyr Ser Asp Pro
            100                 105                 110

Gly Leu Ala Gly Val Ser Leu Thr Gly Gly Leu Ser Tyr Lys Glu Asp
        115                 120                 125

Thr Lys Glu Leu Val Val Ala Lys Ala Gly Val Tyr Tyr Val Phe Phe
    130                 135                 140

Gln Leu Glu Leu Arg Arg Val Val Ala Gly Glu Gly Ser Gly Ser Val
145                 150                 155                 160

Ser Leu Ala Leu His Leu Gln Pro Leu Arg Ser Ala Ala Gly Ala Ala
                165                 170                 175

Ala Leu Ala Leu Thr Val Asp Leu Pro Pro Ala Ser Ser Glu Ala Arg
            180                 185                 190

Asn Ser Ala Phe Gly Phe Gln Gly Arg Leu Leu His Leu Ser Ala Gly
        195                 200                 205

Gln Arg Leu Gly Val His Leu His Thr Glu Ala Arg Ala Arg His Ala
    210                 215                 220

Trp Gln Leu Thr Gln Gly Ala Thr Val Leu Gly Leu Phe Arg Val Thr
225                 230                 235                 240

Pro Glu Ile Pro Ala Gly Leu Pro Ser Pro Arg Ser Glu
                245                 250

<210> SEQ ID NO 36
<211> LENGTH: 259
<212> TYPE: PRT
```

<213> ORGANISM: Artificial Sequence
<220> FEATURE:
<223> OTHER INFORMATION: A bifunctional recombinant protein possessing
the activities of Tumstatin and CD137L (Tumstatin7-Peptide linker
8-CD137L1)

<400> SEQUENCE: 36

Thr Met Pro Phe Leu Phe Cys Asn Val Asn Asp Val Cys Asn Phe Ala
1               5                   10                  15

Ser Arg Asn Asp Tyr Ser Tyr Trp Leu Ala Glu Ala Ala Ala Lys Glu
            20                  25                  30

Ala Ala Ala Lys Glu Ala Ala Lys Glu Ala Ala Ala Lys Ala Pro
        35                  40                  45

Gly Ser Ala Val Phe Leu Ala Cys Pro Trp Ala Val Ser Gly Ala Arg
    50                  55                  60

Ala Ser Pro Gly Ser Ala Ala Ser Pro Arg Leu Arg Glu Gly Pro Glu
65                  70                  75                  80

Leu Ser Pro Asp Asp Pro Ala Gly Leu Leu Asp Leu Arg Gln Gly Met
                85                  90                  95

Phe Ala Gln Leu Val Ala Gln Asn Val Leu Leu Ile Asp Gly Pro Leu
            100                 105                 110

Ser Trp Tyr Ser Asp Pro Gly Leu Ala Gly Val Ser Leu Thr Gly Gly
        115                 120                 125

Leu Ser Tyr Lys Glu Asp Thr Lys Glu Leu Val Val Ala Lys Ala Gly
    130                 135                 140

Val Tyr Tyr Val Phe Phe Gln Leu Glu Leu Arg Arg Val Val Ala Gly
145                 150                 155                 160

Glu Gly Ser Gly Ser Val Ser Leu Ala Leu His Leu Gln Pro Leu Arg
                165                 170                 175

Ser Ala Ala Gly Ala Ala Ala Leu Ala Leu Thr Val Asp Leu Pro Pro
            180                 185                 190

Ala Ser Ser Glu Ala Arg Asn Ser Ala Phe Gly Phe Gln Gly Arg Leu
        195                 200                 205

Leu His Leu Ser Ala Gly Gln Arg Leu Gly Val His Leu His Thr Glu
    210                 215                 220

Ala Arg Ala Arg His Ala Trp Gln Leu Thr Gln Gly Ala Thr Val Leu
225                 230                 235                 240

Gly Leu Phe Arg Val Thr Pro Glu Ile Pro Ala Gly Leu Pro Ser Pro
                245                 250                 255

Arg Ser Glu

<210> SEQ ID NO 37
<211> LENGTH: 262
<212> TYPE: PRT
<213> ORGANISM: Artificial Sequence
<220> FEATURE:
<223> OTHER INFORMATION: A bifunctional recombinant protein possessing
the activities of Tumstatin and CD137L (Tumstatin2-Peptide linker
1-CD137L5)

<400> SEQUENCE: 37

Gln Asp Leu Gly Thr Leu Gly Ser Cys Leu Gln Arg Phe Thr Thr Met
1               5                   10                  15

Pro Phe Leu Phe Cys Asn Val Asn Asp Val Cys Asn Phe Ala Ser Arg
            20                  25                  30

Asn Asp Tyr Ser Tyr Trp Leu Ser Thr Pro Ala Leu Met Pro Met Asn
        35                  40                  45

```
Met Ala Pro Ile Thr Gly Arg Ala Leu Glu Pro Tyr Ile Ser Arg Cys
 50                  55                  60

Thr Val Cys Glu Gly Pro Ala Ile Ala Gly Gly Gly Ser Gly Gly
 65                  70                  75                  80

Gly Gly Ser Gly Gly Gly Gly Ser Gly Ser Gly Leu Leu Asp Leu Arg
                 85                  90                  95

Gln Gly Met Phe Ala Gln Leu Val Ala Gln Asn Val Leu Leu Ile Asp
             100                 105                 110

Gly Pro Leu Ser Trp Tyr Ser Asp Pro Gly Leu Ala Gly Val Ser Leu
         115                 120                 125

Thr Gly Leu Ser Tyr Lys Glu Asp Thr Lys Glu Leu Val Val Ala
     130                 135                 140

Lys Ala Gly Val Tyr Tyr Val Phe Phe Gln Leu Glu Leu Arg Arg Val
145                 150                 155                 160

Val Ala Gly Glu Gly Ser Gly Ser Val Ser Leu Ala Leu His Leu Gln
                 165                 170                 175

Pro Leu Arg Ser Ala Ala Gly Ala Ala Ala Leu Ala Leu Thr Val Asp
             180                 185                 190

Leu Pro Pro Ala Ser Ser Glu Ala Arg Asn Ser Ala Phe Gly Phe Gln
         195                 200                 205

Gly Arg Leu Leu His Leu Ser Ala Gly Gln Arg Leu Gly Val His Leu
     210                 215                 220

His Thr Glu Ala Arg Ala Arg His Ala Trp Gln Leu Thr Gln Gly Ala
225                 230                 235                 240

Thr Val Leu Gly Leu Phe Arg Val Thr Pro Glu Ile Pro Ala Gly Leu
                 245                 250                 255

Pro Ser Pro Arg Ser Glu
             260

<210> SEQ ID NO 38
<211> LENGTH: 269
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin2-Peptide linker
      5-CD137L5)

<400> SEQUENCE: 38

Gln Asp Leu Gly Thr Leu Gly Ser Cys Leu Gln Arg Phe Thr Thr Met
1               5                  10                  15

Pro Phe Leu Phe Cys Asn Val Asn Asp Val Cys Asn Phe Ala Ser Arg
             20                  25                  30

Asn Asp Tyr Ser Tyr Trp Leu Ser Thr Pro Ala Leu Met Pro Met Asn
         35                  40                  45

Met Ala Pro Ile Thr Gly Arg Ala Leu Glu Pro Tyr Ile Ser Arg Cys
 50                  55                  60

Thr Val Cys Glu Gly Pro Ala Ile Ala Gly Ala Ala Ala Lys Glu
 65                  70                  75                  80

Ala Ala Ala Lys Glu Ala Ala Lys Glu Ala Ala Lys Ala Gly
                 85                  90                  95

Ser Gly Leu Leu Asp Leu Arg Gln Gly Met Phe Ala Gln Leu Val Ala
             100                 105                 110

Gln Asn Val Leu Leu Ile Asp Gly Pro Leu Ser Trp Tyr Ser Asp Pro
         115                 120                 125

Gly Leu Ala Gly Val Ser Leu Thr Gly Gly Leu Ser Tyr Lys Glu Asp
```

```
         130                 135                 140
Thr Lys Glu Leu Val Val Ala Lys Ala Gly Val Tyr Tyr Val Phe Phe
145                 150                 155                 160

Gln Leu Glu Leu Arg Arg Val Val Ala Gly Glu Gly Ser Gly Ser Val
                165                 170                 175

Ser Leu Ala Leu His Leu Gln Pro Leu Arg Ser Ala Ala Gly Ala Ala
            180                 185                 190

Ala Leu Ala Leu Thr Val Asp Leu Pro Pro Ala Ser Ser Glu Ala Arg
        195                 200                 205

Asn Ser Ala Phe Gly Phe Gln Gly Arg Leu Leu His Leu Ser Ala Gly
    210                 215                 220

Gln Arg Leu Gly Val His Leu His Thr Glu Ala Arg Ala Arg His Ala
225                 230                 235                 240

Trp Gln Leu Thr Gln Gly Ala Thr Val Leu Gly Leu Phe Arg Val Thr
                245                 250                 255

Pro Glu Ile Pro Ala Gly Leu Pro Ser Pro Arg Ser Glu
                260                 265

<210> SEQ ID NO 39
<211> LENGTH: 228
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin3-Peptide linker
      1-CD137L5)

<400> SEQUENCE: 39

Gln Asp Leu Gly Thr Leu Gly Ser Cys Leu Gln Arg Phe Thr Thr Met
1               5                   10                  15

Pro Phe Leu Phe Cys Asn Val Asn Asp Val Cys Asn Phe Ala Ser Arg
                20                  25                  30

Asn Asp Tyr Ser Tyr Trp Leu Gly Gly Gly Ser Gly Gly Gly Gly
            35                  40                  45

Ser Gly Gly Gly Gly Ser Gly Ser Gly Leu Leu Asp Leu Arg Gln Gly
    50                  55                  60

Met Phe Ala Gln Leu Val Ala Gln Asn Val Leu Leu Ile Asp Gly Pro
65                  70                  75                  80

Leu Ser Trp Tyr Ser Asp Pro Gly Leu Ala Gly Val Ser Leu Thr Gly
                85                  90                  95

Gly Leu Ser Tyr Lys Glu Asp Thr Lys Glu Leu Val Val Ala Lys Ala
                100                 105                 110

Gly Val Tyr Tyr Val Phe Phe Gln Leu Glu Leu Arg Arg Val Val Ala
            115                 120                 125

Gly Glu Gly Ser Gly Ser Val Ser Leu Ala Leu His Leu Gln Pro Leu
    130                 135                 140

Arg Ser Ala Ala Gly Ala Ala Ala Leu Ala Leu Thr Val Asp Leu Pro
145                 150                 155                 160

Pro Ala Ser Ser Glu Ala Arg Asn Ser Ala Phe Gly Phe Gln Gly Arg
                165                 170                 175

Leu Leu His Leu Ser Ala Gly Gln Arg Leu Gly Val His Leu His Thr
            180                 185                 190

Glu Ala Arg Ala Arg His Ala Trp Gln Leu Thr Gln Gly Ala Thr Val
        195                 200                 205

Leu Gly Leu Phe Arg Val Thr Pro Glu Ile Pro Ala Gly Leu Pro Ser
    210                 215                 220
```

Pro Arg Ser Glu
225

<210> SEQ ID NO 40
<211> LENGTH: 235
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin3-Peptide linker
      5-CD137L5)

<400> SEQUENCE: 40

Gln Asp Leu Gly Thr Leu Gly Ser Cys Leu Gln Arg Phe Thr Thr Met
1               5                   10                  15

Pro Phe Leu Phe Cys Asn Val Asn Asp Val Cys Asn Phe Ala Ser Arg
            20                  25                  30

Asn Asp Tyr Ser Tyr Trp Leu Ala Glu Ala Ala Lys Glu Ala Ala
        35                  40                  45

Ala Lys Glu Ala Ala Ala Lys Glu Ala Ala Ala Lys Ala Gly Ser Gly
    50                  55                  60

Leu Leu Asp Leu Arg Gln Gly Met Phe Ala Gln Leu Val Ala Gln Asn
65                  70                  75                  80

Val Leu Leu Ile Asp Gly Pro Leu Ser Trp Tyr Ser Asp Pro Gly Leu
                85                  90                  95

Ala Gly Val Ser Leu Thr Gly Gly Leu Ser Tyr Lys Glu Asp Thr Lys
            100                 105                 110

Glu Leu Val Val Ala Lys Ala Gly Val Tyr Tyr Val Phe Phe Gln Leu
        115                 120                 125

Glu Leu Arg Arg Val Val Ala Gly Glu Gly Ser Gly Ser Val Ser Leu
    130                 135                 140

Ala Leu His Leu Gln Pro Leu Arg Ser Ala Ala Gly Ala Ala Ala Leu
145                 150                 155                 160

Ala Leu Thr Val Asp Leu Pro Pro Ala Ser Ser Glu Ala Arg Asn Ser
                165                 170                 175

Ala Phe Gly Phe Gln Gly Arg Leu Leu His Leu Ser Ala Gly Gln Arg
            180                 185                 190

Leu Gly Val His Leu His Thr Glu Ala Arg Ala Arg His Ala Trp Gln
        195                 200                 205

Leu Thr Gln Gly Ala Thr Val Leu Gly Leu Phe Arg Val Thr Pro Glu
    210                 215                 220

Ile Pro Ala Gly Leu Pro Ser Pro Arg Ser Glu
225                 230                 235

<210> SEQ ID NO 41
<211> LENGTH: 225
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin2-Peptide linker
      5-CD137L6)

<400> SEQUENCE: 41

Gln Asp Leu Gly Thr Leu Gly Ser Cys Leu Gln Arg Phe Thr Thr Met
1               5                   10                  15

Pro Phe Leu Phe Cys Asn Val Asn Asp Val Cys Asn Phe Ala Ser Arg
            20                  25                  30

```
Asn Asp Tyr Ser Tyr Trp Leu Ser Thr Pro Ala Leu Met Pro Met Asn
             35                  40                  45

Met Ala Pro Ile Thr Gly Arg Ala Leu Glu Pro Tyr Ile Ser Arg Cys
 50                  55                  60

Thr Val Cys Glu Gly Pro Ala Ile Ala Ala Glu Ala Ala Ala Lys Glu
 65                  70                  75                  80

Ala Ala Ala Lys Glu Ala Ala Lys Glu Ala Ala Lys Ala Gly
             85                  90                  95

Ser Ala Val Phe Leu Ala Cys Pro Trp Ala Val Ser Gly Ala Arg Ala
                100                 105                 110

Ser Pro Gly Ser Ala Ala Ser Pro Arg Leu Arg Glu Gly Pro Glu Leu
            115                 120                 125

Ser Pro Asp Asp Pro Ala Gly Leu Leu Leu Gln Pro Leu Arg Ser Ala
130                 135                 140

Ala Gly Ala Ala Ala Leu Ala Leu Thr Val Asp Leu Pro Pro Ala Ser
145                 150                 155                 160

Ser Glu Ala Arg Asn Ser Ala Phe Gly Phe Gln Gly Arg Leu Leu His
                165                 170                 175

Leu Ser Ala Gly Gln Arg Leu Gly Val His Leu His Thr Glu Ala Arg
            180                 185                 190

Ala Arg His Ala Trp Gln Leu Thr Gln Gly Ala Thr Val Leu Gly Leu
            195                 200                 205

Phe Arg Val Thr Pro Glu Ile Pro Ala Gly Leu Pro Ser Pro Arg Ser
210                 215                 220

Glu
225

<210> SEQ ID NO 42
<211> LENGTH: 191
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin3-Peptide linker
      5-CD137L6)

<400> SEQUENCE: 42

Gln Asp Leu Gly Thr Leu Gly Ser Cys Leu Gln Arg Phe Thr Thr Met
 1               5                  10                  15

Pro Phe Leu Phe Cys Asn Val Asn Asp Val Cys Asn Phe Ala Ser Arg
             20                  25                  30

Asn Asp Tyr Ser Tyr Trp Leu Ala Glu Ala Ala Ala Lys Glu Ala Ala
             35                  40                  45

Ala Lys Glu Ala Ala Lys Glu Ala Ala Lys Ala Gly Ser Ala
 50                  55                  60

Val Phe Leu Ala Cys Pro Trp Ala Val Ser Gly Ala Arg Ala Ser Pro
 65                  70                  75                  80

Gly Ser Ala Ala Ser Pro Arg Leu Arg Glu Gly Pro Glu Leu Ser Pro
             85                  90                  95

Asp Asp Pro Ala Gly Leu Leu Leu Gln Pro Leu Arg Ser Ala Ala Gly
                100                 105                 110

Ala Ala Ala Leu Ala Leu Thr Val Asp Leu Pro Pro Ala Ser Ser Glu
            115                 120                 125

Ala Arg Asn Ser Ala Phe Gly Phe Gln Gly Arg Leu Leu His Leu Ser
130                 135                 140

Ala Gly Gln Arg Leu Gly Val His Leu His Thr Glu Ala Arg Ala Arg
```

```
145                 150                 155                 160
His Ala Trp Gln Leu Thr Gln Gly Ala Thr Val Leu Gly Leu Phe Arg
                165                 170                 175
Val Thr Pro Glu Ile Pro Ala Gly Leu Pro Ser Pro Arg Ser Glu
                180                 185                 190

<210> SEQ ID NO 43
<211> LENGTH: 263
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin1-Peptide linker
      1-CD137L4)

<400> SEQUENCE: 43

Met Gly Phe Ser Phe Leu Phe Val Gln Gly Asn Gln Arg Ala His Gly
1               5                   10                  15
Gln Asp Leu Gly Thr Leu Gly Ser Cys Leu Gln Arg Phe Thr Thr Met
                20                  25                  30
Pro Phe Leu Phe Cys Asn Val Asn Asp Val Cys Asn Phe Ala Ser Arg
            35                  40                  45
Asn Asp Tyr Ser Tyr Trp Leu Gly Gly Gly Ser Gly Gly Gly Gly
        50                  55                  60
Ser Gly Gly Gly Ser Gly Ser Ala Cys Pro Trp Ala Val Ser Gly
65                  70                  75                  80
Ala Arg Ala Ser Pro Gly Ser Ala Ala Ser Pro Arg Leu Arg Glu Gly
                85                  90                  95
Pro Glu Leu Ser Pro Asp Asp Pro Ala Gly Leu Leu Asp Leu Arg Gln
                100                 105                 110
Gly Met Phe Ala Gln Leu Val Ala Gln Asn Val Leu Leu Ile Asp Gly
            115                 120                 125
Pro Leu Ser Trp Tyr Ser Asp Pro Gly Leu Ala Gly Val Ser Leu Thr
        130                 135                 140
Gly Gly Leu Ser Tyr Lys Glu Asp Thr Lys Glu Leu Val Val Ala Lys
145                 150                 155                 160
Ala Gly Val Tyr Tyr Val Phe Phe Gln Leu Glu Leu Arg Arg Val Val
                165                 170                 175
Ala Gly Glu Gly Ser Gly Ser Val Ser Leu Ala Leu His Leu Gln Pro
                180                 185                 190
Leu Arg Ser Ala Ala Gly Ala Ala Ala Leu Ala Leu Thr Val Asp Leu
            195                 200                 205
Pro Pro Ala Ser Ser Glu Ala Arg Asn Ser Ala Phe Gly Phe Gln Gly
        210                 215                 220
Arg Leu Leu His Leu Ser Ala Gly Gln Arg Leu Gly Val His Leu His
225                 230                 235                 240
Thr Glu Ala Arg Ala Arg His Ala Trp Gln Leu Thr Gln Gly Ala Thr
                245                 250                 255
Val Leu Gly Leu Phe Arg Val
                260

<210> SEQ ID NO 44
<211> LENGTH: 282
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin2-Peptide linker
```

1-CD137L4)

<400> SEQUENCE: 44

```
Met Gln Asp Leu Gly Thr Leu Gly Ser Cys Leu Gln Arg Phe Thr Thr
1               5                   10                  15
Met Pro Phe Leu Phe Cys Asn Val Asn Asp Val Cys Asn Phe Ala Ser
            20                  25                  30
Arg Asn Asp Tyr Ser Tyr Trp Leu Ser Thr Pro Ala Leu Met Pro Met
        35                  40                  45
Asn Met Ala Pro Ile Thr Gly Arg Ala Leu Glu Pro Tyr Ile Ser Arg
    50                  55                  60
Cys Thr Val Cys Glu Gly Pro Ala Ile Ala Gly Gly Gly Ser Gly
65                  70                  75                  80
Gly Gly Gly Ser Gly Gly Gly Ser Gly Ser Ala Cys Pro Trp Ala
                85                  90                  95
Val Ser Gly Ala Arg Ala Ser Pro Gly Ser Ala Ala Ser Pro Arg Leu
            100                 105                 110
Arg Glu Gly Pro Glu Leu Ser Pro Asp Asp Pro Ala Gly Leu Leu Asp
        115                 120                 125
Leu Arg Gln Gly Met Phe Ala Gln Leu Val Ala Gln Asn Val Leu Leu
    130                 135                 140
Ile Asp Gly Pro Leu Ser Trp Tyr Ser Asp Pro Gly Leu Ala Gly Val
145                 150                 155                 160
Ser Leu Thr Gly Gly Leu Ser Tyr Lys Glu Asp Thr Lys Glu Leu Val
                165                 170                 175
Val Ala Lys Ala Gly Val Tyr Tyr Val Phe Phe Gln Leu Glu Leu Arg
            180                 185                 190
Arg Val Val Ala Gly Glu Gly Ser Gly Ser Val Ser Leu Ala Leu His
        195                 200                 205
Leu Gln Pro Leu Arg Ser Ala Ala Gly Ala Ala Ala Leu Ala Leu Thr
    210                 215                 220
Val Asp Leu Pro Pro Ala Ser Ser Glu Ala Arg Asn Ser Ala Phe Gly
225                 230                 235                 240
Phe Gln Gly Arg Leu Leu His Leu Ser Ala Gly Gln Arg Leu Gly Val
                245                 250                 255
His Leu His Thr Glu Ala Arg Ala Arg His Ala Trp Gln Leu Thr Gln
            260                 265                 270
Gly Ala Thr Val Leu Gly Leu Phe Arg Val
        275                 280
```

<210> SEQ ID NO 45
<211> LENGTH: 248
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin3-Peptide linker
      1-CD137L4)

<400> SEQUENCE: 45

```
Met Gln Asp Leu Gly Thr Leu Gly Ser Cys Leu Gln Arg Phe Thr Thr
1               5                   10                  15
Met Pro Phe Leu Phe Cys Asn Val Asn Asp Val Cys Asn Phe Ala Ser
            20                  25                  30
Arg Asn Asp Tyr Ser Tyr Trp Leu Gly Gly Gly Ser Gly Gly Gly
        35                  40                  45
```

-continued

```
Gly Ser Gly Gly Gly Ser Gly Ala Cys Pro Trp Ala Val Ser
    50              55                  60
Gly Ala Arg Ala Ser Pro Gly Ser Ala Ala Ser Pro Arg Leu Arg Glu
65              70                  75                  80
Gly Pro Glu Leu Ser Pro Asp Asp Pro Ala Gly Leu Leu Asp Leu Arg
                85                  90                  95
Gln Gly Met Phe Ala Gln Leu Val Ala Gln Asn Val Leu Leu Ile Asp
            100                 105                 110
Gly Pro Leu Ser Trp Tyr Ser Asp Pro Gly Leu Ala Gly Val Ser Leu
            115                 120                 125
Thr Gly Leu Ser Tyr Lys Glu Asp Thr Lys Glu Leu Val Val Ala
130                 135                 140
Lys Ala Gly Val Tyr Tyr Val Phe Phe Gln Leu Glu Leu Arg Arg Val
145                 150                 155                 160
Val Ala Gly Glu Gly Ser Gly Ser Val Ser Leu Ala Leu His Leu Gln
                165                 170                 175
Pro Leu Arg Ser Ala Ala Gly Ala Ala Ala Leu Ala Leu Thr Val Asp
            180                 185                 190
Leu Pro Pro Ala Ser Ser Glu Ala Arg Asn Ser Ala Phe Gly Phe Gln
            195                 200                 205
Gly Arg Leu Leu His Leu Ser Ala Gly Gln Arg Leu Gly Val His Leu
210                 215                 220
His Thr Glu Ala Arg Ala Arg His Ala Trp Gln Leu Thr Gln Gly Ala
225                 230                 235                 240
Thr Val Leu Gly Leu Phe Arg Val
                245

<210> SEQ ID NO 46
<211> LENGTH: 270
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin1-Peptide linker
      5-CD137L4)

<400> SEQUENCE: 46

Met Gly Phe Ser Phe Leu Phe Val Gln Gly Asn Gln Arg Ala His Gly
1               5                   10                  15
Gln Asp Leu Gly Thr Leu Gly Ser Cys Leu Gln Arg Phe Thr Thr Met
            20                  25                  30
Pro Phe Leu Phe Cys Asn Val Asn Asp Val Cys Asn Phe Ala Ser Arg
        35                  40                  45
Asn Asp Tyr Ser Tyr Trp Leu Ala Glu Ala Ala Ala Lys Glu Ala Ala
    50                  55                  60
Ala Lys Glu Ala Ala Ala Lys Glu Ala Ala Ala Lys Ala Gly Ser Ala
65                  70                  75                  80
Cys Pro Trp Ala Val Ser Gly Ala Arg Ala Ser Pro Gly Ser Ala Ala
                85                  90                  95
Ser Pro Arg Leu Arg Glu Gly Pro Glu Leu Ser Pro Asp Asp Pro Ala
            100                 105                 110
Gly Leu Leu Asp Leu Arg Gln Gly Met Phe Ala Gln Leu Val Ala Gln
            115                 120                 125
Asn Val Leu Leu Ile Asp Gly Pro Leu Ser Trp Tyr Ser Asp Pro Gly
        130                 135                 140
Leu Ala Gly Val Ser Leu Thr Gly Gly Leu Ser Tyr Lys Glu Asp Thr
```

145                 150                 155                 160
Lys Glu Leu Val Val Ala Lys Ala Gly Val Tyr Tyr Val Phe Phe Gln
                165                 170                 175

Leu Glu Leu Arg Arg Val Val Ala Gly Glu Gly Ser Gly Ser Val Ser
            180                 185                 190

Leu Ala Leu His Leu Gln Pro Leu Arg Ser Ala Ala Gly Ala Ala Ala
        195                 200                 205

Leu Ala Leu Thr Val Asp Leu Pro Pro Ala Ser Ser Glu Ala Arg Asn
    210                 215                 220

Ser Ala Phe Gly Phe Gln Gly Arg Leu Leu His Leu Ser Ala Gly Gln
225                 230                 235                 240

Arg Leu Gly Val His Leu His Thr Glu Ala Arg Ala Arg His Ala Trp
                245                 250                 255

Gln Leu Thr Gln Gly Ala Thr Val Leu Gly Leu Phe Arg Val
            260                 265                 270

<210> SEQ ID NO 47
<211> LENGTH: 289
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin2-Peptide linker
      5-CD137L4)

<400> SEQUENCE: 47

Met Gln Asp Leu Gly Thr Leu Gly Ser Cys Leu Gln Arg Phe Thr Thr
1               5                   10                  15

Met Pro Phe Leu Phe Cys Asn Val Asn Asp Val Cys Asn Phe Ala Ser
                20                  25                  30

Arg Asn Asp Tyr Ser Tyr Trp Leu Ser Thr Pro Ala Leu Met Pro Met
            35                  40                  45

Asn Met Ala Pro Ile Thr Gly Arg Ala Leu Glu Pro Tyr Ile Ser Arg
        50                  55                  60

Cys Thr Val Cys Glu Gly Pro Ala Ile Ala Ala Glu Ala Ala Ala Lys
65                  70                  75                  80

Glu Ala Ala Ala Lys Glu Ala Ala Ala Lys Glu Ala Ala Ala Lys Ala
                85                  90                  95

Gly Ser Ala Cys Pro Trp Ala Val Ser Gly Ala Arg Ala Ser Pro Gly
            100                 105                 110

Ser Ala Ala Ser Pro Arg Leu Arg Glu Gly Pro Glu Leu Ser Pro Asp
        115                 120                 125

Asp Pro Ala Gly Leu Leu Asp Leu Arg Gln Gly Met Phe Ala Gln Leu
    130                 135                 140

Val Ala Gln Asn Val Leu Leu Ile Asp Gly Pro Leu Ser Trp Tyr Ser
145                 150                 155                 160

Asp Pro Gly Leu Ala Gly Val Ser Leu Thr Gly Gly Leu Ser Tyr Lys
                165                 170                 175

Glu Asp Thr Lys Glu Leu Val Val Ala Lys Ala Gly Val Tyr Tyr Val
            180                 185                 190

Phe Phe Gln Leu Glu Leu Arg Arg Val Val Ala Gly Glu Gly Ser Gly
        195                 200                 205

Ser Val Ser Leu Ala Leu His Leu Gln Pro Leu Arg Ser Ala Ala Gly
    210                 215                 220

Ala Ala Ala Leu Ala Leu Thr Val Asp Leu Pro Pro Ala Ser Ser Glu
225                 230                 235                 240

Ala Arg Asn Ser Ala Phe Gly Phe Gln Gly Arg Leu Leu His Leu Ser
            245                 250                 255

Ala Gly Gln Arg Leu Gly Val His Leu His Thr Glu Ala Arg Ala Arg
            260                 265                 270

His Ala Trp Gln Leu Thr Gln Gly Ala Thr Val Leu Gly Leu Phe Arg
            275                 280                 285

Val

<210> SEQ ID NO 48
<211> LENGTH: 255
<212> TYPE: PRT
<213> ORGANISM: Artificial Sequence
<220> FEATURE:
<223> OTHER INFORMATION: A bifunctional recombinant protein possessing
      the activities of Tumstatin and CD137L (Tumstatin3-Peptide linker
      5-CD137L4)

<400> SEQUENCE: 48

Met Gln Asp Leu Gly Thr Leu Gly Ser Cys Leu Gln Arg Phe Thr Thr
1               5                   10                  15

Met Pro Phe Leu Phe Cys Asn Val Asn Asp Val Cys Asn Phe Ala Ser
            20                  25                  30

Arg Asn Asp Tyr Ser Tyr Trp Leu Ala Glu Ala Ala Ala Lys Glu Ala
            35                  40                  45

Ala Ala Lys Glu Ala Ala Ala Lys Glu Ala Ala Ala Lys Ala Gly Ser
        50                  55                  60

Ala Cys Pro Trp Ala Val Ser Gly Ala Arg Ala Ser Pro Gly Ser Ala
65              70                  75                  80

Ala Ser Pro Arg Leu Arg Glu Gly Pro Glu Leu Ser Pro Asp Asp Pro
                85                  90                  95

Ala Gly Leu Leu Asp Leu Arg Gln Gly Met Phe Ala Gln Leu Val Ala
            100                 105                 110

Gln Asn Val Leu Leu Ile Asp Gly Pro Leu Ser Trp Tyr Ser Asp Pro
            115                 120                 125

Gly Leu Ala Gly Val Ser Leu Thr Gly Gly Leu Ser Tyr Lys Glu Asp
        130                 135                 140

Thr Lys Glu Leu Val Val Ala Lys Ala Gly Val Tyr Tyr Val Phe Phe
145             150                 155                 160

Gln Leu Glu Leu Arg Arg Val Val Ala Gly Glu Gly Ser Gly Ser Val
                165                 170                 175

Ser Leu Ala Leu His Leu Gln Pro Leu Arg Ser Ala Ala Gly Ala Ala
            180                 185                 190

Ala Leu Ala Leu Thr Val Asp Leu Pro Pro Ala Ser Ser Glu Ala Arg
            195                 200                 205

Asn Ser Ala Phe Gly Phe Gln Gly Arg Leu Leu His Leu Ser Ala Gly
        210                 215                 220

Gln Arg Leu Gly Val His Leu His Thr Glu Ala Arg Ala Arg His Ala
225             230                 235                 240

Trp Gln Leu Thr Gln Gly Ala Thr Val Leu Gly Leu Phe Arg Val
                245                 250                 255

<210> SEQ ID NO 49
<211> LENGTH: 162
<212> TYPE: DNA
<213> ORGANISM: Artificial Sequence
<220> FEATURE:
<223> OTHER INFORMATION: Tumstatin1

```
<400> SEQUENCE: 49 ggttttctt tcttatttgt tcaaggcaat cagcgtgctc atggacaaga tttggggact        60
cttggttcct gtctccagcg cttcaccaca atgccttttc tattctgcaa cgtcaatgac       120
gtatgtaact ttgcctcacg aaatgattat tcgtactggc tg                          162

<210> SEQ ID NO 50
<211> LENGTH: 219
<212> TYPE: DNA
<213> ORGANISM: Artificial Sequence
<220> FEATURE:
<223> OTHER INFORMATION: Tumstatin2

<400> SEQUENCE: 50
caagatttag gtactttggg ctcttgtctt cagcgtttta ccacaatgcc tttcctcttt        60
tgcaatgtta acgacgtctg taatttcgct tcccgcaacg attattcata ctggctatcg      120
acgcccgccc tgatgccaat gaatatggca ccgattactg gacgagcgtt agaaccttat      180
atcagtcggt gcaccgtatg tgaggggccc gctatagcc                              219

<210> SEQ ID NO 51
<211> LENGTH: 117
<212> TYPE: DNA
<213> ORGANISM: Artificial Sequence
<220> FEATURE:
<223> OTHER INFORMATION: Tumstatin3

<400> SEQUENCE: 51
caagatttag gtactttggg ctcttgtctt cagcgtttta ccacaatgcc tttcctcttt        60
tgcaatgtta acgacgtctg taatttcgct tcccgcaacg attattcata ctggcta         117

<210> SEQ ID NO 52
<211> LENGTH: 75
<212> TYPE: DNA
<213> ORGANISM: Artificial Sequence
<220> FEATURE:
<223> OTHER INFORMATION: Tumstatin7

<400> SEQUENCE: 52
acaatgccat tcttattctg caatgtcaat gatgtatgta attttgcatc tcgtaatgat        60
tattcatact ggctg                                                         75

<210> SEQ ID NO 53
<211> LENGTH: 45
<212> TYPE: DNA
<213> ORGANISM: Artificial Sequence
<220> FEATURE:
<223> OTHER INFORMATION: Peptide linker 1

<400> SEQUENCE: 53
ggaggtggtg gatcaggtgg aggtggatct ggtggaggtg gaagt                        45

<210> SEQ ID NO 54
<211> LENGTH: 51
<212> TYPE: DNA
<213> ORGANISM: Artificial Sequence
<220> FEATURE:
<223> OTHER INFORMATION: Peptide linker 2

<400> SEQUENCE: 54
ggaggtggtg gatcaggtgg aggtggatct ggtggaggtg gatctggtgg a                 51
```

<210> SEQ ID NO 55
<211> LENGTH: 27
<212> TYPE: DNA
<213> ORGANISM: Artificial Sequence
<220> FEATURE:
<223> OTHER INFORMATION: Peptide linker 3

<400> SEQUENCE: 55
ggaggtggtg gatcaggtgg aggtcct                                         27

<210> SEQ ID NO 56
<211> LENGTH: 42
<212> TYPE: DNA
<213> ORGANISM: Artificial Sequence
<220> FEATURE:
<223> OTHER INFORMATION: Peptide linker 4

<400> SEQUENCE: 56
ggaggtggtg gatcaggtgg aggtcctgga tcaggtggag gt                        42

<210> SEQ ID NO 57
<211> LENGTH: 66
<212> TYPE: DNA
<213> ORGANISM: Artificial Sequence
<220> FEATURE:
<223> OTHER INFORMATION: Peptide linker 5

<400> SEQUENCE: 57
gctgaagctg ctgccaaaga agccgctgct aaggaagcag ctgccaagga agccgctgcc     60
aaggcc                                                                66

<210> SEQ ID NO 58
<211> LENGTH: 81
<212> TYPE: DNA
<213> ORGANISM: Artificial Sequence
<220> FEATURE:
<223> OTHER INFORMATION: Peptide linker 6

<400> SEQUENCE: 58
gctgaagctg ctgccaaaga agccgctgct aaggaagcag ctgccaagga agccgctgcc     60
aaggccgctg cagccaaggc t                                               81

<210> SEQ ID NO 59
<211> LENGTH: 51
<212> TYPE: DNA
<213> ORGANISM: Artificial Sequence
<220> FEATURE:
<223> OTHER INFORMATION: Peptide linker 7

<400> SEQUENCE: 59
gctgaagctg ctgccaaaga agccgctgct aaggaagcag ctgccaaggc t              51

<210> SEQ ID NO 60
<211> LENGTH: 69
<212> TYPE: DNA
<213> ORGANISM: Artificial Sequence
<220> FEATURE:
<223> OTHER INFORMATION: Peptide linker 8

<400> SEQUENCE: 60
gctgaagctg ctgccaaaga agccgctgct aaggaagcag ctgccaagga agccgctgcc     60
aaggcccct                                                             69

<210> SEQ ID NO 61
<211> LENGTH: 627
<212> TYPE: DNA
<213> ORGANISM: Artificial Sequence
<220> FEATURE:
<223> OTHER INFORMATION: CD137L1

<400> SEQUENCE: 61

| | |
|---|---|
| gccgtcttcc tcgcctgccc ctgggccgtg tccggggctc gcgcctcgcc cggctccgcg | 60 |
| gccagcccga gactccgcga gggtcccgag ctttcgcccg acgatcccgc cggcctcttg | 120 |
| gacctgcggc agggcatgtt tgcgcagctg gtggcccaaa atgttctgct gatcgatggg | 180 |
| cccctgagct ggtacagtga cccaggcctg caggcgtgt ccctgacggg gggcctgagc | 240 |
| tacaaagagg acacgaagga gctggtggtg gccaaggctg gagtctacta tgtcttcttt | 300 |
| caactagagc tgcggcgcgt ggtggccggc gagggctcag gctccgtttc acttgcgctg | 360 |
| cacctgcagc cactgcgctc tgctgctggg gccgccgccc tggctttgac cgtggacctg | 420 |
| ccacccgcct cctccgaggc tcggaactcg gccttcggtt tccagggccg cttgctgcac | 480 |
| ctgagtgccg ccagcgcct gggcgtccat cttcacactg aggccagggc acgccatgcc | 540 |
| tggcagctta cccagggcgc cacagtcttg gactcttcc gggtgacccc cgaaatccca | 600 |
| gccggactcc cttcaccgag gtcggaa | 627 |

<210> SEQ ID NO 62
<211> LENGTH: 516
<212> TYPE: DNA
<213> ORGANISM: Artificial Sequence
<220> FEATURE:
<223> OTHER INFORMATION: CD137L5

<400> SEQUENCE: 62

| | |
|---|---|
| ggcctcttgg acctgcggca gggcatgttt gcgcagctgg tggcccaaaa tgttctgctg | 60 |
| atcgatgggc ccctgagctg gtacagtgac ccaggcctgg caggcgtgtc cctgacgggg | 120 |
| ggcctgagct acaaagagga cacgaaggag ctggtggtgg ccaaggctgg agtctactat | 180 |
| gtcttctttc aactagagct gcggcgcgt gtggccggcg agggctcagg ctccgtttca | 240 |
| cttgcgctgc acctgcagcc actgcgctct gctgctgggg ccgccgccct ggctttgacc | 300 |
| gtggacctgc cacccgcctc ctccgaggct cggaactcgg ccttcggttt ccagggccgc | 360 |
| ttgctgcacc tgagtgccgg ccagcgcctg ggcgtccatc ttcacactga ggccagggca | 420 |
| cgccatgcct ggcagcttac ccagggcgcc acagtcttgg actcttccg ggtgaccccc | 480 |
| gaaatcccag ccggactccc ttcaccgagg tcggaa | 516 |

<210> SEQ ID NO 63
<211> LENGTH: 384
<212> TYPE: DNA
<213> ORGANISM: Artificial Sequence
<220> FEATURE:
<223> OTHER INFORMATION: CD137L6

<400> SEQUENCE: 63

| | |
|---|---|
| gccgtcttcc tcgcctgccc ctgggccgtg tccggggctc gcgcctcgcc cggctccgcg | 60 |
| gccagcccga gactccgcga gggtcccgag ctttcgcccg acgatcccgc cggcctcttg | 120 |
| ctgcagccac tgcgctctgc tgctggggcc gccgcctgg cttttgaccgt ggacctgcca | 180 |
| cccgcctcct ccgaggctcg gaactcggcc ttcggtttcc agggccgctt gctgcacctg | 240 |
| agtgccggcc agcgcctggg cgtccatctt cacactgagg ccagggcacg ccatgcctgg | 300 |

```
cagcttaccc agggcgccac agtcttggga ctcttccggg tgaccccga aatcccagcc    360 ggactcccctt caccgaggtc ggaa                                         384
```

<210> SEQ ID NO 64
<211> LENGTH: 573
<212> TYPE: DNA
<213> ORGANISM: Artificial Sequence
<220> FEATURE:
<223> OTHER INFORMATION: CD137L4

<400> SEQUENCE: 64

```
gcctgcccct gggccgtgtc cggggctcgc gcctcgcccg gctccgcggc cagcccgaga     60
ctccgcgagg gtcccgagct ttcgcccgac gatcccgccg gcctcttgga cctgcggcag    120
ggcatgtttg cgcagctggt ggcccaaaat gttctgctga tcgatgggcc cctgagctgg    180
tacagtgacc caggcctggc aggcgtgtcc ctgacggggg gcctgagcta caaagaggac    240
acgaaggagc tggtggtggc caaggctgga gtctactatg tcttctttca actagagctg    300
cggcgcgtgg tggccggcga gggctcaggc tccgtttcac ttgcgctgca cctgcagcca    360
ctgcgctctg ctgctggggc cgccgccctg gctttgaccg tggacctgcc acccgcctcc    420
tccgaggctc ggaactcggc cttcggtttc cagggccgct tgctgcacct gagtgccggc    480
cagcgcctgg gcgtccatct tcacactgag gccagggcac gccatgcctg cagcttacc    540 cagggcgcca cagtcttggg actcttccgg gtg                                 573
```

<210> SEQ ID NO 65
<211> LENGTH: 54
<212> TYPE: PRT
<213> ORGANISM: Artificial Sequence
<220> FEATURE:
<223> OTHER INFORMATION: Tumstatin1

<400> SEQUENCE: 65

Gly Phe Ser Phe Leu Phe Val Gln Gly Asn Gln Arg Ala His Gly Gln
1               5                   10                  15

Asp Leu Gly Thr Leu Gly Ser Cys Leu Gln Arg Phe Thr Thr Met Pro
            20                  25                  30

Phe Leu Phe Cys Asn Val Asn Asp Val Cys Asn Phe Ala Ser Arg Asn
        35                  40                  45

Asp Tyr Ser Tyr Trp Leu
    50

<210> SEQ ID NO 66
<211> LENGTH: 73
<212> TYPE: PRT
<213> ORGANISM: Artificial Sequence
<220> FEATURE:
<223> OTHER INFORMATION: Tumstatin2

<400> SEQUENCE: 66

Gln Asp Leu Gly Thr Leu Gly Ser Cys Leu Gln Arg Phe Thr Thr Met
1               5                   10                  15

Pro Phe Leu Phe Cys Asn Val Asn Asp Val Cys Asn Phe Ala Ser Arg
            20                  25                  30

Asn Asp Tyr Ser Tyr Trp Leu Ser Thr Pro Ala Leu Met Pro Met Asn
        35                  40                  45

Met Ala Pro Ile Thr Gly Arg Ala Leu Glu Pro Tyr Ile Ser Arg Cys
    50                  55                  60

Thr Val Cys Glu Gly Pro Ala Ile Ala

-continued

```
<210> SEQ ID NO 67
<211> LENGTH: 39
<212> TYPE: PRT
<213> ORGANISM: Artificial Sequence
<220> FEATURE:
<223> OTHER INFORMATION: Tumstatin3

<400> SEQUENCE: 67

Gln Asp Leu Gly Thr Leu Gly Ser Cys Leu Gln Arg Phe Thr Thr Met
1               5                   10                  15

Pro Phe Leu Phe Cys Asn Val Asn Asp Val Cys Asn Phe Ala Ser Arg
            20                  25                  30

Asn Asp Tyr Ser Tyr Trp Leu
        35

<210> SEQ ID NO 68
<211> LENGTH: 25
<212> TYPE: PRT
<213> ORGANISM: Artificial Sequence
<220> FEATURE:
<223> OTHER INFORMATION: Tumstatin7

<400> SEQUENCE: 68

Thr Met Pro Phe Leu Phe Cys Asn Val Asn Asp Val Cys Asn Phe Ala
1               5                   10                  15

Ser Arg Asn Asp Tyr Ser Tyr Trp Leu
            20                  25

<210> SEQ ID NO 69
<211> LENGTH: 15
<212> TYPE: PRT
<213> ORGANISM: Artificial Sequence
<220> FEATURE:
<223> OTHER INFORMATION: Peptide linker 1

<400> SEQUENCE: 69

Gly Gly Gly Gly Ser Gly Gly Gly Gly Ser Gly Gly Gly Gly Ser
1               5                   10                  15

<210> SEQ ID NO 70
<211> LENGTH: 17
<212> TYPE: PRT
<213> ORGANISM: Artificial Sequence
<220> FEATURE:
<223> OTHER INFORMATION: Peptide linker 2

<400> SEQUENCE: 70

Gly Gly Gly Gly Ser Gly Gly Gly Gly Ser Gly Gly Gly Gly Ser Gly
1               5                   10                  15

Gly

<210> SEQ ID NO 71
<211> LENGTH: 9
<212> TYPE: PRT
<213> ORGANISM: Artificial Sequence
<220> FEATURE:
<223> OTHER INFORMATION: Peptide linker 3

<400> SEQUENCE: 71

Gly Gly Gly Gly Ser Gly Gly Gly Pro
1               5
```

<210> SEQ ID NO 72
<211> LENGTH: 14
<212> TYPE: PRT
<213> ORGANISM: Artificial Sequence
<220> FEATURE:
<223> OTHER INFORMATION: Peptide linker 4

<400> SEQUENCE: 72

Gly Gly Gly Gly Ser Gly Gly Gly Pro Gly Ser Gly Gly Gly
1               5                   10

<210> SEQ ID NO 73
<211> LENGTH: 22
<212> TYPE: PRT
<213> ORGANISM: Artificial Sequence
<220> FEATURE:
<223> OTHER INFORMATION: Peptide linker 5

<400> SEQUENCE: 73

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 74
<211> LENGTH: 27
<212> TYPE: PRT
<213> ORGANISM: Artificial Sequence
<220> FEATURE:
<223> OTHER INFORMATION: Peptide linker 6

<400> SEQUENCE: 74

Ala Glu Ala Ala Ala Lys Glu Ala Ala Ala Lys Glu Ala Ala Ala Lys
1               5                   10                  15

Glu Ala Ala Ala Lys Ala Ala Ala Ala Lys Ala
            20                  25

<210> SEQ ID NO 75
<211> LENGTH: 17
<212> TYPE: PRT
<213> ORGANISM: Artificial Sequence
<220> FEATURE:
<223> OTHER INFORMATION: Peptide Linker 7

<400> SEQUENCE: 75

Ala Glu Ala Ala Ala Lys Glu Ala Ala Ala Lys Glu Ala Ala Ala Lys
1               5                   10                  15

Ala

<210> SEQ ID NO 76
<211> LENGTH: 23
<212> TYPE: PRT
<213> ORGANISM: Artificial Sequence
<220> FEATURE:
<223> OTHER INFORMATION: Peptide linker 8

<400> SEQUENCE: 76

Ala Glu Ala Ala Ala Lys Glu Ala Ala Ala Lys Glu Ala Ala Ala Lys
1               5                   10                  15

Glu Ala Ala Ala Lys Ala Pro
            20

<210> SEQ ID NO 77
<211> LENGTH: 209
<212> TYPE: PRT

<213> ORGANISM: Artificial Sequence
<220> FEATURE:
<223> OTHER INFORMATION: CD137L1

<400> SEQUENCE: 77

Ala Val Phe Leu Ala Cys Pro Trp Ala Val Ser Gly Ala Arg Ala Ser
1               5                   10                  15

Pro Gly Ser Ala Ala Ser Pro Arg Leu Arg Glu Gly Pro Glu Leu Ser
            20                  25                  30

Pro Asp Asp Pro Ala Gly Leu Leu Asp Leu Arg Gln Gly Met Phe Ala
        35                  40                  45

Gln Leu Val Ala Gln Asn Val Leu Leu Ile Asp Gly Pro Leu Ser Trp
50                  55                  60

Tyr Ser Asp Pro Gly Leu Ala Gly Val Ser Leu Thr Gly Gly Leu Ser
65                  70                  75                  80

Tyr Lys Glu Asp Thr Lys Glu Leu Val Val Ala Lys Ala Gly Val Tyr
                85                  90                  95

Tyr Val Phe Phe Gln Leu Glu Leu Arg Arg Val Val Ala Gly Glu Gly
            100                 105                 110

Ser Gly Ser Val Ser Leu Ala Leu His Leu Gln Pro Leu Arg Ser Ala
        115                 120                 125

Ala Gly Ala Ala Ala Leu Ala Leu Thr Val Asp Leu Pro Pro Ala Ser
    130                 135                 140

Ser Glu Ala Arg Asn Ser Ala Phe Gly Phe Gln Gly Arg Leu Leu His
145                 150                 155                 160

Leu Ser Ala Gly Gln Arg Leu Gly Val His Leu His Thr Glu Ala Arg
                165                 170                 175

Ala Arg His Ala Trp Gln Leu Thr Gln Gly Ala Thr Val Leu Gly Leu
            180                 185                 190

Phe Arg Val Thr Pro Glu Ile Pro Ala Gly Leu Pro Ser Pro Arg Ser
        195                 200                 205

Glu

<210> SEQ ID NO 78
<211> LENGTH: 172
<212> TYPE: PRT
<213> ORGANISM: Artificial Sequence
<220> FEATURE:
<223> OTHER INFORMATION: CD137L5

<400> SEQUENCE: 78

Gly Leu Leu Asp Leu Arg Gln Gly Met Phe Ala Gln Leu Val Ala Gln
1               5                   10                  15

Asn Val Leu Leu Ile Asp Gly Pro Leu Ser Trp Tyr Ser Asp Pro Gly
            20                  25                  30

Leu Ala Gly Val Ser Leu Thr Gly Gly Leu Ser Tyr Lys Glu Asp Thr
        35                  40                  45

Lys Glu Leu Val Val Ala Lys Ala Gly Val Tyr Tyr Val Phe Phe Gln
50                  55                  60

Leu Glu Leu Arg Arg Val Val Ala Gly Glu Gly Ser Gly Ser Val Ser
65                  70                  75                  80

Leu Ala Leu His Leu Gln Pro Leu Arg Ser Ala Ala Gly Ala Ala Ala
                85                  90                  95

Leu Ala Leu Thr Val Asp Leu Pro Pro Ala Ser Ser Glu Ala Arg Asn
            100                 105                 110

Ser Ala Phe Gly Phe Gln Gly Arg Leu Leu His Leu Ser Ala Gly Gln

```
            115                 120                 125
Arg Leu Gly Val His Leu His Thr Glu Ala Arg Ala Arg His Ala Trp
    130                 135                 140

Gln Leu Thr Gln Gly Ala Thr Val Leu Gly Leu Phe Arg Val Thr Pro
145                 150                 155                 160

Glu Ile Pro Ala Gly Leu Pro Ser Pro Arg Ser Glu
                165                 170
```

<210> SEQ ID NO 79
<211> LENGTH: 128
<212> TYPE: PRT
<213> ORGANISM: Artificial Sequence
<220> FEATURE:
<223> OTHER INFORMATION: CD137L6

<400> SEQUENCE: 79

```
Ala Val Phe Leu Ala Cys Pro Trp Ala Val Ser Gly Ala Arg Ala Ser
1               5                   10                  15

Pro Gly Ser Ala Ala Ser Pro Arg Leu Arg Glu Gly Pro Glu Leu Ser
                20                  25                  30

Pro Asp Asp Pro Ala Gly Leu Leu Leu Gln Pro Leu Arg Ser Ala Ala
            35                  40                  45

Gly Ala Ala Ala Leu Ala Leu Thr Val Asp Leu Pro Pro Ala Ser Ser
        50                  55                  60

Glu Ala Arg Asn Ser Ala Phe Gly Phe Gln Gly Arg Leu Leu His Leu
65                  70                  75                  80

Ser Ala Gly Gln Arg Leu Gly Val His Leu His Thr Glu Ala Arg Ala
                85                  90                  95

Arg His Ala Trp Gln Leu Thr Gln Gly Ala Thr Val Leu Gly Leu Phe
            100                 105                 110

Arg Val Thr Pro Glu Ile Pro Ala Gly Leu Pro Ser Pro Arg Ser Glu
        115                 120                 125
```

<210> SEQ ID NO 80
<211> LENGTH: 197
<212> TYPE: PRT
<213> ORGANISM: Artificial Sequence
<220> FEATURE:
<223> OTHER INFORMATION: CD137L4

<400> SEQUENCE: 80

```
Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
                20                  25                  30

Ala Gly Leu Leu Asp Leu Arg Gln Gly Met Phe Ala Gln Leu Val Ala
            35                  40                  45

Gln Asn Val Leu Leu Ile Asp Gly Pro Leu Ser Trp Tyr Ser Asp Pro
        50                  55                  60

Gly Leu Ala Gly Val Ser Leu Thr Gly Gly Leu Ser Tyr Lys Glu Gly
65                  70                  75                  80

Gly Leu Ser Tyr Lys Glu Asp Thr Lys Glu Leu Val Val Ala Lys Ala
                85                  90                  95

Gly Val Tyr Tyr Val Phe Phe Gln Leu Glu Leu Arg Arg Val Val Ala
            100                 105                 110

Gly Glu Gly Ser Gly Ser Val Ser Leu Ala Leu His Leu Gln Pro Leu
        115                 120                 125
```

Arg Ser Ala Ala Gly Ala Ala Ala Leu Ala Leu Thr Val Asp Leu Pro
    130                 135                 140

Pro Ala Ser Ser Glu Ala Arg Asn Ser Ala Phe Gly Phe Gln Gly Arg
145                 150                 155                 160

Leu Leu His Leu Ala Gly Gln Arg Leu Gly Val His Leu His Thr Glu
                165                 170                 175

Ala Arg Ala Arg His Ala Trp Gln Leu Thr Gln Gly Ala Thr Val Leu
            180                 185                 190

Gly Leu Phe Arg Val
        195

<210> SEQ ID NO 81
<211> LENGTH: 207
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin1-Peptide linker 1)
      synthesized by Shanghai Generay Biological Engineering CO. Ltd.

<400> SEQUENCE: 81 ggttttctt tcttatttgt tcaaggcaat cagcgtgctc atggacaaga tttggggact      60
cttggttcct gtctccagcg cttcaccaca atgccttttc tattctgcaa cgtcaatgac    120
gtatgtaact ttgcctcacg aaatgattat tcgtactggc tgggaggtgg tggatcaggt    180
ggaggtggat ctggtggagg tggaagt                                        207

<210> SEQ ID NO 82
<211> LENGTH: 228
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin1-Peptide linker 5)
      synthesized by Shanghai Generay Biological Engineering CO. Ltd.

<400> SEQUENCE: 82 ggttttctt tcttatttgt tcaaggcaat cagcgtgctc atggacaaga tttggggact      60
cttggttcct gtctccagcg cttcaccaca atgccttttc tattctgcaa cgtcaatgac    120
gtatgtaact ttgcctcacg aaatgattat tcgtactggc tggctgaagc tgctgccaaa    180
gaagccgctg ctaaggaagc agctgccaag gaagccgctg ccaaggcc                 228

<210> SEQ ID NO 83
<211> LENGTH: 264
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin2-Peptide linker 1)
      synthesized by Shanghai Generay Biological Engineering CO. Ltd.

<400> SEQUENCE: 83
caagatttag gtactttggg ctcttgtctt cagcgtttta ccacaatgcc tttcctcttt     60
tgcaatgtta acgacgtctg taatttcgct tcccgcaacg attattcata ctggctatcg    120
acgcccgccc tgatgccaat gaatatggca ccgattactg acgagcgtt agaacctat     180 atcagtcggt gcaccgtatg tgaggggccc gctatagccg gaggtggtgg atcaggtgga    240
ggtggatctg gtggaggtgg aagt                                           264

<210> SEQ ID NO 84

<211> LENGTH: 285
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin2-Peptide linker 5)
      synthesized by Shanghai Generay Biological Engineering CO. Ltd.

<400> SEQUENCE: 84
caagatttag gtactttggg ctcttgtctt cagcgtttta ccacaatgcc tttcctcttt      60
tgcaatgtta acgacgtctg taatttcgct tcccgcaacg attattcata ctggctatcg    120
acgcccgccc tgatgccaat gaatatggca ccgattactg gacgagcgtt agaaccttat    180
atcagtcggt gcaccgtatg tgagggcccc gctatagccg ctgaagctgc tgccaaagaa    240
gccgctgcta aggaagcagc tgccaaggaa gccgctgcca aggcc                    285

<210> SEQ ID NO 85
<211> LENGTH: 162
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin3-Peptide linker 1)
      synthesized by Shanghai Generay Biological Engineering CO. Ltd.

<400> SEQUENCE: 85
caagatttag gtactttggg ctcttgtctt cagcgtttta ccacaatgcc tttcctcttt      60
tgcaatgtta acgacgtctg taatttcgct tcccgcaacg attattcata ctggctagga    120
ggtggtggat caggtggagg tggatctggt ggaggtggaa gt                        162

<210> SEQ ID NO 86
<211> LENGTH: 183
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin3-Peptide linker 5)
      synthesized by Shanghai Generay Biological Engineering CO. Ltd.

<400> SEQUENCE: 86
caagatttag gtactttggg ctcttgtctt cagcgtttta ccacaatgcc tttcctcttt      60
tgcaatgtta acgacgtctg taatttcgct tcccgcaacg attattcata ctggctagct    120
gaagctgctg ccaaagaagc cgctgctaag gaagcagctg ccaaggaagc cgctgccaag    180
gcc                                                                  183

<210> SEQ ID NO 87
<211> LENGTH: 120
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin7-Peptide linker 1)
      synthesized by Shanghai Generay Biological Engineering CO. Ltd.

<400> SEQUENCE: 87
acaatgccat tcttattctg caatgtcaat gatgtatgta attttgcatc tcgtaatgat      60
tattcatact ggctgggagg tggtggatca ggtggaggtg gatctggtgg aggtggaagt    120

<210> SEQ ID NO 88
<211> LENGTH: 126
<212> TYPE: DNA
<213> ORGANISM: Artificial Sequence

```
<220> FEATURE:
<223> OTHER INFORMATION: The nucleotide sequence containing the gene of
      Tumstatin and peptide linker (Tumstatin7-Peptide linker 2)
      synthesized by Shanghai Generay Biological Engineering CO. Ltd.

<400> SEQUENCE: 88
acaatgccat tcttattctg caatgtcaat gatgtatgta attttgcatc tcgtaatgat      60
tattcatact ggctgggagg tggtggatca ggtggaggtg gatctggtgg aggtggatct     120
ggtgga                                                                126

<210> SEQ ID NO 89
<211> LENGTH: 102
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin7-Peptide linker 3)
      synthesized by Shanghai Generay Biological Engineering CO. Ltd.

<400> SEQUENCE: 89
acaatgccat tcttattctg caatgtcaat gatgtatgta attttgcatc tcgtaatgat      60
tattcatact ggctgggagg tggtggatca ggtggaggtc ct                        102

<210> SEQ ID NO 90
<211> LENGTH: 117
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin7-Peptide linker 4)
      synthesized by Shanghai Generay Biological Engineering CO. Ltd.

<400> SEQUENCE: 90
acaatgccat tcttattctg caatgtcaat gatgtatgta attttgcatc tcgtaatgat      60
tattcatact ggctgggagg tggtggatca ggtggaggtc ctggatcagg tggaggt        117

<210> SEQ ID NO 91
<211> LENGTH: 141
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin7-Peptide linker 5)
      synthesized by Shanghai Generay Biological Engineering CO. Ltd.

<400> SEQUENCE: 91
acaatgccat tcttattctg caatgtcaat gatgtatgta attttgcatc tcgtaatgat      60
tattcatact ggctggctga agctgctgcc aaagaagccg ctgctaagga agcagctgcc    120
aaggaagccg ctgccaaggc c                                              141

<210> SEQ ID NO 92
<211> LENGTH: 156
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin7-Peptide linker 6)
      synthesized by Shanghai Generay Biological Engineering CO. Ltd.

<400> SEQUENCE: 92
acaatgccat tcttattctg caatgtcaat gatgtatgta attttgcatc tcgtaatgat      60
tattcatact ggctggctga agctgctgcc aaagaagccg ctgctaagga agcagctgcc    120
```
aaggaagccg ctgccaaggc cgctgcagcc aaggct                                      156

<210> SEQ ID NO 93
<211> LENGTH: 126
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin7-Peptide linker 7)
      synthesized by Shanghai Generay Biological Engineering CO. Ltd.

<400> SEQUENCE: 93
acaatgccat tcttattctg caatgtcaat gatgtatgta attttgcatc tcgtaatgat       60
tattcatact ggctggctga agctgctgcc aaagaagccg ctgctaagga agcagctgcc      120
aaggct                                                                 126

<210> SEQ ID NO 94
<211> LENGTH: 144
<212> TYPE: DNA
<213> ORGANISM: Artificial Sequence
<220> FEATURE:
<223> OTHER INFORMATION: The nucleotide sequence containing the gene of
      Tumstatin and peptide linker (Tumstatin7-Peptide linker 8)
      synthesized by Shanghai Generay Biological Engineering CO. Ltd.

<400> SEQUENCE: 94
acaatgccat tcttattctg caatgtcaat gatgtatgta attttgcatc tcgtaatgat       60
tattcatact ggctggctga agctgctgcc aaagaagccg ctgctaagga agcagctgcc      120
aaggaagccg ctgccaaggc ccct                                             144

<210> SEQ ID NO 95
<211> LENGTH: 25
<212> TYPE: DNA
<213> ORGANISM: Artificial Sequence
<220> FEATURE:
<223> OTHER INFORMATION: Upstream primer of SEQ ID NO. 49

<400> SEQUENCE: 95
ggatccgccg tcttcctcgc ctgcc                                             25

<210> SEQ ID NO 96
<211> LENGTH: 30
<212> TYPE: DNA
<213> ORGANISM: Artificial Sequence
<220> FEATURE:
<223> OTHER INFORMATION: Downstream primer of SEQ ID NO. 49

<400> SEQUENCE: 96
gcggccgctt ccgacctcgg tgaagggagt                                        30

<210> SEQ ID NO 97
<211> LENGTH: 31
<212> TYPE: DNA
<213> ORGANISM: Artificial Sequence
<220> FEATURE:
<223> OTHER INFORMATION: Upstream primer of the fusion gene (SEQ ID NO.5
      to SEQ ID NO.12)

<400> SEQUENCE: 97
gctagcacaa tgccattctt attctgcaat g                                      31

<210> SEQ ID NO 98
<211> LENGTH: 31
<212> TYPE: DNA

```
<213> ORGANISM: Artificial Sequence
<220> FEATURE:
<223> OTHER INFORMATION: Downstream primer of the fusion gene (SEQ ID
      NO.5- SEQ ID NO.12)

<400> SEQUENCE: 98
catatgttcc gacctcggtg aagggagtcc g                                      31

<210> SEQ ID NO 99
<211> LENGTH: 28
<212> TYPE: DNA
<213> ORGANISM: Artificial Sequence
<220> FEATURE:
<223> OTHER INFORMATION: Upstream primer of SEQ ID NO. 50

<400> SEQUENCE: 99
cgggatccgc ctcttggacc tgcggcag                                          28

<210> SEQ ID NO 100
<211> LENGTH: 29
<212> TYPE: DNA
<213> ORGANISM: Artificial Sequence
<220> FEATURE:
<223> OTHER INFORMATION: Downstream primer of SEQ ID NO. 50

<400> SEQUENCE: 100
gcggccgctt ccgacctcgg tgaagggag                                         29

<210> SEQ ID NO 101
<211> LENGTH: 31
<212> TYPE: DNA
<213> ORGANISM: Artificial Sequence
<220> FEATURE:
<223> OTHER INFORMATION: Upstream primer of SEQ ID NO.1

<400> SEQUENCE: 101
gctagcggtt tttctttctt atttgttcaa g                                      31

<210> SEQ ID NO 102
<211> LENGTH: 31
<212> TYPE: DNA
<213> ORGANISM: Artificial Sequence
<220> FEATURE:
<223> OTHER INFORMATION: Upstream primer of SEQ ID NO.3

<400> SEQUENCE: 102
gctagcggtt tttctttctt atttgttcaa g                                      31

<210> SEQ ID NO 103
<211> LENGTH: 31
<212> TYPE: DNA
<213> ORGANISM: Artificial Sequence
<220> FEATURE:
<223> OTHER INFORMATION: Upstream primer of SEQ ID NO.13- SEQ ID NO.14

<400> SEQUENCE: 103
gctagccaag atttaggtac tttgggctct t                                      31

<210> SEQ ID NO 104
<211> LENGTH: 31
<212> TYPE: DNA
<213> ORGANISM: Artificial Sequence
<220> FEATURE:
<223> OTHER INFORMATION: Upstream primer of SEQ ID NO.15- SEQ ID NO.16

<400> SEQUENCE: 104
```
gctagcaaga gcccaaagta cctaaatctt g                                    31

<210> SEQ ID NO 105
<211> LENGTH: 27
<212> TYPE: DNA
<213> ORGANISM: Artificial Sequence
<220> FEATURE:
<223> OTHER INFORMATION: Downstream primer of SEQ ID NO.1, SEQ ID NO.3
      and SEQ ID NO.13- SEQ ID NO.16

<400> SEQUENCE: 105
catatgttcc gacctcggtg aagggag                                         27

<210> SEQ ID NO 106
<211> LENGTH: 26
<212> TYPE: DNA
<213> ORGANISM: Artificial Sequence
<220> FEATURE:
<223> OTHER INFORMATION: Upstream primer 1 of SEQ ID NO.51

<400> SEQUENCE: 106
cgggatccgc cgtcttcctc gcctgc                                          26

<210> SEQ ID NO 107
<211> LENGTH: 20
<212> TYPE: DNA
<213> ORGANISM: Artificial Sequence
<220> FEATURE:
<223> OTHER INFORMATION: Downstream primer 1 of SEQ ID NO.51

<400> SEQUENCE: 107
cgcaaacatg ccctgccctg                                                 20

<210> SEQ ID NO 108
<211> LENGTH: 39
<212> TYPE: DNA
<213> ORGANISM: Artificial Sequence
<220> FEATURE:
<223> OTHER INFORMATION: Upstream primer 2 of SEQ ID NO.51

<400> SEQUENCE: 108
cagggcaggg catgtttgcg ggtttccagg gccgcttgc                            39

<210> SEQ ID NO 109
<211> LENGTH: 29
<212> TYPE: DNA
<213> ORGANISM: Artificial Sequence
<220> FEATURE:
<223> OTHER INFORMATION: Downstream primer 2 of SEQ ID NO.51

<400> SEQUENCE: 109
gcggccgctt ccgacctcgg tgaagggag                                       29

<210> SEQ ID NO 110
<211> LENGTH: 31
<212> TYPE: DNA
<213> ORGANISM: Artificial Sequence
<220> FEATURE:
<223> OTHER INFORMATION: Upstream primer of SEQ ID NO.2 and SEQ ID NO.4

<400> SEQUENCE: 110
gctagcggtt tttctttctt atttgttcaa g                                    31

<210> SEQ ID NO 111
<211> LENGTH: 24
<212> TYPE: DNA

```
<213> ORGANISM: Artificial Sequence
<220> FEATURE:
<223> OTHER INFORMATION: Upstream primer of SEQ ID NO.17

<400> SEQUENCE: 111
gctagccaag atttaggtac tttg                                          24

<210> SEQ ID NO 112
<211> LENGTH: 31
<212> TYPE: DNA
<213> ORGANISM: Artificial Sequence
<220> FEATURE:
<223> OTHER INFORMATION: Upstream primer of SEQ ID NO.18

<400> SEQUENCE: 112
gctagccaag atttaggtac tttgggctct t                                  31

<210> SEQ ID NO 113
<211> LENGTH: 27
<212> TYPE: DNA
<213> ORGANISM: Artificial Sequence
<220> FEATURE:
<223> OTHER INFORMATION: Downstream primer of SEQ ID NO.2, SEQ ID NO.4,
      SEQ ID NO.17 and SEQ ID NO.18

<400> SEQUENCE: 113
catatgttcc gacctcggtg aagggag                                       27
```

BIFUNCTIONAL FUSION PROTEINS TO INHIBIT ANGIOGENESIS IN TUMOR MICROENVIRONMENT AND TO ACTIVATE ADAPTIVE IMMUNE RESPONSES AND THE GENES AND USES THEREOF

CROSS-REFERENCE TO RELATED APPLICATIONS

This application claims priority to PCT Application No. PCT/CN2014/076768, having a filing date of May 5, 2014, based off of Chinese Application No. 201310162738.3, having a filing date of May 6, 2013, based off Chinese Application No. 201310163407.1, having a filing date of May 6, 2013, the entire contents of which are hereby incorporated by reference.

SEQUENCE LISTING

This application include a separate sequence listing in compliance with the requirements of 37 C.F.R. §§ 1.824(a)(2)-1.824(a)(6) and 1.824(b), submitted under the file name "51467_Sequence Listing_ST25", created on Dec. 3, 2015, having a file size of 113 kilobytes, the contents of which are hereby incorporated by reference.

FIELD OF TECHNOLOGY

The following belongs to biomedical engineering and therapeutics fields. The following generally relates to a series of bifunctional fusion proteins (CD137L-Tumstatin) and their genes, wherein the proteins have the functions of inhibiting angiogenesis in tumor microenvironment and activating the adaptive immune responses. The following also relates to the expression vector containing the genes, the strains transformed by the expression vector and the preparation method of the bifunctional fusion proteins. In addition, the following generally relates to the application of the bifunctional fusion proteins possessing the activities of Tumstatin and CD137L in the preparation of pharmaceutical agents to inhibit angiogenesis in tumor microenvironment and to treat various tumor-related diseases (e.g., melanoma, rectal cancer, lung cancer and other cancers) by activating the adaptive immune responses, as well as all possible administration routes (e.g., oral administration, spray administration and others).

BACKGROUND

The occurrence of cancer is a process covering multiple genes and different signal pathways. As for its essence, cancer is a type of molecular disease. Currently, the molecular therapy targeting a single target has gradually shown many shortcomings, whereas the therapeutic strategies combining multiple targets or multiple mechanisms show better therapeutic effects.

In 1971, Professor Folkman from Harvard University proposed the theory that "The growth and metastasis of tumors depend on the angiogenesis in microenvironment". He hypothesized that the growth and metastasis of tumors might be inhibited by suppressing angiogenesis in microenvironment and cutting off the supply of nutrients and oxygen to tumors. Up to now, this theory has been verified by numerous experimental and clinical data all over the world, and thus recently become a new strategy within the field of cancer therapy. Tumstatin, a protein consisting of 244 amino acids, is a tumor angiogenesis inhibitor derived from the C-terminal of α3 chain of type IV collagen in vascular basement membrane.

Among all vascular basement membranes, the three-dimensional reticular framework formed by type IV collagen plays a predominant role as stents, which may promote adhesion, migration, differentiation and growth of cells. The 6 chains (α1~α6) are encoded by 6 distinct genes, forming a trimer through the same or different a chains, further forming the reticular framework. Each α3 chain of type IV collagen consists of three functional units (7S domain, triple helix region, non-collagenous NC1 domain), and distributes in the basement membranes of glomerular, alveolar capillaries, cochlea, lens capsule, ovary and testicular.

Angiogenesis is a critical step in tumor growth and metastasis, which includes a series of complex processes. The hypoxia in tumor tissues makes the increase of angiogenesis stimulating factors, thus stimulating angiogenesis in tumor microenvironment. Recent studies show that Tumstatin can specifically inhibit the synthesis of tumor vascular endothelial cell proteins, resulting in the apoptosis of endothelial cell and the inhibition of angiogenesis, and thereby inhibiting tumor growth and metastasis. In addition, Tumstatin also has a direct effect on tumor cells to inhibit their proliferation. The action of mechanism by Tumstatin is to inhibit the synthesis of vascular endothelial cell proteins specifically located in tumor microenvironment through binding integrin receptor αvβ3 that inhibits the synthesis of proteins in tumor vascular endothelial cells; thus the growth and metastasis of tumor cells can be inhibited by inhibiting angiogenesis.

Cancer immunotherapy has been recognized in the field to show advantageous effects against malignant tumors in humans and animals through the immune-responses. The immune cells of cancer patients recognize different antigens expressed by tumor cells, such as tissue differentiation antigen, carcinoembryonic antigen, the mutated gene products and others. With the understanding of the mechanisms on tumor antigen recognition and immune response, it has been shown that the anti-tumor immune responses can be enhanced by providing the immuno-costimulatory signal through T cell co-receptors. The tumor antigen-specific T cells require costimulatory signal to assist the first signal initiated by antigen to activate the effective cells. Therefore, adjuvant therapy by costimulatory molecules can be used to regulate the immune responses targeting malignant tumors.

Costimulatory molecules play an extremely important role in immune response. In general, two signals are required in the activation of T lymphocytes. The first signal is provided by T cell receptor (TCR) and MHC-antigen peptide presented in Antigen Presenting Cells (APC), and the second signal is the costimulatory signal provided by adhesion molecules on cell surface. One of the important ways to enhance T cell mediated anti-tumor immune response is to provide costimulatory signals to achieve full activation of T lymphocytes. Besides CD28/B7, CD137 and its ligand CD137L is another pair of important T cell costimulatory molecules discovered recently.

According to their structures, the costimulatory molecules can be divided into two types, including Tumor Necrosis Factor Receptor (TNFR) and immunoglobulin superfamily. CD137, a member of TNFR, plays an important role in the regulation of cell proliferation, differentiation and apoptosis. Its ligand CD137L is also a member of TNF family, which belongs to type II transmembrane proteins on cell surface and shares similar C-terminal amino acid sequence to other members of TNF family. The gene encoding human CD137L is located in 19p3.3, and its product consists of 254 amino acids, wherein the cytoplasmic domain consists of 28 amino acids, the transmembrane region consists of 21 amino acids, and the extracellular domain consists of 205 amino acids. CD137L was first discovered by Goodwin et al using expression screening of the thymoma cells in mice, and later isolated from human CD4+ T cell clones.

It is well-known that the interaction between CD137 and its ligand CD137L plays an important role in T cell activation. In mouse and human T cells, in the presence of CD3 antibody (first signal), CD137 can induce the proliferation of T cells, the synthesis of cytokines (such as IFN-α) and the survival of activated cells. Costimulatory signal can improve the effector function by enhancing the antigenic specificity and increase the number of CD8+ T cells. In the absence of CD3 antibody, the stimulation of CD137 does not change the functions of T cells, indicating that the interaction between CD137 and CD137L only provides a costimulatory signal.

The studies of Kim et al and others showed that the anti-tumor immunity mediated by CD137 monoclonal antibody is dependent on the participation of both CD4+ T and CD8+ T cells. CD137 mediates the activation of NF-κB to upregulate the expression of bcl-xL and bfl-1, to extend the survival of CD8+ T and CD4+ T cells and to promote their proliferation. Using agonistic murine CD137L monoclonal antibody, Melero and others carried out the CD137 targeted immunotherapy. Their results showed that CD137 monoclonal antibody could eliminate the presence of inoculated P815 solid tumors in mice. Consistent with the anti-tumor effects of the agonistic CD137 monoclonal antibody, CD137L can also costimulate the cytotoxic lymphocyte (CTL) and their anti-tumor effects. CD137L-/- mouse is a good illustration of the important role of CD137/CD137L system in T cell-mediated immune responses against viruses and tumors which shows that the costimulation of CD137/CD137L is vital in graft versus host disease and antiviral T cell responses.

To summarize, the costimulatory signal provided by CD137/CD137L can cooperate with that of CD28/B7 for further activation of T cells and the maintenance of the proliferation and survival of CD8+ T cells. Tumstatin can effectively inhibit tumor angiogenesis, which may block tumor cells from survival and metastasis. Therefore, to combine the strategies of antiangiogenesis and immunotherapy, Tumstatin-CD137L fusion protein stated in embodiments of the present invention can suppress tumor growth and metastasis by the combination of two mechanisms, which could avoid drug resistance from single agent therapy and provide a new way for cancer therapy.

SUMMARY

An aspect relates to bifunctional and dual-targeting proteins, possessing activities of enhancing T-cell immunity and inhibiting angiogenesis, are prepared by fusing the antiangiogenic active fragments of Tumstatin with the extracellular regions of CD137L through short flexible peptide linkers. Different active fragments of Tumstatin (Tumstatin1 contains amino acid residues from 45 to 98, Tumstatin2 contains amino acid residues from 60 to 132, Tumstatin3 contains amino acid residues from 60 to 98, Tumstatin7 contains amino acid residues from 74 to 98) and the extracellular amino acid sequences of CD137L (CD137L1 contains amino acid residues from 46 to 254, CD137L4 contains amino acid residues from 50 to 240, CD137L5 contains amino acid residues from 83 to 254, CD137L6, a combined fragment, contains amino acid residues from 46 to 85 and from 167 to 254, as indicated in FIG. 2) are connected by a peptide linker, and prepared using prokaryotic or eukaryotic expression systems. The fusion proteins have the advantages of simple preparation and reduced side effects from full length Tumstatin and CD137L respectively. Embodiments of the present invention exhibits excellent potentials in the preparation of pharmaceutical agents for angiogenesis inhibition, all types of tumor associated diseases (such as melanoma, prostate cancer, lung cancer, colorectal cancer, and bladder cancer and others), retinal pathological changes, cell proliferation, cytokine synthesis and secretion, and regulation of immunity, as well as in the preparation of pharmaceutical agents with different formulations including oral or injection administration.

The purpose of embodiments of the present invention is to provide proteins possessing both functions of Tumstatin and CD137L.

The other purpose of embodiments of the present invention is to provide genes encoding proteins with the functions of Tumstatin and CD137L.

Another purpose of embodiments of the present invention is to provide preparation methods for the proteins possessing the functions of Tumstatin and CD137L.

Another purpose of embodiments of the present invention is to provide the applications of the genes and proteins possessing the functions of Tumstatin and CD137L in the treatment of oncology related diseases (such as melanoma, rectal cancer, lung cancer and others) and in the administration routes of the pharmaceutical agents (such as oral administration, spray administration and others).

The technical scheme of embodiments of the present invention is described as follows:

Bifunctional fusion proteins possessing the activities of Tumstatin and CD137L, characterized in that the proteins comprise the amino acid sequences of the active fragments of Tumstatin and the extracellular domains of CD137L, wherein the sequences of Tumstatin and CD137L are fused together through flexible peptide linkers, wherein the amino acid sequence of Tumstatin active fragment is selected from SEQ ID NO:65 to SEQ ID NO:68, wherein the amino acid sequence of CD137L extracellular region is selected from SEQ ID NO:77 to SEQ ID NO:80.

The amino acid sequences of the above described peptide linker can be designed with the techniques well known in the art, and the preferred amino acid sequences are selected from SEQ ID NO:69 to SEQ ID NO:76.

The amino acid sequences of the bifunctional recombinant proteins described in embodiments of the present invention are selected from SEQ ID NO. 25 to SEQ ID NO:48. A schematic representation of the structures of the recombinant proteins is shown in FIG. 1.

Embodiments of the present invention also provide genes encoding the recombinant proteins possessing the functions of Tumstatin and CD137L, which includes the gene encoding an active fragment of Tumstatin, the gene encoding a peptide linker and the gene encoding an extracellular region of CD137L, wherein the genes encoding CD137L extracellular region are selected from SEQ ID NO:61 to SEQ ID NO:64, wherein the genes encoding the Tumstatin active fragment are selected from SEQ ID NO:49 to SEQ ID NO:52.

The gene encoding above described peptide linker is preferably selected from SEQ ID NO:53 to SEQ ID NO:60

The nucleotide sequence encoding above described recombinant protein is preferably selected from SEQ ID NO:1 to SEQ ID NO:24.

Embodiments of the present invention also provide a gene encoding a recombinant protein Tumstatin-CD137L, which has a 70% or more homology compared with above described nucleotide sequences and produces an above described recombinant protein, its conservatively variant polypeptide, its active fragment or its active derivatives thereof.

Embodiments of the present invention also provide a preparation method for the bifunctional recombinant proteins possessing the activities of Tumstatin and CD137L, which includes the following steps:

(1) Design and obtain the nucleotide sequences encoding the recombinant proteins possessing the activities of Tumstatin and CD137L described in embodiments of the present invention;

(2) Construct the expression system containing above described nucleotide sequences, including constructing the expression vector and transforming the expression vector into a host cell to form recombinant cells that can express the bifunctional fusion proteins possessing the activities of Tumstatin and CD137L;

(3) Culture the recombinant cells obtained from step (2);

(4) Isolate and purify the recombinant proteins possessing the activities of Tumstatin and CD137L described in embodiments of the present invention.

The above described expression system could select a prokaryotic expression system or a eukaryotic expression system. The prokaryotic expression system is preferably selected from *Escherichia coli* or *Bacillus subtilis*, both of which are generally applicable to the expression of the recombinant proteins described in embodiments of the present invention. The expression vector is preferably selected from pET-11a or pET-22b for *Escherichia coli* expression system, while pP43 is the preferred vector for *Bacillus* expression system. Yeast is the preferred eukaryotic expression system, the expression vector is preferably selected from pPIC9K or pPICZαA, and the host cells are preferably selected from GS115 or SMD1168.

A preferred preparation method described above includes the process of double-digesting the genes encoding the recombinant proteins possessing the activities of Tumstatin and CD137L with the enzymes of NdeI and NheI, ligating them with the expression vector pET-11a, and transforming the ligated vectors into *E. coli* BL21 (DE3). After culturing of the engineered bacteria, the recombinant proteins are produced in the form of inclusion body and obtained by dilution renaturation which includes a process of washing the inclusion body by buffer containing low concentrations of urea, solubilizing the inclusion body by denaturant solution containing 8 M urea at 50° C., and renaturation by dilution with the refolding solution containing L-Arg at the concentration of 0.4 M. The purity of the desired products is greater than 80%.

Another preferred preparation method described above include the process of double-digesting the genes encoding the recombinant proteins possessing activities of Tumstatin and CD137L with the enzymes of PstI and HindIII, ligating them with the expression vector pP43, transforming the ligated vectors into *Bacillus subtilis* WB800 by electroporation. After culturing of the engineered bacteria, the recombinant proteins are produced in a secreted soluble form. The recombinant proteins described in embodiments of the present invention are obtained through purification by DEAE-sephadex anion exchange chromatography, and the purity is greater than 80%.

Another preferred preparation method described above includes the process of double-digesting the genes encoding the recombinant proteins possessing activities of Tumstatin and CD137L with the enzymes of EcoRI and NotI, ligating them with the expression vector pPICZαA, transforming the vectors into *Pichia pastoris* GS115 by electroporation. After culturing of the engineered bacteria, the recombinant proteins are produced in a secreted soluble form. The recombinant proteins described in embodiments of the present invention are obtained through purification by DEAE-sephadex anion exchange chromatography, and the purity is greater than 90%.

Embodiments of the present invention also provide the application of the bifunctional recombinant proteins possessing activities of Tumstatin and CD137L to prepare pharmaceutical agents for inhibiting angiogenesis in tumor microenvironment, treating various tumor-related diseases (such as melanoma, rectal cancer, lung cancer and others), regulating body immunity, stimulating T cell proliferation and synthesizing and secreting cytokines.

In above described applications, the recombinant proteins described in embodiments of the present invention can be used alone or in the form of pharmaceutical compositions. The pharmaceutical composition comprises the recombinant protein described in embodiments of the present invention as an active component and a pharmaceutically acceptable carrier. Preferably, the pharmaceutical composition comprises from 0.1% to 99.9% by weight of a recombinant protein described in embodiments of the present invention as an active ingredient. The pharmaceutically acceptable carrier will not interfere with the pharmaceutical activity and the effective dosage of a recombinant protein described in embodiments of the present invention, meaning that the carrier dosage is nontoxic to human body.

The pharmaceutically acceptable carrier includes, but is not limited to, one or more of the following: ion exchange materials; aluminum oxide; aluminium stearate; lecithin; self emulsifying drug delivery system (SEDDS), such as vitamin D and E, polyethylene glycol 1000, succinate, Tween, and other polymerization medium with similar functions; other pharmaceutically acceptable surfactants; serum albumins, such as human serum albumin; buffers, such as phosphate-buffered saline; aminoacetic acid; sorbic acid; sorbic acid potassium; saturated plant fatty acid; mixtures of glycerides; water; salts; electrolytes, such as protamine sulfate, disodium hydrogen phosphate, potassium hydrogen phosphate, sodium chloride, zinc salts, silica gels, magnesium silicate, and others. Polyvinylpyrrolidone, cellulose, polyvinyl alcohol, sodium carboxymethylcellulose, polyacrylate, ethylene, polyoxyethylene, block copolymer (such as lanolin) and cyclodextrin (such as α-, β-, γ-cyclodextrin, chemically modified derivatives e.g. 2- and 3-hydroxypropyl-β-cyclodextrin, or other soluble derivatives) are also applicable for the delivery of the recombinant proteins described in embodiments of the present invention.

Other pharmaceutically acceptable excipients could also be incorporated into the pharmaceutical compositions, which include fillers (such as anhydric lactose, starch, lactose or glucose), binding agents (such as microcrystalline cellulose), disintegrating agent (such as cross-linked sodium carboxymethyl starch, cross-linked sodium carboxymethyl cellulose, low substituted hydroxypropyl cellulose (L-HPC) or crosslinked PVP), lubricating agents (such as magnesium stearate), absorption enhancer, flavoring agents, sweetening agents, diluents, vehicles, wetting agents, solvents, solubilizers and coloring agents and others.

Above described pharmaceutical compositions could be used in any pharmaceutical acceptable formulations. For example, oral administration, such as tablets, capsules, granules, powder or liquid preparations, parenteral administration, such as injections, local administrations or suppositories, which could be prepared by methods well known in the art or by non-conventional methods such as liposomes and others.

When the recombinant proteins described in embodiments of the present invention are used as a therapeutic agent, the daily dose for adults may range from 0.01 mg to 1 g, which depends on age, gender, weight, and the degree of sickness of the patients. In addition, the total daily dose may be divided and administered in portions during the day.

The recombinant proteins described in embodiments of the present invention also include the protein derivatives that are modified by methods well known in the art of the present technical field.

Under most circumstances, most protein and peptide drugs can be digested step by step from the two termini of the linear peptides by aminopeptidase and carboxypeptidase.

Polypeptide modification is an important means to change the structure of the main chain and the side chain. It has been indicated by a large number of studies that the modified polypeptide drugs showed a better efficacy exhibiting significantly reduced immunogenicity, reduced side effects, increased water solubility, prolonged biological half-lives in vivo and changed the tissue distribution, etc.

The modification methods described in embodiments of the prevent invention consists of the modifications in intermediate amino acid residues, amino acid substitutions, glycosylation modification and PEG modification and others, the basic principles of which are increasing the relative molecular weight and steric hindrance of the polypeptide molecules and improving the stability of the polypeptide to hydrolase, and reducing the filtration function of the glomerular.

Amino acid substitution is another method to prolong the half-life of polypeptide drugs through postponing the digestion of enzymes. The object residues usually are those easily digested amino acids. In detail, the intermediate residues of the recombinant proteins could be glycosylated, phosphorylated, methylated, acetylated, nitrated, sulfonated, PEG-lyated or coupled with other proteins, wherein:

For glycosylation, N-glycosylation and O-glycosylation are commonly used. Glycosylated peptides are preferably to attach one or more hydroxyl oxygen on tyrosine, serine or threonine residues or one or more nitrogen of asparagine side-chain of the recombinant proteins described in embodiments of the present invention with glycans.

Phosphorylated peptides are preferably phosphorylate the recombinant proteins described in embodiments of the present invention at one or more Tyr, Ser or Thr residues.

Methylated peptides include side chain methylated and N-terminal methylated peptides. Side chain methylation is preferably methylate the recombinant proteins described in embodiments of the present invention at one or more Lys, Tyr or Arg side chain, such as Lys(For), Lys(Me), Lys(Me)2, Lys(Me)3, Arg(Me)2 symmetrical, D-Tyr(Me), D-Tyr(Et);

Acetylated peptides are preferably acetylate the recombinant proteins described in embodiments of the present invention at one or more Lys or Ser side chain, such as Ser (Ac) or Lys (Ac).

Nitrated or sulfonated peptides are preferably nitrate or sulfonate the recombinant proteins described in embodiments of the present invention at one or more Tyr side chain, such as, Tyr (3-$NO_2$), Tyr ($SO_3H_2$).

PEG-lyated peptides are preferably PEG-lyate the recombinant proteins described in embodiments of the present invention at one or more Lys side chain. The molecular weight of the PEG is preferably about 2000-10,000.

Alternatively, one or more amino acid residues of the recombinant proteins or the modified proteins described above in embodiments of the present invention could be substituted with the amino acid derivatives or unusual amino acids, such as substituting alanine with β-alanine, homophenylalanine or naphthylalanine, substituting proline with hydroxyproline, substituting leucine with norleucine, substituting valine with norvaline, substituting threonine with allothreonine, substituting isoleucine with alloisoleucine, substituting asparagine with Asn(GlcNac(Ac)3-β-D)), substituting lysine with Lys(palmitoyl).

Alternatively, one or more amino acid residues of the recombinant proteins or the modified proteins described above in embodiments of the present invention could be substituted with D-type amino acids.

The gene encoding the bifunctional recombinant proteins possessing the activities of Tumstatin and CD137L (GenBank: AAF72632.1 and NP_003802.1) could be obtained by strategies well known in the art, such as gene synthesis, PCR or the combination of them, wherein the full nucleotide sequence of CD137L could be obtained through the published method (Wang shuzhen. J Ind MicrobioBiotechnol. 2012 March; 39(3):471-6. doi:10.1007/s10295-011-1045-1).

Embodiments of the present invention construct the expression vectors encoding above described bifunctional recombinant proteins possessing the activities of Tumstatin and CD137L, wherein the correct expression vector is obtained by routine PCR amplification, digesting and ligating which includes double-digesting the gene encoding Tumstatin-Peptide linker-CD137L extracellular domain by NdeI and NheI, ligating above obtained DNA fragment into the corresponding sites of the prokaryotic expression vector pET-11a, and the vector is sequenced to verify.

Embodiments of the present invention construct the engineered bacteria containing above described expression vectors, which includes transforming a target gene into BL21, liquid culturing, and selecting the positive engineered strains.

Embodiments of the present invention provide methods for obtaining the bifunctional proteins possessing the activities of Tumstatin and CD137L, wherein the method is to culture and ferment the positively engineered strains, induce the expression of a bifunctional protein with the activities of Tumstatin and CD137L under room temperature, collect the cells and disrupt cells with high pressure. After dissolving denaturation and dilution refolding of the centrifuged precipitate, a bifunctional protein with the activities of Tumstatin and CD137L can be obtained.

In the present invention, the activity assay for the bifunctional fusion proteins possessing the activities of Tumstatin and CD137L is carried out by HUVEC assay and mouse T cell activation assay. The results of HUVEC assay showed that the proliferation of endothelial cells was significantly inhibited. Mouse T cell activation assay showed that above described fusion proteins can maintain the biological activity of CD137L and stimulate T cell proliferation by cooperating with anti-CD3 monoclonal antibody and anti-CD28 monoclonal antibody.

The Advantages:

Embodiments of the present invention show that the proteins possessing the activities of Tumstatin and CD137L can be prepared by using the prokaryotic expression system to express the fusion proteins comprising the active fragments of Tumstatin and CD137L extracellular regions. The recombinant proteins Tumstatin-Peptide linker-CD137L (proteins possessing the activities of both Tumstatin and CD137L) prepared according to embodiments of the present invention has the advantages of high expression efficiency and level, short expression cycle, easy purification and others. Meanwhile, embodiments of the present invention provides fusion proteins which could significantly inhibit the proliferation of human umbilical vein endothelial cells in a dose-dependent manner, and could also stimulate the proliferation mouse T cells by cooperating with anti-CD3 and anti-CD28 monoclonal antibody. Therefore, embodiments of the present invention provides a novel and safe method for large-scale production of fusion proteins possessing the activities of Tumstatin and CD137L, and lays a solid foundation for further research and development on a new generation of anticancer drugs, and has a broad application in the treatment of cancer patients.

BRIEF DESCRIPTION

Some of the embodiments will be described in detail, with reference to the following figures, wherein like designations denote like members, wherein.

Figure 6:
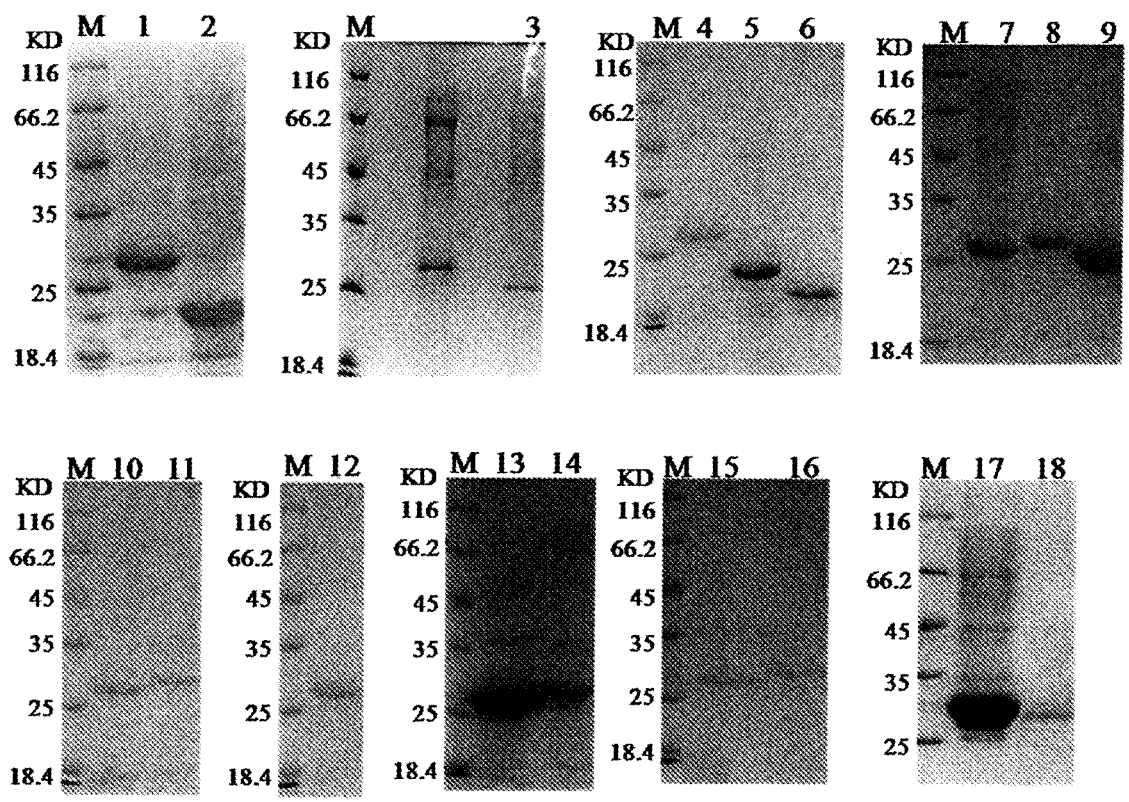

FIG. 6 is the SDS-PAGE of the representative renatured samples of Tumstatin-Peptide linker-CD137L by dilution. Wherein, the amino acid sequences of Lane 1-6 correspond to SEQ ID NO:25, 26, 27, 37, 38 and 41, respectively; the amino acid sequences of Lane 7 and 10 correspond to SEQ ID NO:43; the amino acid sequences of Lane 8 and 11 correspond to SEQ ID NO:44; the amino acid sequences of Lane 9 and 12 correspond to SEQ ID NO:48; the amino acid sequences of Lane 13 and 15 correspond to SEQ ID NO:45; the amino acid sequences of Lane 14 and 16 correspond to SEQ ID NO:46; the amino acid sequences of Lane 17 and 18 correspond to SEQ ID NO:47.

Figure 7:
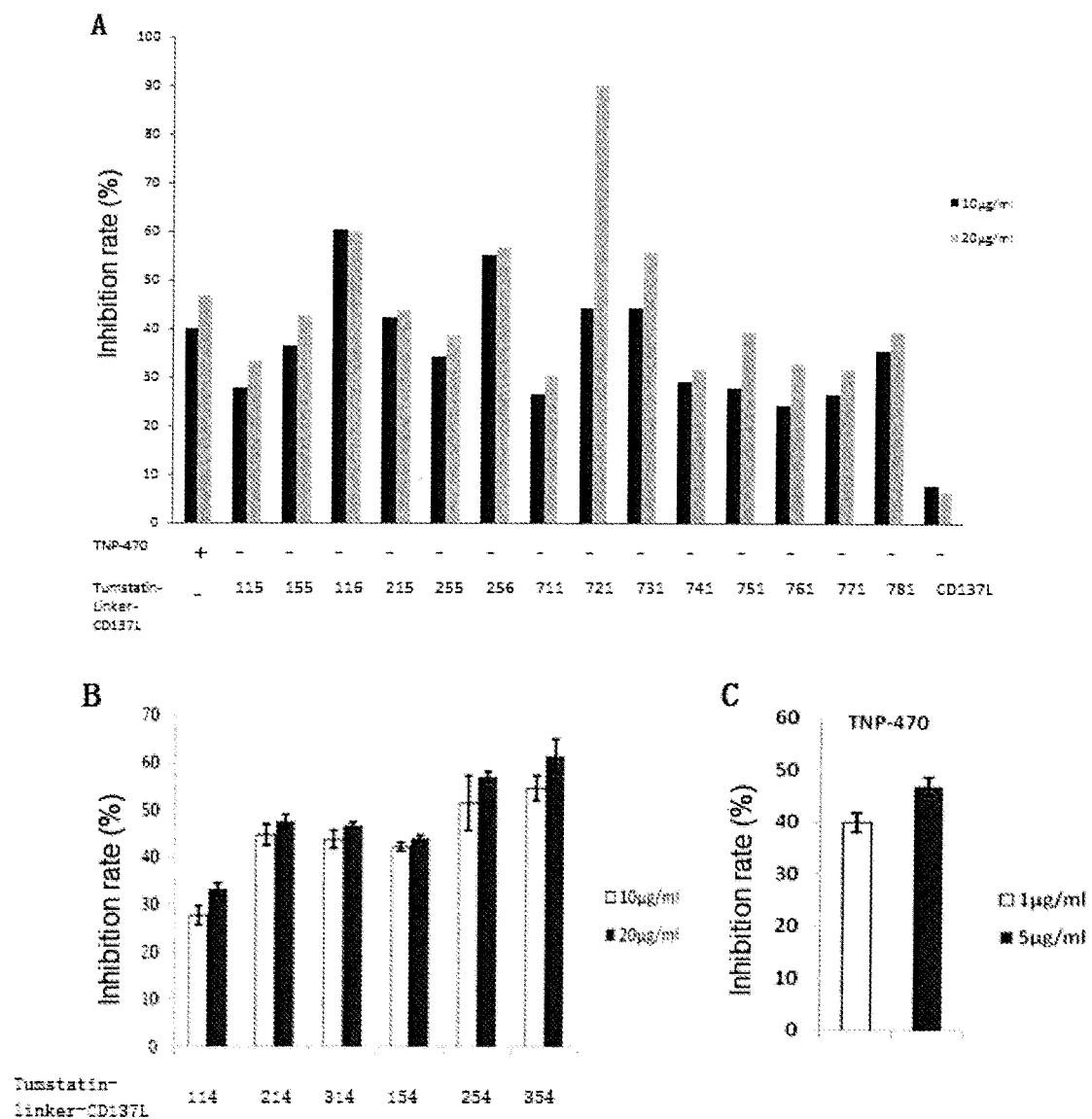

FIG. 7 shows the effects of the representative samples of Tumstatin-Peptide linker-CD137L on the proliferation of human umbilical vein endothelial cells.

Figure 8:
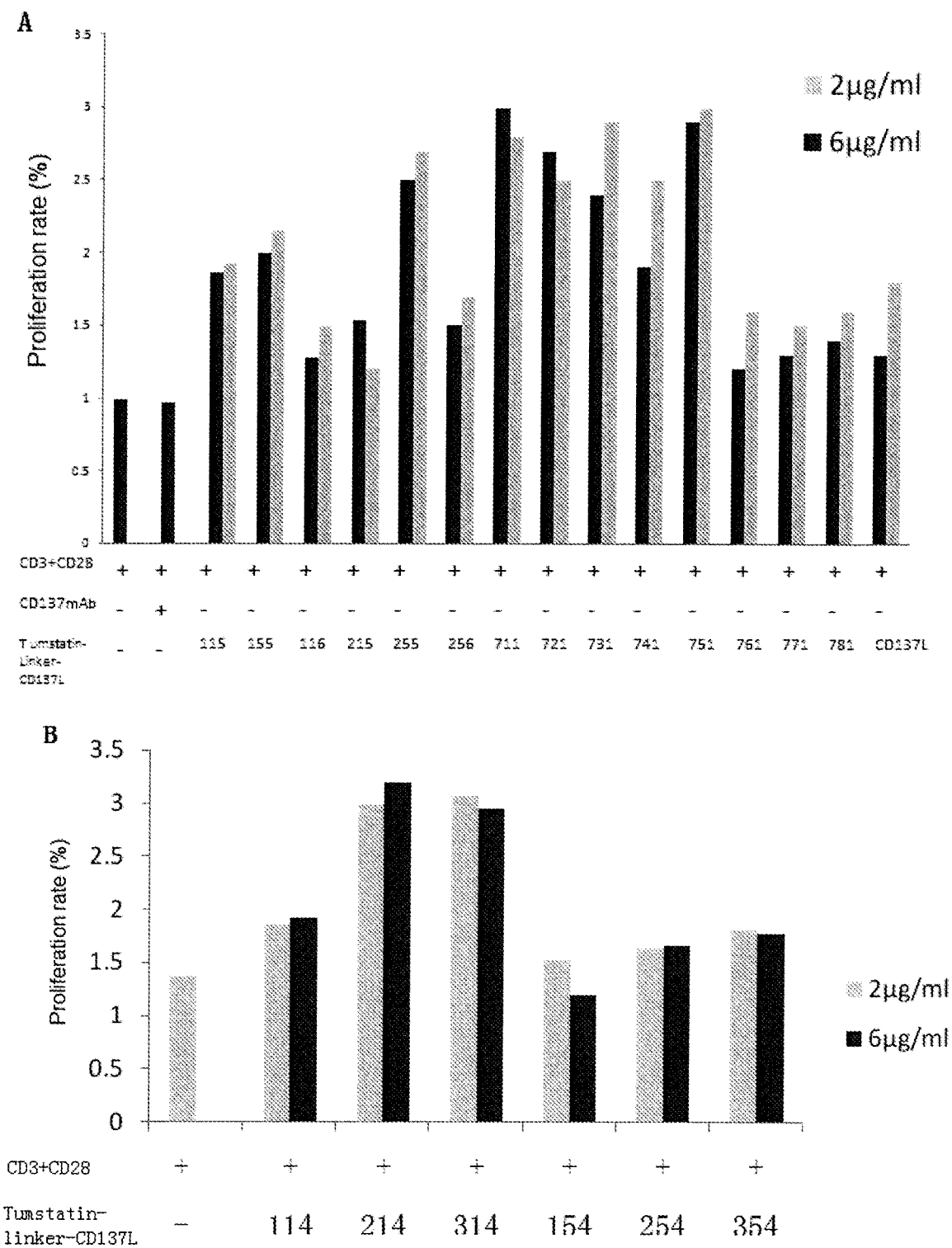

FIG. 8 shows the effects of the representative samples of Tumstatin-Peptide linker-CD137L on the proliferation of mouse T lymphocytes.

DETAILED DESCRIPTION

Hereinbelow, embodiments of the invention will be further explained in more detail by way of the following examples and drawings.

Embodiments of the present invention provide 24 types of bifunctional recombinant proteins possessing activities of Tumstatin and CD137L. The nucleotide sequences of these proteins are shown from SEQ ID NO:1 to SEQ ID NO:24, and the amino acid sequences are shown from SEQ ID NO:25 to SEQ ID NO:48. This group of proteins is made up of one Tumstatin active fragment (Tumstatin1 contains amino acid residues from 45 to 98, Tumstatin2 contains amino acid residues from 60 to 132, Tumstatin3 contains amino acid residues from 60 to 98, Tumstatin7 contains amino acid residues from 74 to 98), one CD137L extracellular domain (CD137L1 contains amino acid residues from 46 to 254, CD137L4 contains amino acid residues from 50 to 240, CD137L5 contains amino acid residues from 83 to 254, CD137L6, a combined fragment, contains amino acid residues from 46 to 85 and from 167 to 254), and a peptide linker with anyone of the amino acid sequences from SEQ ID NO:69 to SEQ ID NO:76. In embodiments of the present invention, two restriction enzyme sites consisting of 5'-EcoRI and 3'-BamHI are designed in the nucleotide sequences (shown from SEQ ID NO:81 to SEQ ID NO:94) containing the the active fragment of Tumstatin and the peptide linker described above. The sequences were synthesized and ligated with plasmid pBluescriptII SK (+) containing the same restriction sites by Shanghai Generay Biological Engineering CO. Ltd.

All the other expression vectors were purchased from Novagen, and *E. coli* strain Top10 and BL21 (DE3) were from Invitrogen. Vector pMD18-T, solution I (#D103A), reverse transcriptase, T4 DNA ligase, restriction endonuclease, such as, NdeI and NheI, were obtained from TAKARA Bio. The synthesis of primers and nucleotide sequencing were completed by Shanghai Invitrogen Biotechnology Company. The urea (AR) used for denaturation and dilution refolding was purchased from Nanjing Chemical Reagent Co., Ltd. Human umbilical vein endothelial cells were purchased from Nanjing KGI Biological Technology Development Co., Ltd. EasySep™ Negative Selection Kit used for mouse T cell proliferation assay was purchased from Stem Cell Company. Anti-CD3 and anti-CD28 monoclonal antibody were purchased from Santa Cruz Company. Other reagents were of analytical grade made in China.

Example 1: The Expression of the Recombinant Protein Tumstatin-CD137L Possessing Activities of Tumstatin and CD137L in *E. coli*

1. Construction of the Expression Systems

Figure 1:
FIG. 1 is a schematic representation showing the structures of the recombinant proteins possessing the activities of Tumstatin and CD137L described in embodiments of the present invention. The amino acid sequence of the flexible peptide linker is selected from anyone of the group from SEQ ID NO:69 to SEQ ID NO:76.
Figure 2:
FIG. 2 is a schematic view illustrating the location of the amino acid sequences of CD137L1 (SEQ ID NO:77), CD137L5 (SEQ ID NO:78), CD137L6 (SEQ ID NO:79) and CD137L4 (SEQ ID NO:80) in the full-length of CD137L.
Figure 2:
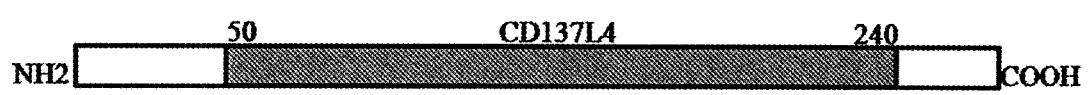
Figure 2:
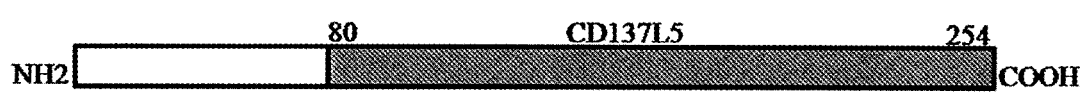
Figure 2:
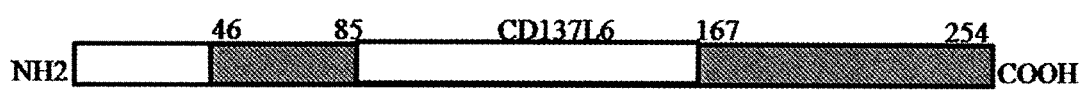

Embodiments of the present invention provide 24 types of bifunctional recombinant proteins possessing activities of Tumstatin and CD137L, which is a fusion of Tumstatin1/Tumstatin2/Tumstatin3/Tumstatin7 and CD137L1/CD137L4/CD137L5/CD137L6 through the combination of a peptide linker (FIG. 1). Wherein, CD137L1, CD137L4, CD137L5 and CD137L6 are the amino acid residues 46-254, 50-240, 83-254, 46-85 plus 167-254 of the full-length of CD137L (FIG. 2), respectively. The nucleotide sequences of the protein are shown from SEQ ID NO:1 to SEQ ID NO:24, the amino acid sequences are shown from SEQ ID NO:25 to SEQ ID NO:48, and the peptide linker is selected from one of the sequences from SEQ ID NO:69 to SEQ ID NO:76.

The nucleotide sequences encoding the amino acid sequences of CD137 extracellular domain (CD137L1 contains amino acid residues from 46 to 254, CD137L4 contains amino acid residues from 50 to 240, CD137L5 contains amino acid residues from 83 to 254, CD137L6, a combined fragment, contains amino acid residues from 46 to 85 and from 167 to 254) are shown from SEQ ID NO:61 to SEQ ID NO:64, and obtained from PCR amplification. Wherein, the full nucleotide sequence of CD137L could be obtained through the published method (Wang shuzhen. J Ind Microbiol Biotechnol. 2012 March; 39(3):471-6. Doi: 10.1007/s10295-011-1045-1.).

Preparation of CD137L template used in embodiments of the present invention by employing the published method described above. Using the upstream primer of SEQ ID NO:61 (SEQ ID NO:95) and the downstream primer of SEQ ID NO:61 (SEQ ID NO:96) as primers, CD137L1 (SEQ ID NO: 61) (with two restriction sites consisting of 5'-BamHI and 3'-NotI) was obtained by PCR amplification with rTaq DNA polymerase and ligated with plasmid pMD18-T. By employing the traditional molecular biology methods (such as enzyme digestion and ligation), the CD137L1 was then cut from plasmid pMD18-T and subcloned into plasmid pBluescriptII SK (+), which contains the gene of Tumstatin and peptide linker (SEQ ID NO:87-SEQ ID NO:94) and was synthesized by Shanghai Generay BiologicalEngineering CO. Ltd. Then, the whole nucleotide sequences of the fusion protein (SEQ ID NO:5-SEQ ID NO:12) were cloned into plasmid pBluescriptII SK(+). Using SEQ ID NO:97 as upstream primer and SEQ ID NO:98 as downstream primer, the genes of the fusion proteins with two restriction sites consisting of 5'-NheI and 3'-NdeI were amplified by PCR and subcloned into the expression vector pET-11a.

Preparation of the CD137L template used in embodiments of the present invention by employing the published method described above. Using the upstream primers of SEQ ID NO:62 (SEQ ID NO:99) and the downstream primer of SEQ ID NO:62 (SEQ ID NO:100) as primers, CD137L5 (SEQ ID NO: 62) (with two restriction sites consisting of 5'-BamHI and 3'-NotI) was obtained by PCR amplification with rTaq DNA polymerase and ligated with plasmid pMD18-T. By employing the traditional molecular biology methods (such asenzyme digestion and ligation), the CD137L5 was then cut from plasmid pMD18-T and subcloned into plasmid pBluescriptII SK (+), which contains the genes of Tumstatin and peptide linker (SEQ ID NO:81-SEQ ID NO:96) and were synthesized by Shanghai Generay BiologicalEngineering CO. Ltd. Then, the whole nucleotide sequences of the fusion proteins (SEQ ID NO:1, SEQ ID NO:3, SEQ ID NO:13-SEQ ID NO:16) were cloned into plasmid pBluescriptII SK (+). Using SEQ ID NO:101-104 as upstream primers and SEQ ID NO:105 as downstream primers, the genes of the fusion proteins with two restriction sites consisting of 5'-NheI and 3'-NdeI was amplified by PCR and subcloned into the expression vector pET-11a.

Preparation of the CD137L template used in embodiments of the present invention by employing the published method described above. Using the upstream primer 1 of SEQ ID NO:63 (SEQ ID NO:106) and the downstream primer 1 of SEQ ID NO:63 (SEQ ID NO:107), the upstream primer 2 of SEQ ID NO:63 (SEQ ID NO:108) and the downstream primer 2 of SEQ ID NO:63 (SEQ ID NO:109) as primers, two fragments of CD137L6 (SEQ ID NO: 63) were obtained by PCR amplification with rTaq DNA polymerase and recovered from the agarose gel. Employing these two fragments as templates, the upstream primer 1 of CD137L6 (SEQ ID NO: 107) and downstream primer 2 of CD137L6 (SEQ ID NO: 109) as primers, CD137L6 (with two restriction sites consisting of 5'-BamHI and 3'-NotI) was obtained through OverlapPCR amplification and ligated with plasmid pMD18-T. The CD137L6 (SEQ ID NO: 63) was then cut from plasmid pMD18-T and subcloned into plasmid pBluescriptII SK (+), which contains the genes of Tumstatin and peptide linker (SEQ ID NO:81, SEQ ID NO:82, SEQ ID NO:84 and SEQ ID NO:86) and were synthesized by Shanghai Generay Biological Engineering CO. Ltd. Using SEQ ID NO:112-113 as primer, the genes of the fusion proteins (SEQ ID NO:2, SEQ ID NO:4, SEQ ID NO:17 and SEQ ID NO:18) were obtained by PCR amplification and subcloned into the expression vector pET-11a.

All the primers involved in the experimental procedures described above are listed as follows:

```
Upstream primer of SEQ ID NO: 61
5'-GGATCCGCCGTCCTTCTCGCCTGCC-3'
(BamHI restriction siteis underlined)

Downstream primer of SEQ ID NO: 61
5'-GCGGCCGCTTCCGACCTCGGTGAAGGGAGT-3'
(NotI restriction siteis underlined)

Upstream primer of the fusion protein
gene (SEQ ID NO: 5-SEQ ID NO: 12)
5'-GCTAGCACAATGCCATTCTTATTCTGCAATG-3'
(NheI restriction siteis underlined)

Downstream primer of the fusion protein
gene (SEQ ID NO: 5-SEQ ID NO: 12)
5'-CATATGTTCCGACCTCGGTGAAGGGAGTCCG-3'
(NdeI restriction siteis underlined)

Upstream primer of SEQ ID NO: 62
5'-CGGGATCCGCCTCTTGGACCTGCGCGGCAG-3'
(BamHI restriction siteis underlined)

Downstream primer of SEQ ID NO: 62
5'-GCGGCCGCTTCCGACCTCGGTGAAGGGAG-3'
(NotI restriction siteis underlined)

Upstream primer of SEQ ID NO: 1
5'-GCTAGCGGTTTTTCTTTCTATTTGTTCAAG-3'
(NheI restriction siteis underlined)

Upstream primer of SEQ ID NO: 3
5'-GCTAGCGGTTTTTCTTTCTTATTTGTTCAAG-3'
(NheI restriction siteis underlined)

Upstream primer of SEQ ID NO: 13-SEQ ID NO: 14
5'-GCTAGCCAAGATTTAGGTACTTTGGGCTCTT-3'
(NheI restriction siteis underlined)

Upstream primer of SEQ ID NO: 15-SEQ ID NO: 16
5'-GCTAGCAAGAGCCCAAAGTACCTAAATCTTG-3'
(NheI restriction siteis underlined)

Downstream primer of SEQ ID NO: 1, SEQ ID NO: 3,
and
SEQ ID NO: 13-SEQ ID NO: 16
5'-CATATGTTCCGACCTCGGTGAAGGAG-3'
(NdeI restriction siteis underlined)

Upstream primer1 of SEQ ID NO: 63
5'-CGGGATCCGCCGTCTTCCTCGCCTGC-3'
(BamHI restriction siteis underlined)

Downstream primer1 of SEQ ID NO: 63
5'-CGCAAACATGCCCTGCCCTG-3'

Upstream primer2 of SEQ ID NO: 63
5'-CAGGGCAGGGCATGTTTGCGGGTTTCCAGGGCCGCTTGC-3'
```

-continued

Downstream primer2 of SEQ ID NO: 63
5'-GCGGCCGCTTCCGACCTCGGTGAAGGGAG-3'
(NotI restriction siteis underlined)

Upstream primer of SEQ ID NO: 2 and SEQ ID NO: 4
5'-GCTAGCGGTTTTCTTTCTTATTTGTTCAAG-3'
(NheI restriction siteis underlined)

Upstream primer of SEQ ID NO: 17
5'-GCTAGCCAAGATTTAGGTACTTTG-3'
(NheI restriction siteis underlined)

Upstream primer of SEQ ID NO: 18
5'-GCTAGCCAAGATTTAGGTACTTTGGGCTCTT-3'
(NheI restriction siteis underlined)

Downstream primer of SEQ ID NO: 2, SEQ ID NO: 4,
SEQ ID NO: 17 and SEQ ID NO: 18
5'-CATAGTTCCGACCTCGGTGAAGGGAG-3'
(NdeI restriction siteis underlined)

PCR amplifications were performed using the following conditions:

94° C. 5 min
94° C. 1 min, 60° C. 30 s, 72° C. 30 s, 30 cycles
72° C. 5 min
4° C.∞, Hold After being recovered from the gel, the PCR products were ligated with plasmid pMD-18T in a total volume of 20 µL containing 1 µL of pMD-18T, 4 µL of target gene and 15 µL of solution. The ligation was carried out at 16° C. for 16 h. The ligation mixture was then used to transform $E.$ $coli$ strain Top10 by calcium chloride method. After being cultured in the solid LB culture medium with ampicillin for 12 h, single clones were picked. The extracted plasmids were then verified by double enzyme digestion with NdeI and NheI. To determine the correctness of the gene sequences, the colonies were sequenced by Shanghai Invitrogen Biotechnology Co. The target genes with expected sequences were ligated with the prokaryotic expression vector pET-11a, wherein the reaction system contains 1 µL of T4 ligase 10× buffer, 1 µL of pET-11a, 7 µL of target gene and 1 µL of T4 ligase, and the ligation was carried out at 16° C. for 16 h. After verified by double enzyme digestion, the gene was transformed into the expression system $E.$ $coli$ BL21 (DE3).

2. The Expression of the Recombinant Proteins 1 mL of $E.$ $coli$ BL21 (DE3) carrying a positive recombinant plasmid was inoculated to 100 mL of LB medium containing 100 µg/mL ampicillin under a super clean bench and cultured at 37° C. in incubator shaker set 250 rpm overnight. The activated seed broth was transferred into sterilized LB medium, in which 100 µM of IPTG was added at an $OD_{600}$ of 0.9. Cells were then harvested by centrifugation (12000 rpm, 30 min) under room temperature after culturing for 8 h at 37° C. Samples (1 g) were re-suspended in 10 mL of PBS, and lysed by high-pressure cell-disruption systems. The lysate was centrifuged for 30 min at 12,000 rpm at 4° C., and the supernatant was discarded and the precipitate was analyzed with SDS-PAGE.

The procedure of SDS-PAGE is described as follows:

1) Wash the appropriate amount of the precipitate with 1 mL of ddH2O, and centrifuge at 12000 rpm for 1 min. After discarding the supernatant, the precipitate was resuspended with 100 µL of ddH2O.

2) Mix 5 µL of 5×SDS-PAGE loading buffer with 20 µL of the resuspended samples and heat them in boiling water for 5 min.

3) Make the 5% stacking gel, 12% separating gel and 1×Tri-Gly running buffer according to the "Molecular Cloning: A Laboratory Manual".

4) Load 20 µL of the prepared samples into wells. Run the electrophoresis at a 90V for 30 min and another 130V for 1 h. Remove SDS-PAGE gel, and use coomassie blue to stain for 1-2 h. The gel is then washed three 3 times with ddH2O, and placed in the bleaching solution overnight.

5) The results of the protein electrophoresis are shown in supplemented drawings. The expression of the target proteins was significantly increased in the positive bacteria as compared to negative control.

Figure 3:
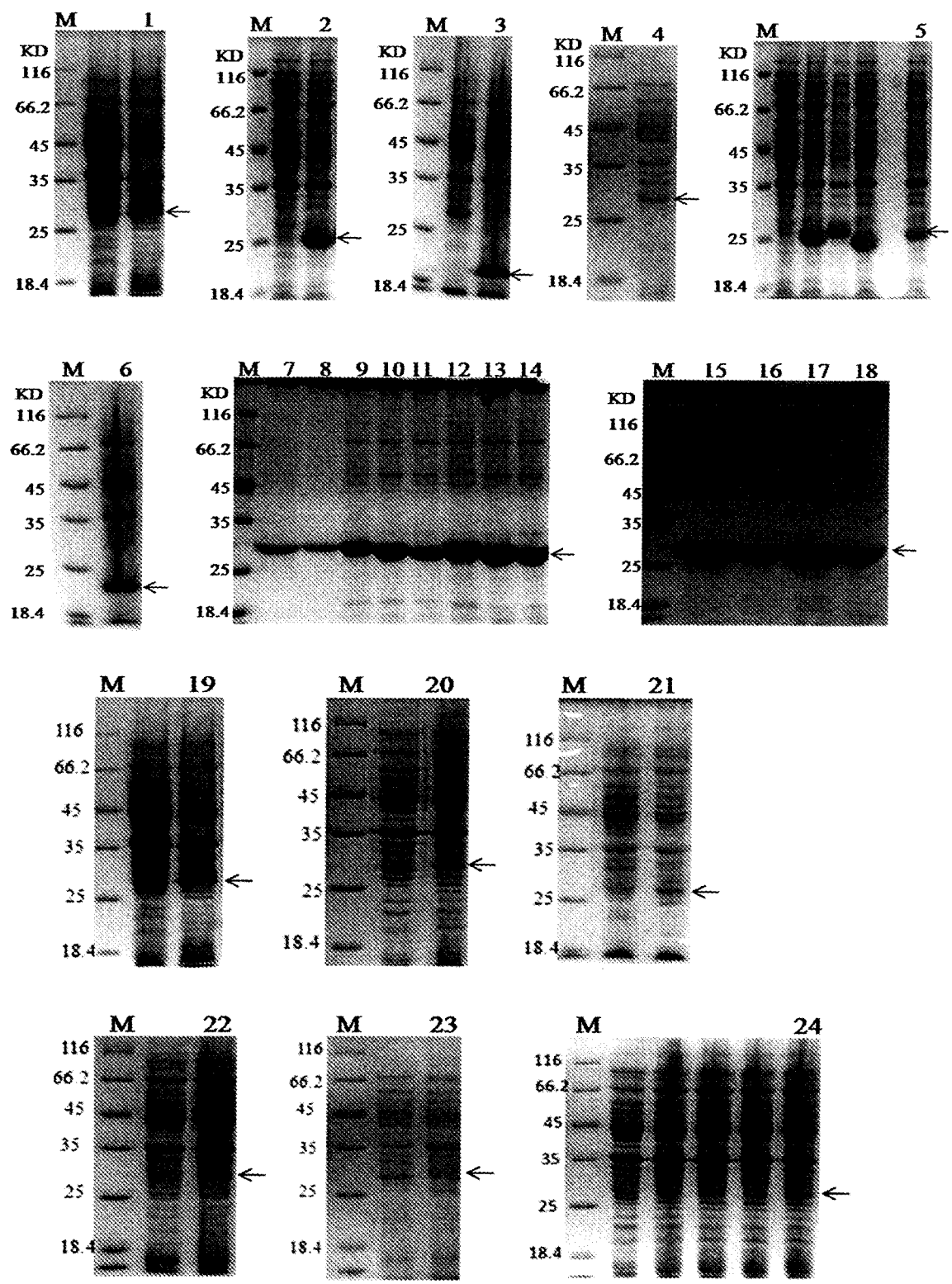
FIG. 3 shows the expression of the recombinant proteins Tumstatin-Peptide linker-CD137L in *E. coli*, the amino acid sequences of which are from SEQ ID NO:25 to SEQ ID NO:48. Lanes 1-24 correspond to SEQ ID NO:25-48, respectively.
Figure 4:
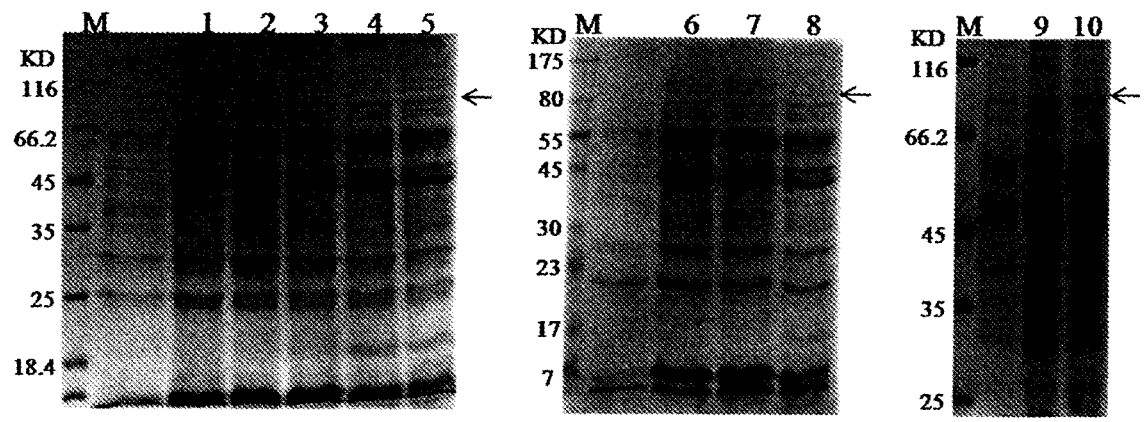
FIG. 4 shows the representative expression of the recombinant proteins Tumstatin-Peptide linker-CD137L (SEQ ID NO:29 to SEQ ID NO:38) in *Bacillus subtilis*. Lanes 1-8 correspond to SEQ ID NO:29, 30, 31, 32, 33, 34, 35, 36, 37 and 38 respectively.
Figure 5:
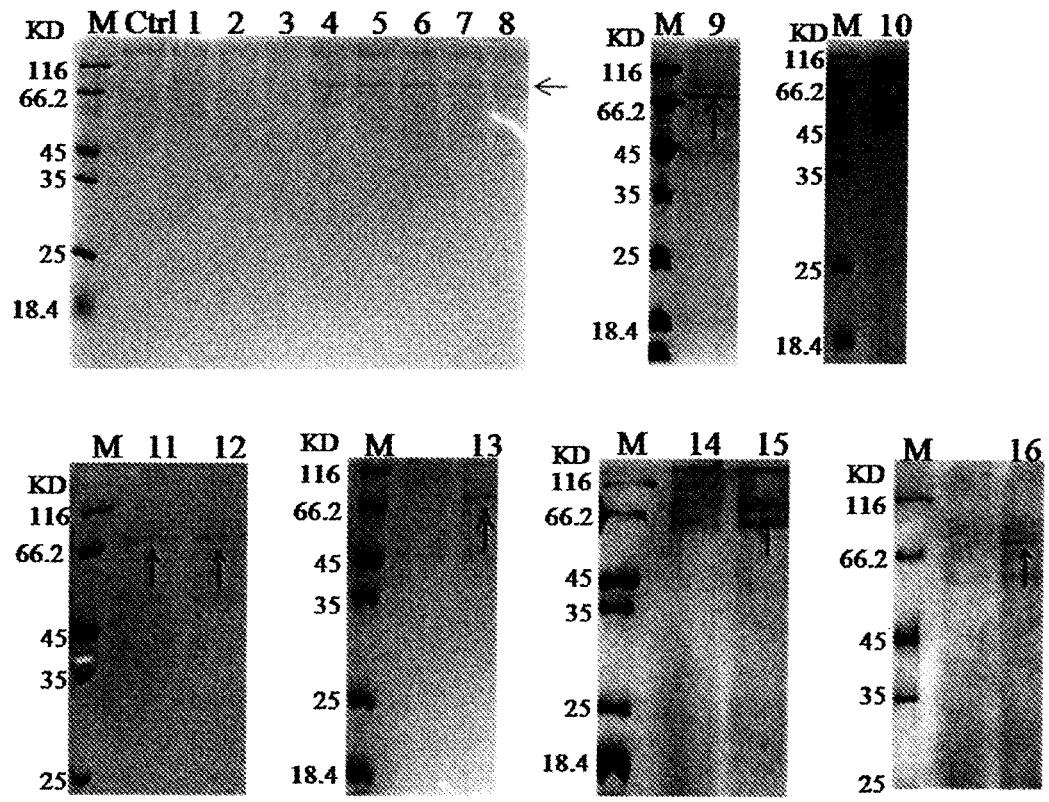
FIG. 5 shows the representative expression of the recombinant proteins Tumstatin-Peptide linker-CD137L (SEQ ID NO:29 to SEQ ID NO:36) in *Pichia pastoris*. Lanes 1-16 correspond to SEQ ID NO:29, 30, 31, 32, 33, 34, 35, 36, 37, 38, 39, 40, 41 and 42, respectively.

Detailed expressions of the target proteins are shown in FIG. 3. It can be observed that all proteins described above were expressed in $E.$ $coli$ BL (DE3).

3. Purification of the Recombinant Proteins

Investigation on the Renaturation of Inclusion Bodies

The bacteria cells were crushed by high-pressure cell-disruption systems as described above. The precipitates were collected and washed twice with washing solution A and B by centrifugation at 12000 rpm for 10 min each time. Solution A consists of 20 mM Tris-HCL, pH8.5, 2 M urea and 2% TritonX-100. Solution B consists of 20 mM Tris-HCL, pH8.5, 2 M urea and 5 mM EDTA. After washing, the precipitates were solubilized at 50° C. overnight with a dissolving solution (20 mM Tris, pH8.5, 8 M urea). After it was completely denatured, the denaturing solution was added to the refolding solution via a constant flow apparatus in chromatography cabinet at 4° C., the solution was stirred at the same time and the process lasted for 12 h. The refolding solution consists of 20 mM Tris-HCL, pH8.5, 2 M urea, 0.4-0.6 M L-Arg and 1 mM EDTA. The solution described above was subjected to ultrafiltration at 4500 rpm for 30 min using Amico Ultra-15 concentration units (Millpore) to concentrate to 1 mL at 4° C. At the same time, the solution was substituted into PBS (pH7.4, 100 mM). The product was preserved at 4° C. (FIG. 6). It was calculated that the purity of the target products after renaturation was greater than 80%, indicating that the denatured inclusion bodies described above were refolded well.

Example 2: The Expression of the Recombinant Proteins Tumstatin-CD137L Possessing Activities of Tumstatin and CD137L in *Bacillus subtilis*

1. Construction of the Expression System

Using the plasmid pBluescriptII SK (+) harboring the complete gene sequences (SEQ ID NO:1-24) of the recombinant proteins constructed in Example 1 as template, PCR amplification of the different fusion genes with different primers with PstI and HindIII at 5' and 3' termini, respectively. After being double enzyme digestion, the PCR products were subcloned into pasmid pP43. The experimental procedure for PCR, enzyme digestion and ligation were the same to those described in Example 1. The constructed plasmid was then transformed into *Bacillus subtilis* WB800 by electroporation (detailed methods can be found in the operating manual of electroporation instrument, Bio-Rad).

2. Expression of the Recombinant Protein

Seed broth culturing: 10 µL of *Bacillus subtilis* strain WB800 harboring the plasimid containing target gene was incubated into 5 mL liquid LB medium containing 50 µg/mL kanamycinunder a super clean bench and cultured at 37° C. on a rotary shaker at 250 rpm for 12 h. Fermentation of the engineered WB800: the activated seed broth was transferred to the aseptic 2×YT medium containing 50 µg/mL kanamycin with an inoculation volume of 10% and cultured at 37°

C. for 96 h, pH7.0. The cells were collected by centrifugation at 4° C. and analyzed by SDS-PAGE.

3. Purification of the Recombinant Proteins

The recombinant proteins were purified by DEAE-sephadex anion exchange chromatography (GE) with PBS, pH8.5.

Example 3: The Expression of the Recombinant Proteins Tumstatin-CD137L Possessing Activities of Tumstatin and CD137L in *Pichia pastoris*

1. Construction of the Expression System

The genes (SEQ ID NO:1-24) of recombinant proteins were obtained by double enzyme digestion of the plasmid pPIC9K with EcoRI and NotI and ligated with plasmid pPIC9K. The constructed plasmid was then transformed into *Pichia pastoris* strain GS115 by electroporation (detailed methods can be found in the operating manual of electroporation instrument, Bio-Rad).

2. Expression of the Recombinant Proteins

*P. pastoris* was cultivated firstly in rich BMGY medium and then BMMY medium for induction of target protein expression. On the first day, the engineered strains constructed above were inoculated into YPD seed medium, and cultured at 37° C. overnight. On the second day, appropriate amount of seed broth was inoculate to BMGY medium and cultured for 48 h. When the value of $OD_{600}$ reached 10, the medium was replaced with BMMY medium. The strains were grown in BMMY medium for 96 h. The cells were collected by centrifugation at 12,000 rpm for 30 min and analyzed by SDS-PAGE.

3. Purification of Recombinant Proteins

The recombinant proteins were purified by DEAE-sephadex anion chromatography (GE) with PBS, pH8.5. The purity of products was greater than 80%.

Example 4: Effects of the Bifunctional Recombinant Proteins Possessing the Activities of Tumstatin and CD137L on the Proliferation of Human Umbilical Vein Endothelial Cells 1) Cell culture: The human umbilical vein endothelial cells (HUVEC) were cultured at 37° C. under constant saturated humidity with 5% $CO_2$ in RPMI1640 medium supplemented with 10% fetal bovine serum, 100 U/mL penicillin and 100 µg/mL of streptomycins for 2~3 d. The cells under exponential-phase growth were used for the following experiments.

2) MTT assay: The cells were seeded in 96-well plates at 5000 cells per well by adding 100 µL cell suspension to each well and cultured in cell culture incubator for 12 h. Then 100 µL of protein samples with different concentrations were added. HUVECs treated with TNP-470 were used as positive control and treated with PBS were used as negative controls. The cells were cultured in triplicate for 48 h. After initiating the cultures for 44 h, 20 µL MTT (5 mg/mL) was added. The medium was then softly removed at 48 h and 150 µL of DMSO was added into each well. The blue-purple precipitates were completely dissolved after shaking the 96-well plate for 10 min. Then the absorbance of each well at 490 nm was measured by a microplate reader.

The results are shown in FIG. 7, wherein, TNP-470 is the positive control, "115" is Tumstatin1-Peptide linker 1-CD137L5 (SEQ ID NO:25), "155" is Tumstatin1-Peptide linker 5-CD137L 5 (SEQ ID NO:27), "116" is Tumstatin1-Peptide linker 1-CD137L6 (SEQ ID NO:26), "215" is Tumstatin2-Peptide linker 1-CD137L5 (SEQ ID NO:37), "255" is Tumstatin2-Peptide linker 5-CD137L5 (SEQ ID NO:38), "256" is Tumstatin2-Peptide linker 5-CD137L 6 (SEQ ID NO:41), "711" is Tumstatin7-Peptide linker 1-CD137L1 (SEQ ID NO:29), "721" is Tumstatin7-Peptide linker 2-CD137L1 (SEQ ID NO:30), "731" is Tumstatin7-Peptide linker 3-CD137L1 (SEQ ID NO:31), "741" is Tumstatin7-Peptide linker 4-CD137L1 (SEQ ID NO:32), "751" is Tumstatin7-Peptide linker 5-CD137L1 (SEQ ID NO:33), "761" is Tumstatin7-Peptide linker 6-CD137L1 (SEQ ID NO:34), "771" is Tumstatin7-Peptide linker 7-CD137L1 (SEQ ID NO:35), "781" is Tumstatin7-Peptide linker 8-CD137L1 (SEQ ID NO:36), "114" is Tumstatin1-Peptide linker 1-CD137L4 (SEQ ID NO:43), "214" is Tumstatin2-Peptide linker 1-CD137L4 (SEQ ID NO:44), "314" is Tumstatin3-Peptide linker 1-CD137L4 (SEQ ID NO:45), "154" is Tumstatin1-Peptide linker 5-CD137L4 (SEQ ID NO:46), "254" is Tumstatin2-Peptide linker 5-CD137L4 (SEQ ID NO:47), "354" is Tumstatin3-Peptide linker 5-CD137L4 (SEQ ID NO:48). The results indicated that these representative recombinant proteins possessing activities of Tumstatin and CD137L could inhibit the proliferation of human umbilical vein endothelial cells, wherein SEQ ID NO:26, SEQ ID NO:37, SEQ ID NO:41, SEQ ID NO:30 and SEQ ID NO:31 showed better inhibitory effects than positive control.

Example 5: Effects of the Bifunctional Recombinant Proteins Possessing the Activities of Tumstatin and CD137L on the Proliferation of Mouse T Cells Mouse T cells were purified from single cell suspensions of mouse splenocytes using EasySep Negative Selection Mouse T Cell Enrichment kit (Stemcell), according to the manufacturer's suggested protocol. Purified T cells were plated at $10^5$ per well in 100 µL medium and cultured in 96-well plates which had been coated with anti-CD3 monoclonal antibody at 7.5 µg/mL overnight at 4° C. Four groups were designed: 1) Blank group without any stimulation (Medium+T cells); 2) the costimulation group in the presence of anti-CD3 (7.5 µg/mL) and anti-CD28 monoclonal antibody (2.5 µg/mL) (CD3/CD28); 3) the costimulation group in the presence of anti-CD137, anti-CD3 and anti-CD28 monoclonal antibody (CD3/CD28/anti-CD137mAb); 4) the costimulation group in the presence of recombinant proteins, anti-CD3 and anti-CD28 monoclonal antibody (CD3/CD28/Tumstatin1-CD137L). The cells were cultured in triplicate for 96 h. After initiating the cultures for 92 h, 10 µL Alamar blue was added. Then, the absorbances of each well at 570 nm and a reference wavelength of 600 nm were determined by a microplate reader. The results are shown in FIG. 8, wherein "115" is Tumstatin1-Peptide linker 1-CD137L5 (SEQ ID NO:25), "155" is Tumstatin1-Peptide linker 5-CD137L5 (SEQ ID NO:27), "116" is Tumstatin1-Peptide linker 1-CD137L6 (SEQ ID NO:26), "215" is Tumstatin2-Peptide linker 1-CD137L5 (SEQ ID NO:37), "255" is Tumstatin2-Peptide linker 5-CD137L5 (SEQ ID NO:38), "256" is Tumstatin2-Peptide linker 5-CD137L6 (SEQ ID NO:41), "711" is Tumstatin7-Peptide linker 1-CD137L1 (SEQ ID NO:29), "721" is Tumstatin7-Peptide linker 2-CD137L1 (SEQ ID NO:30), "731" is Tumstatin7-Peptide linker 3-CD137L1 (SEQ ID NO:31), "741" is Tumstatin7-Peptide linker 4-CD137L1 (SEQ ID NO:32), "751" is Tumstatin7-Peptide linker 5-CD137L1 (SEQ ID NO:33), "761" is Tumstatin7-Peptide linker 6-CD137L1 (SEQ ID NO:34), "771" is Tumstatin7-Peptide linker 7-CD137L1 (SEQ ID NO:35), "781" is Tumstatin7-Peptide linker 8-CD137L1 (SEQ ID NO:36), "114" is Tumstatin1-Peptide linker 1-CD137L4 (SEQ ID NO:43), "214" is Tumstatin2-Peptide linker 1-CD137L4 (SEQ ID NO:44), "314" is Tumstatin3-Peptide linker 1-CD137L4 (SEQ ID NO:45), "154" is Tumstatin1-Peptide linker 5-CD137L4 (SEQ ID NO:46), "254" is Tumstatin2-Peptide linker 5-CD137L4 (SEQ ID NO:47), "354" is Tumstatin3-Peptide linker 5-CD137L4 (SEQ ID NO:48).

The results suggested that these representative recombinant proteins possessing the functions of Tumstatin and CD137L at a final concentration of 2 μg/mL showed higher stimulatory effects on the proliferation of T cells than the costimulatory group "CD3 plus CD28", which proved the significant synergistic effects between CD137L and CD28. Therefore, the representative recombinant proteins having the activities of Tumstatin and CD137L prepared in embodiments of the present invention possess good bioactivities in costimulating the proliferation of T cells.

It is understood that the examples and embodiments described herein are for further illustrative purposes only. Additionally, the examples showed only several types of ligations between different active fragments of Tumstatin and the extracelluar regions of CD137L. Actually, Tumstatin could but not limit to link the extracellular regions of CD137L, and it could also couple with other proteins, peptides or just itself. It will be apparent that various other modifications and adaptations of embodiments of the invention will be apparent to the persons skilled in the art without departing from the spirit and scope of embodiments of the invention and it is intended that all such modifications and adaptations come within the scope of the appended claims.

The invention claimed is:

1. A bifunctional recombinant protein possessing the activities of Tumstatin and CD137L, wherein the recombinant protein comprises a Tumstatin active fragment fused to a CD137L extracellular region through a flexible peptide linker, wherein the amino acid sequence of Tumstatin active fragment is selected from SEQ ID NO:65 to SEQ ID NO:68, wherein the amino acid sequence of the peptide linker is selected from SEQ ID NO:69 to SEQ ID NO:76, wherein the amino acid sequence of CD137L extracellular region is selected from SEQ ID NO:77 to SEQ ID NO:80.

2. The bifunctional recombinant protein according to claim 1, characterized as that the protein contains the amino acid sequence selected from SEQ ID NO:25 to SEQ ID NO:48.

3. A pharmaceutical agent, comprising any one of the bifunctional recombinant protein possessing the activities of Tumstatin and CD137L according to claim 1.

4. The pharmaceutical agent according to claim 3, wherein the pharmaceutical agent inhibits endothelial cell proliferation.

5. The pharmaceutical agent according to claim 3, wherein the pharmaceutical agent stimulates T cell proliferation.

6. The pharmaceutical agent according to claim 3, wherein the pharmaceutical agent inhibits angiogenesis.

* * * * *